US012723267B2

(12) United States Patent
Bastianelli et al.

(10) Patent No.: US 12,723,267 B2
(45) **Date of Patent: *Sep. 1, 2026**

(54) METHOD FOR INDUCING TARGETED MEIOTIC RECOMBINATIONS

(71) Applicants: MEIOGENIX, Paris (FR); INSTITUT CURIE, Paris Cedex 05 (FR); CENTRE NATIONAL DE LA RECHERCHE SCIENTIFIQUE, Paris (FR); SORBONNE UNIVERSITE, Paris (FR)

(72) Inventors: Giacomo Bastianelli, Paris (FR); Alexandre Serero, Colombes (FR); Alain Nicolas, Paris (FR)

(73) Assignees: MEIOGENIX, Paris (FR); INSTITUT CURIE, Paris Cedex (FR); CENTRE NATIONAL DE LA RECHERCHE SCIENTIFIQUE, Paris (FR); SORBONNE UNIVERSITE, Paris (FR)

(*) Notice: Subject to any disclaimer, the term of this patent is extended or adjusted under 35 U.S.C. 154(b) by 1082 days.

This patent is subject to a terminal disclaimer.

(21) Appl. No.: 17/670,549

(22) Filed: Feb. 14, 2022

(65) Prior Publication Data

US 2022/0162647 A1 May 26, 2022

Related U.S. Application Data

(63) Continuation of application No. 15/547,084, filed as application No. PCT/EP2016/052000 on Jan. 29, 2016, now Pat. No. 11,248,240.

(30) Foreign Application Priority Data

Jan. 29, 2015 (FR) .................................... 1550707
Jun. 22, 2015 (FR) .................................... 1555725

(51) Int. Cl.

| | |
|---|---|
| ***C12N 15/90*** | (2006.01) |
| ***C12N 9/22*** | (2006.01) |
| ***C12N 9/90*** | (2006.01) |
| ***C12N 15/11*** | (2006.01) |
| ***C12N 15/65*** | (2006.01) |
| ***C12N 15/81*** | (2006.01) |
| ***C12N 15/82*** | (2006.01) |

(52) U.S. Cl.

CPC .......... *C12N 15/905* (2013.01); *C12N 9/222* (2025.05); *C12N 9/90* (2013.01); *C12N 15/11* (2013.01); *C12N 15/65* (2013.01); *C12N 15/81* (2013.01); *C12N 15/8213* (2013.01); *C12N 15/902* (2013.01); *C12Y 599/01003* (2013.01); *C07K 2319/09* (2013.01); *C12N 2310/20* (2017.05); *C12N 2800/22* (2013.01)

(58) Field of Classification Search

CPC .......... C12N 15/905; C12N 9/22; C12N 9/90; C12N 15/11; C12N 15/65; C12N 15/81; C12N 15/8213; C12N 15/902; C12N 2310/20; C12N 2800/22; C12N 15/102; C12N 15/63; C12Y 599/01003; C07K 2319/09

See application file for complete search history.

(56) References Cited

U.S. PATENT DOCUMENTS

| | | | | |
|---|---|---|---|---|
| 7,273,758 | B2 | 9/2007 | Nicolas et al. | |
| 7,279,334 | B2 | 10/2007 | Nicolas et al. | |
| 11,248,240 | B2 | 2/2022 | Bastianelli et al. | |
| 2004/0033494 | A1 | 2/2004 | Nicolas et al. | |
| 2014/0273235 | A1* | 9/2014 | Voytas .................. | C12N 15/52 435/468 |
| 2015/0307868 | A1 | 10/2015 | Nicolas et al. | |
| 2016/0017393 | A1 | 1/2016 | Jacobson et al. | |
| 2018/0023091 | A1 | 1/2018 | Bastianelli et al. | |
| 2021/0230619 | A1 | 7/2021 | Bastianelli et al. | |
| 2023/0174960 | A1 | 6/2023 | Serero et al. | |
| 2024/0263157 | A1 | 8/2024 | Serero et al. | |

FOREIGN PATENT DOCUMENTS

| | | | |
|---|---|---|---|
| CA | 2963080 | | 4/2016 |
| FR | 1261456 | A | 5/1961 |
| FR | 2 998 898 | | 6/2014 |
| WO | WO 2014/083142 | | 6/2014 |
| WO | WO 2014/099744 | | 6/2014 |
| WO | WO-2014089290 | A1 | 6/2014 |
| WO | WO 2014/104878 | | 7/2014 |
| WO | WO 2016/054326 | | 4/2016 |
| WO | WO-2016120480 | A1 | 8/2016 |
| WO | WO-2016149352 | A1 | 9/2016 |
| WO | WO-2017024047 | A1 | 2/2017 |
| WO | WO-2018197520 | A1 | 11/2018 |

(Continued)

OTHER PUBLICATIONS

Whisstock et al. Quaterly Reviews of Biophysics, 2003, "Prediction of protein function from protein sequence and structure", 36(3):307-340. (Year: 2003).*

(Continued)

*Primary Examiner* — Iqbal H Chowdhury

(74) *Attorney, Agent, or Firm* — Morrison & Foerster LLP

(57) ABSTRACT

The present invention relates to a fusion protein comprising a Cas9 domain and a Spo11 domain, as well as the use of this protein to induce targeted meiotic recombinations in a eukaryotic cell.

33 Claims, 12 Drawing Sheets

Specification includes a Sequence Listing.

(56) References Cited

FOREIGN PATENT DOCUMENTS

WO WO-2019140064 A1 7/2019
WO WO-2021234315 A1 11/2021

OTHER PUBLICATIONS

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10:8-9. (Year: 2002).*
Yu et al. (OsSPO11-1 is essential for both homologous chromosome pairing and crossover formation in rice. Chromosoma (2010), 119:625-636), (Year: 2010).*
Ma et al. (A Robust CRISPR/Cas9 System for Convenient, High-Efficiency Multiplex Genome Editing in Monocot and Dicot Plants. Molecular Plant (2015), 8(8): p. 1274-1284) (Year: 2015).*
Acquaviva et al., (2013). "The Compass subunit Spp1 links histone methylation to initiation of meiotic recombination," Science, 339:215-8, 7 pages.
Baudat et al., (2000). "Chromosome synapsis defects and sexually dimorphic meiotic progression in mice lacking Spo11," Molecular Cell, 6:989-998.
Bergerat et al., (1997). "An atypical topoisomerase II from archaea with implications for meiotic recombination," Nature, 386:414-417.
Care et al., (1999). "The MET3 promoter: a new tool for Candida albicans molecular genetics," Molecular Microb, 34:792-798.
Carlile et al., (2008). "Meiosis I is established through division-specific translational control of a cyclin," Cell, 133:280-91.
Cho et al., (2013). "Targeted genome engineering in human cells with the Cas9 RNA-guided endonuclease," Nature Biotechnology, 31(3):230-232.
Christensen et al., (1996). "Ubiquitin promoter-based vectors for high-level expression of selectable and/or screenable marker genes in monocotyledonous plants," Transgenic Res, 5(3):213-218.
Christensen et al., (1992). "Maize polyubiquitin genes: structure, thermal perturbation of expression and transcript splicing, and promoter activity following transfer to protoplasts by electroporation," Plant Mol Biol, 18(4):675-689.
Cong et al., (2013). "Multiplex genome engineering using CRISPR/Cas systems," Science, 339(6121):819-823, 9 pages.
Egholm et al., (1992). "Peptide nucleic acids (PNA)—Oligonucleotide analogues with an achiral peptide backbone," J. Am. Chem. Soc., 114:1895-1897.
Esposito et al., (1974). "Genetic Recombination and Commitment to Meiosis in *Saccharomyces*," PNAS, 71:3172-3176.
Friedland et al., (2013). "Heritable genome editing in C. elegans via a CRISPR-Cas9 system," Nature Methods, 10(8):741-743, 13 pages.
Grelon et al., (2001). "AtSPO11-1 is necessary for efficient meiotic recombination in plants," Embo J., 20:589-600.
Honigberg et al., (1994). "Reversal of cell determination in yeast meiosis: Postcommitment arrest allows return to mitotic growth," PNAS USA, 91:6559-6563.
Hwang et al., (2013). "Efficient in Vivo Genome Editing Using RNA-Guided Nucleases," Nature Biotechnology, 31(3):227-229, 12 pages.
Jiang et al., (2013). "Demonstration of CRISPR/Cas9/sgRNA-mediated targeted gene modification in *Arabidopsis*, tobacco, sorghum and rice," Nucleic Acids Research, 41(20):e188, 12 pages.
Jiang et al., (2013). "RNA-guided editing of bacterial genomes using CRISPR-Cas systems," Nature Biotechnology, 31(3):233-239, 23 pages.
Jinek et al., (2012). "A programmable dual-RNA-guided DNA endonuclease in adaptive bacterial immunity," Science, 337:816-821.
Kassir et al., (1991). "Monitoring meiosis and sporulation in *Saccharomyces cerevisiae*," Meth. Enzymol., 194:94-110.
Keeney, (2001). "Mechanism and control of meiotic recombination initiation," Curr. Top. Dev. Biol, 52:1-53.
Li et al., (2013). "Heritable gene targeting in the mouse and rat using a CRISPR-Cas system," Nature Biotechnology, 31(8):681-683.
Makarova et al., (2011). "Evolution and classification of the CRISPR-Cas systems," Nat. Rev. Microbiol., 9:467-477, 23 pages.
Mali et al., (2013). "RNA-guided human genome engineering via Cas9," Science, 339(6121):823-826, 8 pages.
Malkova et al., (1996). "Meiotic Recombination Initiated by a Double-Strand Break in rad50A Yeast Cells Otherwise Unable to Initiate Meiotic Recombination," Genetics, 143:741-754.
McKim et al., (1998). "mei-W68 in *Drosophila melanogaster* encodes a Spo11 homolog: evidence that the mechanism for initiating meiotic recombination is conserved," Genes Dev, 12(18):2932-42.
Murakami et al., (2009). "Locally, meiotic double-strand breaks targeted by Gal4BD- Spo11 occur at discrete sites with a sequence preference," Mol. Cell. Biol, 29:3500-16.
Nakayama et al., (2013). "Simple and efficient CRISPR/Cas9-mediated targeted mutagenesis in Xenopus tropicalis," Genesis, 51(12):835-843, 15 pages.
Neale, (2002). "Wild-Type Levels of Spo11-Induced DSBs Are Required for Normal Single-Strand Resection during Meiosis," Molecular Cell, 9:835-846.
Sallaud et al., (2003). "Highly efficient production and characterization of T-DNA plants for rice (*Oryza sativa* L.) functional genomics," Theor Appl Genet, 106(8):1396-1408.
Shan et al., (2013). "Targeted genome modification of crop plants using a CRISPR-Cas system," Nature Biotechnology, 31(8):686-688.
Shao et al., (2017). "Enhancing CRISPR/Cas9-mediated homology-directed repair in mammalian cells by expressing *Saccharomyces cerevisiae* Rad52," International Journal of Biochemistry and Cell Biology, 92:43-52.
Sherman et al., (1963). "Evidence for Two Types of Allelic Recombination in Yeast," Genetics, 48:255-261.
Sherman, (1991). "Getting started with yeast," Meth. Enzymol., 194:3-21.
Shingu et al., (2012). "The double-stranded break-forming activity of plant SPO11s and a novel rice SPO11 revealed by a *Drosophila* bioassay," BMC Mol Biol, 13:1, 16 pages.
Smith et al., (1998). "Recombination at work for meiosis," Curr. Opin. Genet. Dev, 8:200-211.
Sprink et al., (2014). "The splicing fate of plant SPO11 genes," Frontiers in Plant Science, 5:214, 9 pages.
Taagen et al., (2020). "Counting on Crossovers: Controlled Recombination for Plant Breeding," Trends in Plant Science, 26(5):455-465.
Tang et al., (2019). "Methods for Enhancing Clustered Regularly Interspaced Short Palindromic Repeats/Cas9-Mediated Homology-Directed Repair Efficiency," Frontiers in Genetics, 10:551, 9 pages.
Wang et al., (2013). "One-Step Generation of Mice Carrying Mutations in Multiple Genes by CRISPR/Cas-Mediated Genome Engineering," Cell, 153(4):910-918, 17 pages.
Wu et al., (1994). "Meiosis-Induced Double-Strand Break Sites Determined by Yeast Chromatin Structure," Science, 263:515-518.
Yang et al., (2014). "Effective gene targeting in rabbits using RNA-guided Cas9 nucleases," Journal of Molecular Cell Biology, 6(1):97-99.
Yu et al., (2013). "Highly efficient genome modifications mediated by CRISPR/Cas9 in *Drosophila*," Genetics, 195(1):289-291.
Zenvirth et al., (1997). "Switching yeast from meiosis to mitosis: double-strand break repair, recombination and synaptonemal complex," Genes to Cells, 2:487-498.
Safari et al., (2019). "CRISPR Cpf1 proteins: structure, function and implications for genome editing," Cell Biosci, 9:36, 21 pages.
Dicarlo, J. E. et al. "Genome engineering in *Saccharomyces cerevisiae* using CRISPR-Cas systems" *Nucleic Acids Research*, Mar. 4, 2013, pp. 4336-4343, vol. 41, No. 7.

(56) References Cited

OTHER PUBLICATIONS

Jinek, M. et al. "A Programmable Dual-RNA-Guided DNA Endonuclease in Adaptive Bacterial Immunity" Science, Jun. 28, 2012, pp. 1-37.
Lam, I. et al. "Mechanism and regulation of meiotic recombination initiation" *Cold Spring Harbor Perspectives in Biology*, Nov. 7, 2015, pp. 1-34, vol. 7, No. 1.
Peciña, A. et al. "Targeted Stimulation of Meiotic Recombination" *Cell*, Oct. 18, 2002, pp. 173-184, vol. 111.
Written Opinion in International Application No. PCT/EP2016/052000, Mar. 17, 2016, pp. 1-6.
Origene, "In vitro digestion of DNA with Cas9 nuclease and sgRNA" date unknown, pp. 1-2.
Morrill, G. A. et al. "Role of Calcium in Regulating Intracellular pH Following the Stepwise Release of the Metabolic Blocks at First-Meiotic Prophase and Second-Meiotic Metaphase in Amphibian Oocytes" *Biochimica et Biophysica Acta*, 1984, pp. 107-117, vol. 804.
MacGregor, I. A. et al. "Large-scale chromatin organisation in interphase, mitosis and meiosis" *Biochemical Journal*, 2019, pp. 2141-2156, vol. 476.
Kasama, T. et al. "Spo5/Mug12, a Putative Meiosis-Specific RNA-Binding Protein, Is Essential for Meiotic Progression and Forms Mei2 Dot-Like Nuclear Foci" *Eukaryotic Cell*, Aug. 2006, pp. 1301-1313 vol. 5, No. 8.
Valton, J. et al. "5'-Cytosine-Phosphoguanine (CpG) Methylation Impacts the Activity of Natural and Engineered Meganucleases" *The Journal of Biological Chemistry*, Aug. 31, 2012, pp. 30139-30150, vol. 287, No. 36.
Panizza, S. et al. "Spo11-Accessory Proteins Link Double-Strand Break Sites to the Chromosome Axis in Early Meiotic Recombination" *Cell*, Aug. 5, 2011, pp. 372-383, vol. 146.
Sarno, R. et al. "Programming sites of meiotic crossovers using Spo11 fusion proteins" *Nucleic Acids Research*, 2017, pp. 1-14, vol. 45, No. 19, e164.
Li, W. et al. "Double-stranded DNA breaks and gene functions in recombination and meiosis" *Cell Research*, 2006, pp. 402-412, vol. 16.
Bassett, A. R. et al. "CRISPR/Cas9 and Genome Editing in *Drosophila*" *Journal of Genetics and Genomics*, 2014 (available online Dec. 18, 2013), pp. 7-19, vol. 41.
Liti, G. et al. "Advances in Quantitative Trait Analysis in Yeast" *PLOS Genetics*, Aug. 2012, pp. 1-7, vol. 8, Issue 8, e1002912.
Machine translation of FR2998898, printed as pp. 1-27 on Apr. 25, 2019.
Bowles, J. et al. "Retinoid Signaling Determines Germ Cell Fate in Mice" *Science*, Apr. 28, 2006, pp. 596-600, vol. 312, No. 5773.
Milo et al. "What Are the Concentrations of Different Ions in Cells?" http://book.bionumbers.org/what-are-the-concentrations-of-different-ions-in-cells/, printed as pp. 1/5-5/5 on Dec. 20, 2016 from the online version of Cell Biology by the Numbers, published Dec. 7, 2015.
Scott, J. N. F. et al. "Targeted genome regulation and modification using transcription activator-like effectors" *The FEBS Journal*, Sep. 6, 2014, pp. 4583-4597, vol. 281, No. 20.
Carroll, D. "A Crispr Approach to Gene Targeting" *Molecular Therapy*, Sep. 2012, pp. 1658-1660, vol. 20, No. 9.
Nishimasu, H. et al. "Crystal Structure of Cas9 in Complex with Guide RNA and Target DNA" *Cell*, Feb. 27, 2014, pp. 935-949, vol. 156.
Ding, Y. et al. "Recent Advances in Genome Editing Using CRISPR/Cas9" *Frontiers in Plant Science*, May 24, 2016, pp. 1-12, vol. 7, Article 703.
Hunter, N. "Synaptonemal Complexities and Commonalities" *Molecular Cell*, Sep. 2003, pp. 533-535, vol. 12.
Lam, I. et al. "Mechanism and Regulation of Meiotic Recombination Initiation" *Cold Spring Harbor Perspectives in Biology*, Oct. 2014, pp. 1-25, vol. 7, No. 1, a016634.
Baudat, F. et al. "SPO11: une activite de coupure de l'ADN indispensable a la meiose" *Medicine/Sciences*, vol. 20, pp. 213-218, 2004, including pp. 1/7-7/7 of machine translation.
Sun, Y.-C. et al. "Reconstitution of Gametogenesis in Vitro: Meiosis Is the Biggest Obstacle" *Journal of Genetics and Genomics*, Feb. 22, 2014, pp. 87-95, vol. 41.
Rönspies, M. et al. "CRISPR-Cas-mediated chromosome engineering for crop improvement and synthetic biology" *Nature Plants*, DOI: 10.1038/s41477-021-00910-4, online ahead of print, May 6, 2021, pp. 1-8.
Yelina, N. E. et al. "CRISPR targeting of Meiotic-Topoisomerase VIB-dCas9 to a recombination hotspot is insufficient to increase crossover frequency in *Arabidopsis*" Preprint at bioRxiv https://doi.org/10.1101/2021.02.01.429210, Feb. 2, 2021, printed as pp. 1-42.
He et al., (2020). "Cas3 protein-a review of a multi-tasking machine," Genes, 11:208, 14 pages.
Laughery et al., (2019). "R-loop formation by dCas9 is mutagenic in *Saccharomyces cerevisiae*," Nucleic Acids Research, 47:2389-2401. Published Online 2018.
Makarova et al., (2020). "Evolutionary classification of CRISPR-Cas systems: a burst of class 2 and derived variants," Nature Reviews Microbiology, 18:67-83, 36 pages.
Mali et al., (2013). "Cas9 as a versatile tool for engineering biology," Nature Methods, 10:957-963, 16 pages.
McGinn et al., (2019). "Molecular mechanisms of CRISPR-Cas spacer acquisition," Nature Reviews Microbiology, 17:7-12, 6 pages.
Miao et al., (2019). "Systematically investigating the key features of the DNase deactivated Cpf1 for tunable transcription regulation in prokaryotic cells," Synthetic and Systems Biotechnology, 4:1-9.
Sadowski et al., (2009). "The sequence—structure relationship and protein function prediction," Current Opinion in Structural Biology, 19:357-362.
Sasanuma et al., (2007). "Meiotic association between Spo11 regulated by Rec102, Rec104 and Rec114," Nucleic Acids Research, 35:1119-1133.
Seffernick et al., (2001). "Melamine deaminase and atrazine chlorohydrolase: 98 percent identical but functionally different," J. Bacterial., 183(8):2405-2410.
Singh et al., (2018). "Protein Engineering Approaches in the Post-Genomic Era," Current Protein and Peptide Science, 19(1):5-15.
Tang et al., (2013). "Identification of Dehalobacter reductive dehalogenases that catalyse dechlorination of chloroform, 1,1,1-trichloroethane and 1,1-dichloroethane," Phil Trans R Soc B, 368:20120318, 10 pages.
Tang et al., (2021). "Programmable system of Cas13-mediated RNA modification and its biological and biomedical applications," Frontiers in Cell and Developmental Biology, 9:677587, 15 pages.
Fayos et al., (2019). "Engineering meiotic recombination pathways in rice," Plant Biotechnology Journal, 17(11):2062-2077.
Weitzel et al., (2021). "Meiotic Cas9 expression mediates gene conversion in the male and female mouse germline," PLoS Biol, 19(12):e3001478, 16 pages.
Yelina et al., (2021). "CRISPR targeting of Meiotic-Topoisomerase VIB-dCas9 to a recombination hotspot is insufficient to increase crossover frequency in *Arabidopsis*," bioRxiv, available online at <https://www.biorxiv.org/content/10.1101/2021.02.01.429210v1>, 42 pages.
Da Ines et al., (2020). "Bread wheat TaSPO11-1 exhibits evolutionarily conserved function in meiotic recombination across distant plant species," The Plant Journal, 103:2052-2068.
Herbert et al., (2025). "dCas9-SP011-1 locally stimulates meiotic recombination in rice," Front. Plant Sci. 16:1580225, 20 pages.

* cited by examiner

A

B

| Genotype | parental Ditype | Tetratype | Non Parental Ditype | cM | p value vs *SpCAS9*-SPO11*+ sgRNA handle | p value vs *SPO11* |
|---|---|---|---|---|---|---|
| *SPO11* | 183 | 8 | 0 | **2.1** | - | - |
| *SpCAS9*-SPO11* + sgRNA handle | 104 | 10 | 0 | **4.4** | - | 0,13 |
| *SpCAS9*-SPO11* + sgRNA-Gal4UAS$_{D/E}$ | 142 | 16 | 0 | **5.1** | 0,84 | 0,03 |
| *SpCAS9*-SPO11* + Multi gRNAs | 131 | 28 | 1 | **10.6** | 0,008 | < 0,001 |

Guide RNA-UAS1 (*YCR048W* coding sequence)
5′ CACACCTGAAGAGCAAGTCTgttttagagctagaaatagcaagttaaaataaggctagt
ccgttatcaacttgaaaaagtggcaccgagtcggtgcttttt 3′ (SEQ ID NO: 10)

Guide RNA-UAS2 (*YCR048W* coding sequence)
5′ TTCCACAACACGCCCACCTTgttttagagctagaaatagcaagttaaaataaggctagt
ccgttatcaacttgaaaaagtggcaccgagtcggtgcttttt 3′ (SEQ ID NO: 11)

Guide RNA-UAS D/E (*GAL2* promoter)
5′ GATCACTCCGAACCGAGATTgttttagagctagaaatagcaagttaaaataaggctagt
ccgttatcaacttgaaaaagtggcaccgagtcggtgcttttt 3′ (SEQ ID NO: 12)

sgRNA-SWC3 (*SWC3* coding sequence)
5′ TGCGATTGTGTAATGAGTGGgttttagagctagaaatagcaagttaaaataaggctagt
ccgttatcaacttgaaaaagtggcaccgagtcggtgcttttt 3′ (SEQ ID NO:13)

sgRNA-UAS-A (GAL2 promoter)
5′ CAATTCGGAAAGCTTCCTTCgttttagagctagaaatagcaagttaaaataaggctagt
ccgttatcaacttgaaaaagtggcaccgagtcggtgcttttt 3′ (SEQ ID NO:14)

sgRNA-UAS-B (*GAL2* promoter)
5′ TTGCCTCAGGAAGGCACCGGgttttagagctagaaatagcaagttaaaataaggctagt
ccgttatcaacttgaaaaagtggcaccgagtcggtgcttttt 3′ (SEQ ID NO:15)

sgRNA-PUT4 (PUT4 sequence)
5′ GTTTTGAATTCCGATCACAAgttttagagctagaaatagcaagttaaaataaggctagt
ccgttatcaacttgaaaaagtggcaccgagtcggtgcttttt 3′ (SEQ ID NO:17)

Figure 13

METHOD FOR INDUCING TARGETED MEIOTIC RECOMBINATIONS

CROSS-REFERENCE TO RELATED APPLICATIONS

This application is a continuation of U.S. application Ser. No. 15/547,084, filed Jul. 28, 2017, now U.S. Pat. No. 11,248,240, which is the U.S. national stage application of International Patent Application No. PCT/EP2016/052000, filed Jan. 29, 2016.

The Sequence Listing for this application is labeled "Seq-List.txt" which was created on Jul. 3, 2017 and is 84 KB. The entire content of the sequence listing is incorporated herein by reference in its entirety.

The present invention falls within the field of the eukaryotes, more particularly within the field of microbiology. It concerns notably a method for improving or modifying a yeast strain by inducing targeted meiotic recombinations.

TECHNOLOGICAL BACKGROUND OF THE INVENTION

Yeasts are used in a wide variety of industries. Due to the harmlessness of a large number of species, yeasts are especially used in the food industry as a fermentation agent in baking, brewing, winemaking or distilling, or as extracts for nutritional elements or flavorings. They may also be used in the industrial production of bioethanol or of molecules of interest such as vitamins, antibiotics, vaccines, enzymes or steroid hormones, or in cellulosic material degradation processes.

The diversity of the industrial applications of yeasts means that there is a constant demand for yeast strains having improved characteristics, or at least that are suitable for a new usage or new culture conditions.

To obtain a strain having a specific characteristic, a person skilled in the art may use sexual reproduction by crossing two parental strains having characteristics of interest and by selecting a hybrid strain providing the desired combination of parental characteristics. This method is however random and the selection step may be costly in terms of time.

Alternatively, the strain may also be genetically modified by a recombinant DNA technique. This modification may nevertheless act to curb its use, whether for legal, health or environmental reasons.

A third alternative consists in causing a reassortment of paternal and maternal alleles in the genome, during meiotic recombination. Meiotic recombination is an exchange of DNA between homologous chromosomes during meiosis. It is initiated by the formation of double-strand breaks in one or the other homologous chromatid, followed by repair of these breaks, using as matrix a chromatid of the homologous chromosome. However, meiotic recombinations have the disadvantage of being random and nonuniform. Indeed, the double-strand break sites at the origin of these recombinations are not distributed homogeneously in the genome. So-called 'hotspot' regions of the chromosome, where the recombination frequency is high, can thus be distinguished from so-called 'cold' regions of the chromosome, where the recombination frequency may be up to 100 times lower.

Spo11 is the protein that catalyzes double-strand breaks during meiosis. It acts as a dimer in cooperation with numerous partners. At present, the factors determining the choice of double strand break sites by Spo11 and its partners remain poorly understood.

Controlling the formation of double-strand breaks and, in fact, meiotic recombinations, is crucial to the development of genetic engineering techniques. It was recently shown that it is possible to modify double-strand break formation sites by fusing Spo11 with the DNA binding domain of the transcriptional activator Gal4 (Peciña et al., 2002 Cell, 111, 173-184). The Gal4 Spo11 fusion protein makes it possible to introduce double-strand breaks in so-called 'cold' chromosomal regions, at the Gal4 DNA binding sites.

However, in this last approach, the introduction of double-strand breaks is conditioned by the presence of Gal4 binding sites, and thus it remains impossible to induce targeted meiotic recombination phenomena independently of specific binding sites.

SUMMARY OF THE INVENTION

The objective of the present invention is to propose a method for inducing targeted meiotic recombinations in eukaryotic cells, preferably in yeast or plant cells, in any region of the genome, independently of any known binding site, and notably in so-called 'cold' chromosomal regions.

Thus, according to a first aspect, the present invention relates to a method for inducing targeted meiotic recombinations in a eukaryotic cell comprising:

introducing into said cell:

a) a fusion protein comprising a Cas9 domain and a Spo11 domain, or a nucleic acid encoding said fusion protein; and b) one or more guide RNAs or one or more nucleic acids encoding said guide RNAs, said guide RNAs comprising an RNA structure for binding to the Cas9 domain of the fusion protein and a sequence complementary to the targeted chromosomal region; and inducing said cell to enter meiotic prophase I.

The fusion protein may further comprise a nuclear localization signal sequence.

Preferably, the Cas9 domain of the fusion protein is a nuclease-deficient Cas9 protein.

The nucleic acid encoding said fusion protein may be placed under the control of a constitutive, inducible or meiosis-specific promoter.

One or more additional guide RNAs targeting one or more other chromosomal regions, or nucleic acids encoding said additional guide RNAs, may be introduced into the eukaryotic cell.

Preferably, the eukaryotic cell is a yeast. The yeast can then be induced to enter prophase I by transferring it to sporulation medium.

Alternatively, the eukaryotic cell is a plant cell.

Preferably, the introduction of the fusion protein, or the nucleic acid encoding same, and the gRNA(s), or the nucleic acid(s) encoding same, into said cell is simultaneous.

Alternatively, the introduction of the fusion protein, or the nucleic acid encoding same, and the gRNA(s), or the nucleic acid(s) encoding same, into said cell is sequential.

The introduction of the nucleic acid encoding the fusion protein and the nucleic acid(s) encoding the gRNA(s) into said cell may also be achieved by crossing two cells into which have been respectively introduced the nucleic acid encoding the fusion protein and the nucleic acid(s) encoding the gRNA(s).

The present invention further concerns, according to a second aspect, a fusion protein as defined in the method above.

According to a third aspect, the present invention further concerns a nucleic acid encoding the above-defined fusion protein.

The present invention also concerns, according to a fourth aspect, an expression cassette or a vector comprising a nucleic acid as defined above.

Preferably, the vector is a plasmid comprising a bacterial origin of replication, an expression cassette comprising a nucleic acid as defined above, one or more selection markers, and/or one or more sequences allowing targeted insertion of the vector, the expression cassette or the nucleic acid into the host-cell genome. In particular, the plasmid comprises a bacterial origin of replication, preferably the ColE1 origin, an expression cassette comprising a nucleic acid as defined above under the control of a promoter, preferably the ADH1 promoter, a terminator, preferably the ADH1 terminator, one or more selection markers, preferably resistance markers such as the gene for resistance to kanamycin or to ampicillin, one or more sequences allowing targeted insertion of the vector, the expression cassette or the nucleic acid into the host-cell genome, preferably at the TRP1 locus of the genome of a yeast. Preferably, the plasmid comprises, or consists of, a nucleotide sequence selected from SEQ ID NO: 1 and SEQ ID NO: 2.

According to a fifth aspect, the present invention also concerns a host cell comprising a fusion protein, a nucleic acid, a cassette or a vector as defined above.

Preferably, the host cell is a eukaryotic cell, more preferably a yeast, plant, fungal or animal cell, and particularly preferably, the host cell is a plant cell or a yeast cell.

Preferably, the host cell is a yeast cell, more preferably a yeast selected from the group consisting of *Saccharomyces cerevisiae, Saccharomyces bayanus, Saccharomyces castelli, Saccharomyces eubayanus, Saccharomyces kluyveri, Saccharomyces kudriavzevii, Saccharomyces mikatae, Saccharomyces uvarum, Saccharomyces paradoxus, Saccharomyces pastorianus* (also called *Saccharomyces carlsbergensis*), and the hybrids obtained from at least one strain belonging to one of these species, and particularly preferably the host cell is *Saccharomyces cerevisiae.*

Alternatively, the host cell is a plant cell, more preferably a plant cell selected from the group consisting of rice, wheat, soy, maize, tomato, *Arabidopsis thaliana*, barley, rapeseed, cotton, sugarcane and beet, and particularly preferably said host cell is a rice cell.

The present invention further concerns, in a sixth aspect, a method for generating variants of a eukaryotic organism, with the exception of humans, comprising:

introducing into a cell of said organism:

a) a fusion protein comprising a Cas9 domain and a Spo11 domain, or a nucleic acid encoding said fusion protein; and b) one or more guide RNAs, or one or more nucleic acids encoding said guide RNAs, said guide RNAs comprising an RNA structure for binding to the Cas9 domain and a sequence complementary to a targeted chromosomal region; and inducing said cell to enter meiotic prophase I;

obtaining a cell or cells having the desired recombination(s) at the targeted chromosomal region(s); and generating a variant of the organism from said recombinant cell.

Preferably, the eukaryotic organism is a yeast or a plant, more preferably a yeast, notably a yeast strain of industrial interest.

In a seventh aspect, the present invention also concerns a method for identifying or locating the genetic information encoding a characteristic of interest in a eukaryotic cell genome comprising:

introducing into the eukaryotic cell:

a) a fusion protein comprising a Cas9 domain and a Spo11 domain, or a nucleic acid encoding said fusion protein; and b) one or more guide RNAs, or one or more nucleic acids encoding said guide RNAs, said guide RNAs comprising an RNA structure for binding to the Cas9 domain and a sequence complementary to a targeted chromosomal region; and inducing said cell to enter meiotic prophase I;

obtaining a cell or cells having the desired recombination(s) at the targeted chromosomal region(s); and analyzing the genotypes and phenotypes of the recombinant cells in order to identify or to locate the genetic information encoding the characteristic of interest.

Preferably, the eukaryotic cell is a yeast or a plant, more preferably a yeast, notably a yeast strain of industrial interest.

Preferably, the characteristic of interest is a quantitative trait of interest (QTL).

The present invention further concerns, in an eighth aspect, a kit comprising a fusion protein, a nucleic acid, a cassette, a vector or a host cell as defined above.

Finally, in a ninth aspect, the present invention concerns the use of a kit as defined above to implement a method as defined above, in particular to (i) induce targeted meiotic recombinations in a eukaryotic cell, (ii) generate variants of a eukaryotic organism, and/or (iii) identify or locate the genetic information encoding a characteristic of interest in a eukaryotic cell genome.

(AND2822), spo11/spo11 dCAS9-SPO11/0 (AND2820) and spo11/spo11 dCAS9-SPO11/dCAS9-SPO11 (AND2823).

Figure 6:
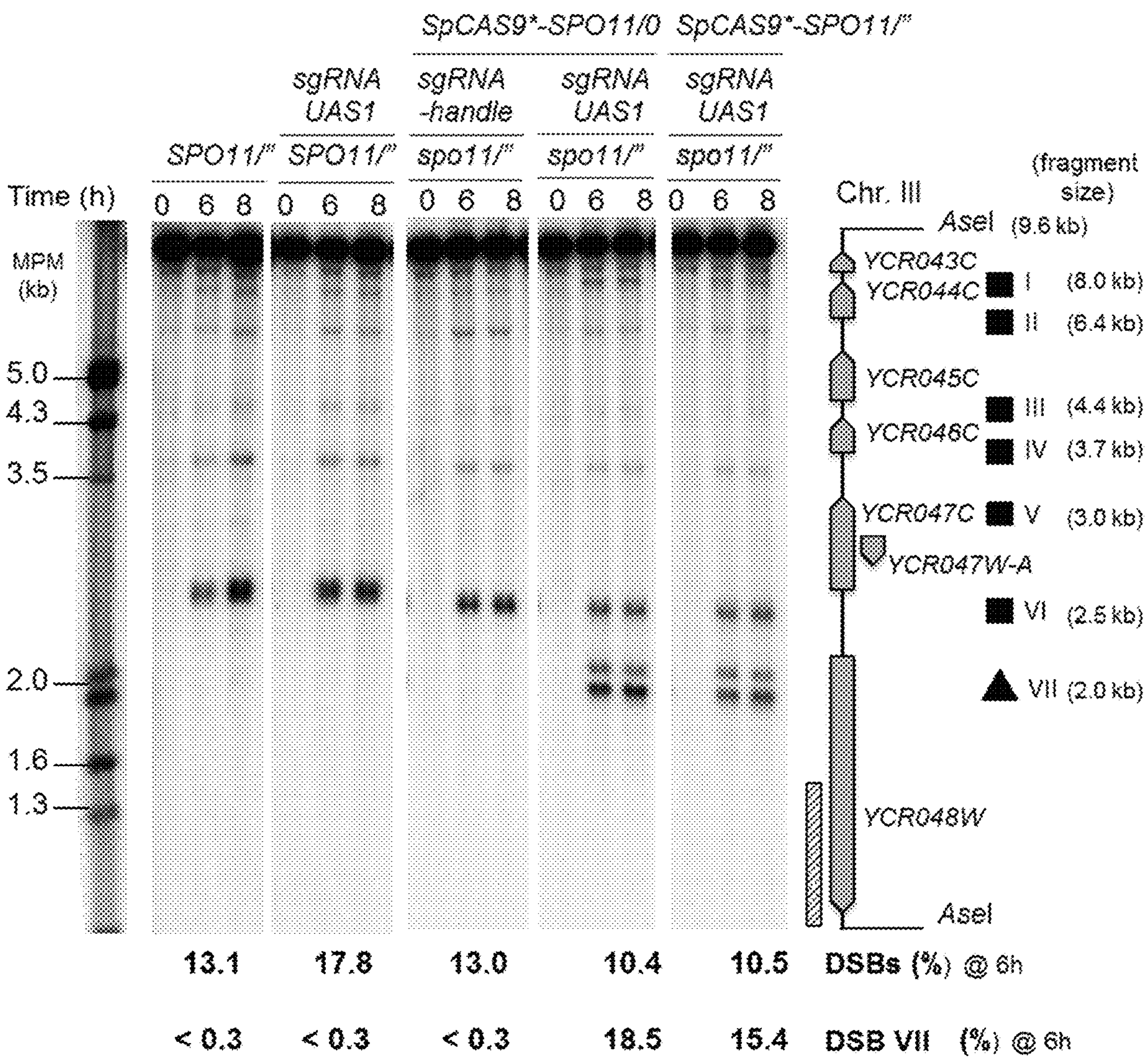

FIG. 6: Targeting of meiotic DSBs by the SpCas9*-Spo11 fusion protein and a guide RNA specific for the YCR048W region. On the right of the gel, a chart indicates the position of the genes (coding regions, gray arrows) and the position of the probe. The black squares indicate the natural DSB sites. The black triangle indicates the DSB sites targeted by the UAS1-YCR048W guide RNA. The percentage of DSBs corresponds to the ratio between the signal intensity of the fragment concerned and the total signal of the lane.

Figure 7:
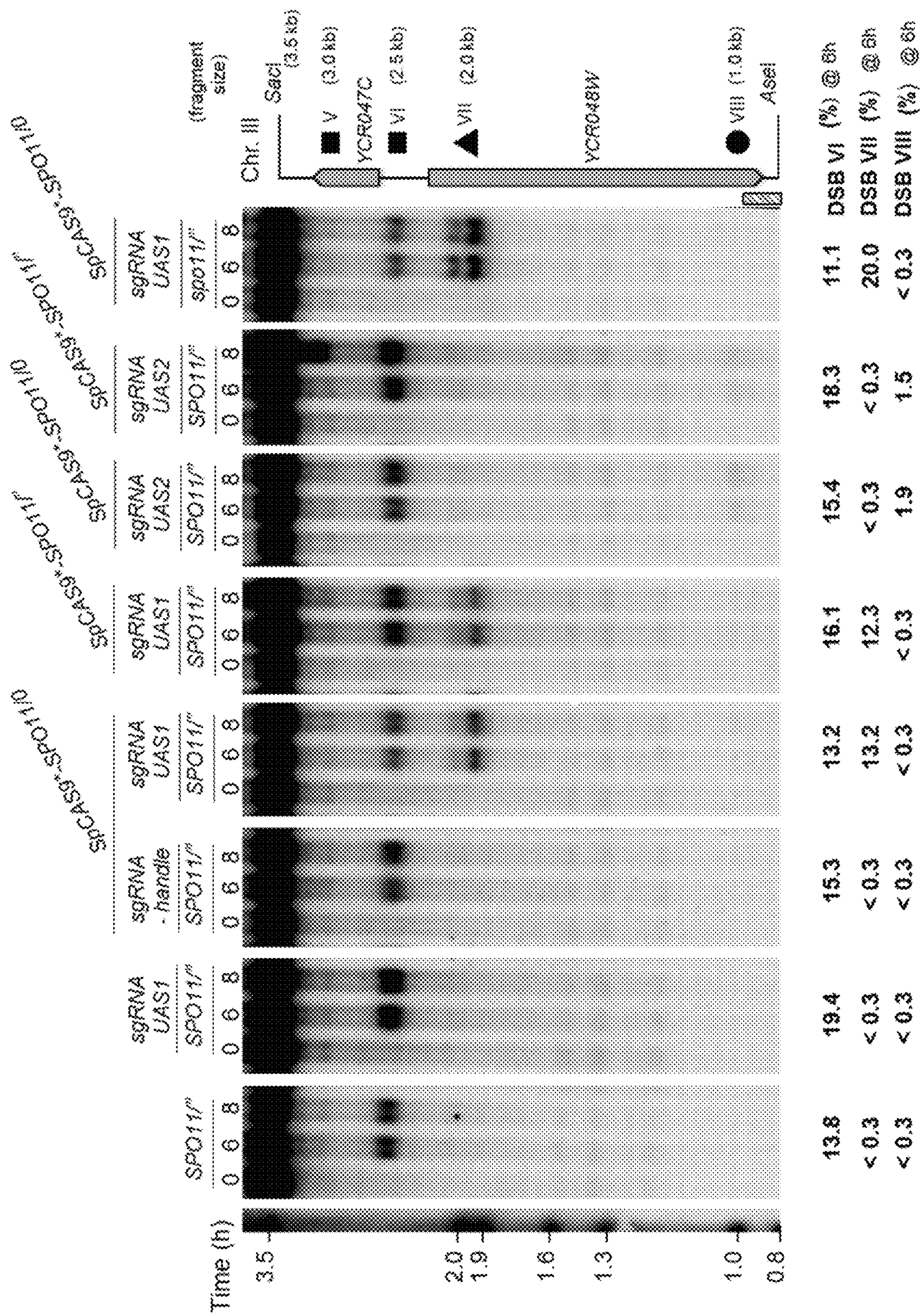

FIG. 7: Targeting of meiotic DSBs by the SpCas9*-Spo11 fusion protein and two guide RNAs specific for the YCR048W region. On the right of the gel, a chart indicates the position of the genes (coding regions, gray arrows) and the position of the probe. The black squares indicate the natural DSB sites. The black triangle indicates the DSB sites targeted by the UAS1-YCR048W guide RNA. The black circle indicates the DSB sites targeted by the UAS2-YCR048W guide RNA. The percentage of DSBs corresponds to the ratio between the signal intensity of the fragment concerned and the total signal of the lane.

Figure 8:
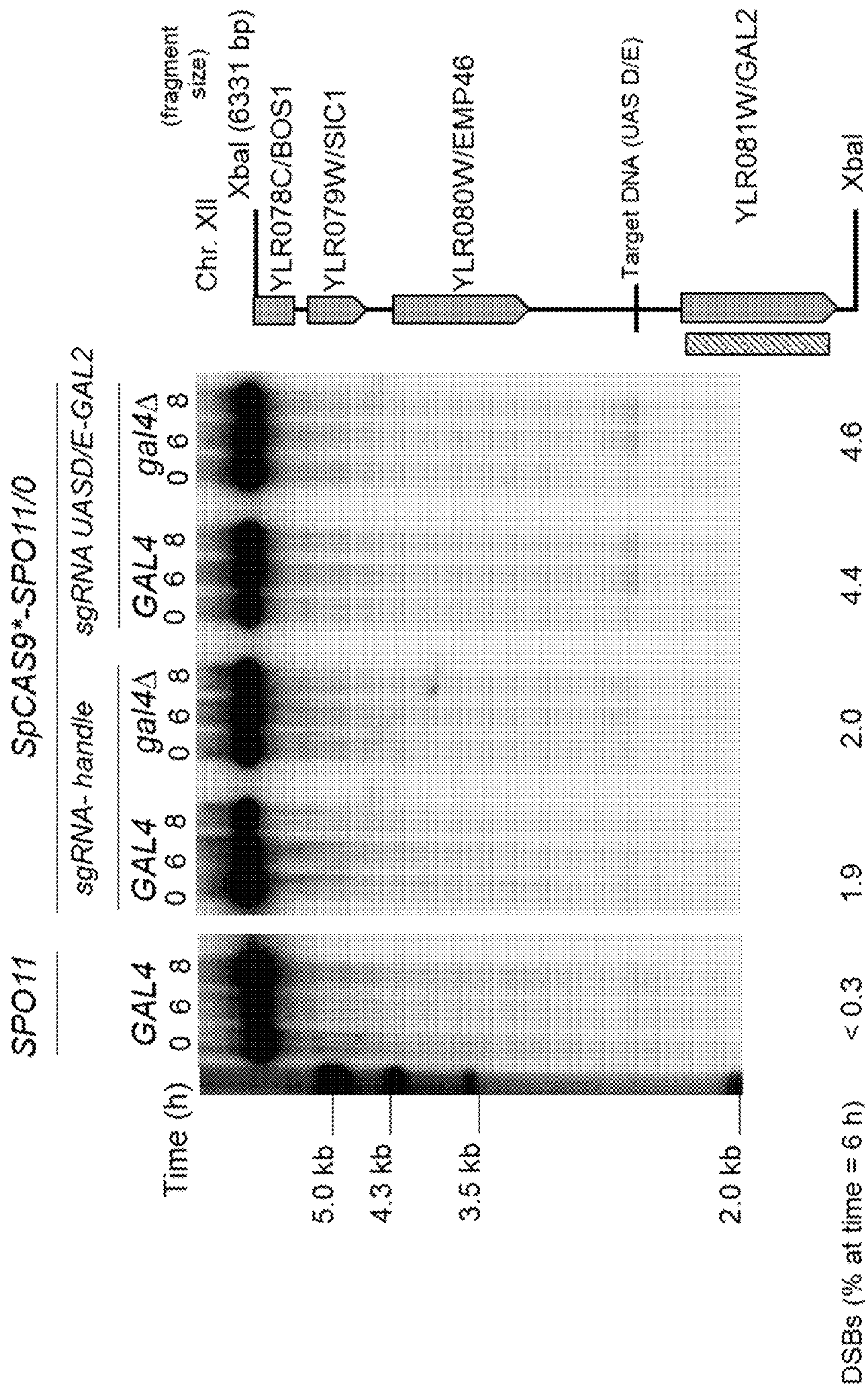

FIG. 8: Targeting of meiotic DSBs by the SpCas9*-Spo11 fusion protein and a guide RNA specific for the GAL2 region. On the right of the gel, a chart indicates the position of the genes (coding regions, gray arrows) and the position of the probe. The percentage of DSBs corresponds to the ratio between the signal intensity of the fragment concerned and the total signal of the lane.

Figure 9:
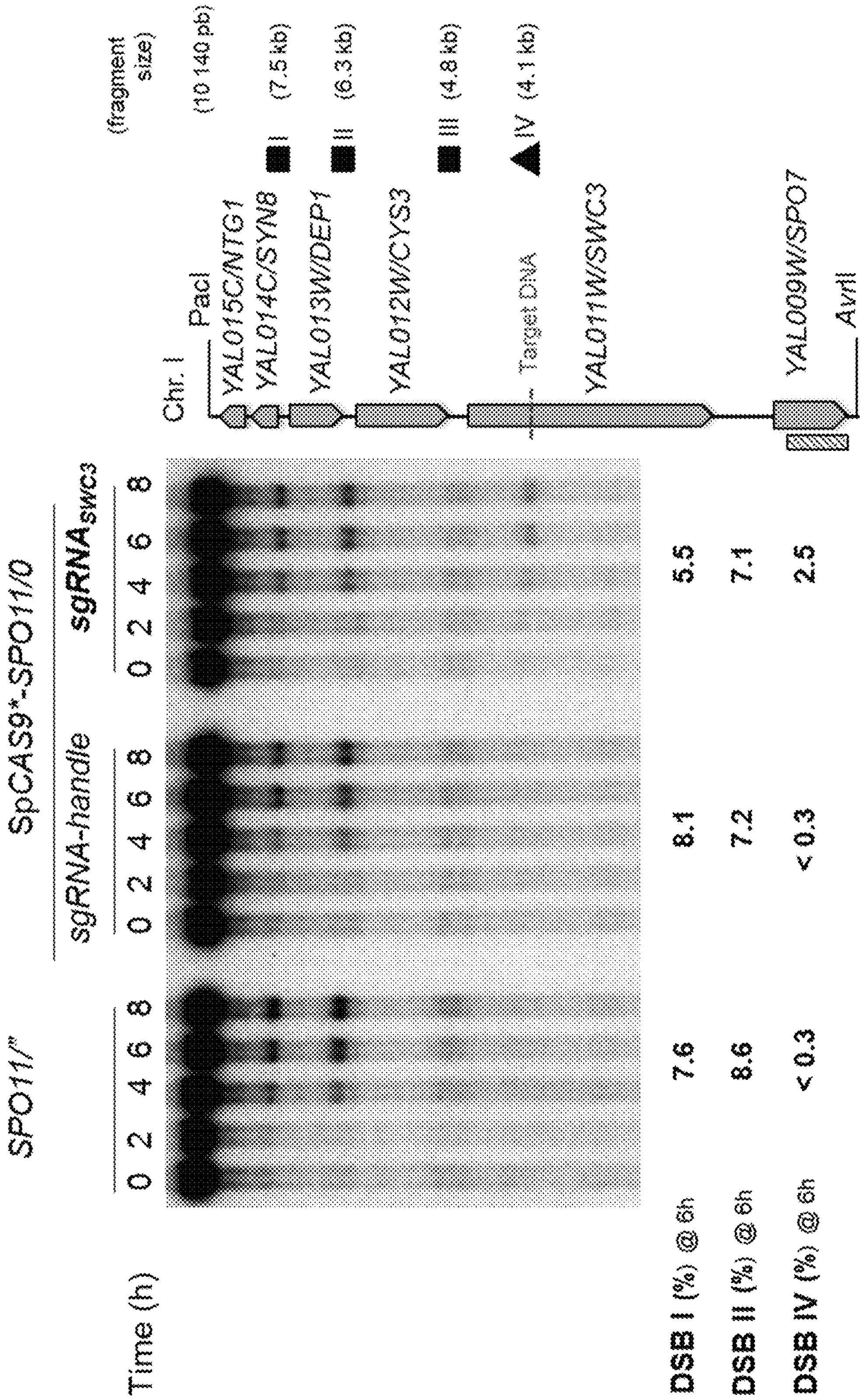

FIG. 9: Targeting of meiotic DSBs by the SpCas9*-Spo11 fusion protein and a guide RNA specific for the SWC3 region. On the right of the gel, a chart indicates the position of the genes (coding regions, gray arrows) and the position of the probe (hatched rectangle). The percentage of DSBs corresponds to the ratio between the signal intensity of the fragment concerned and the total signal of the lane.

Figure 10:
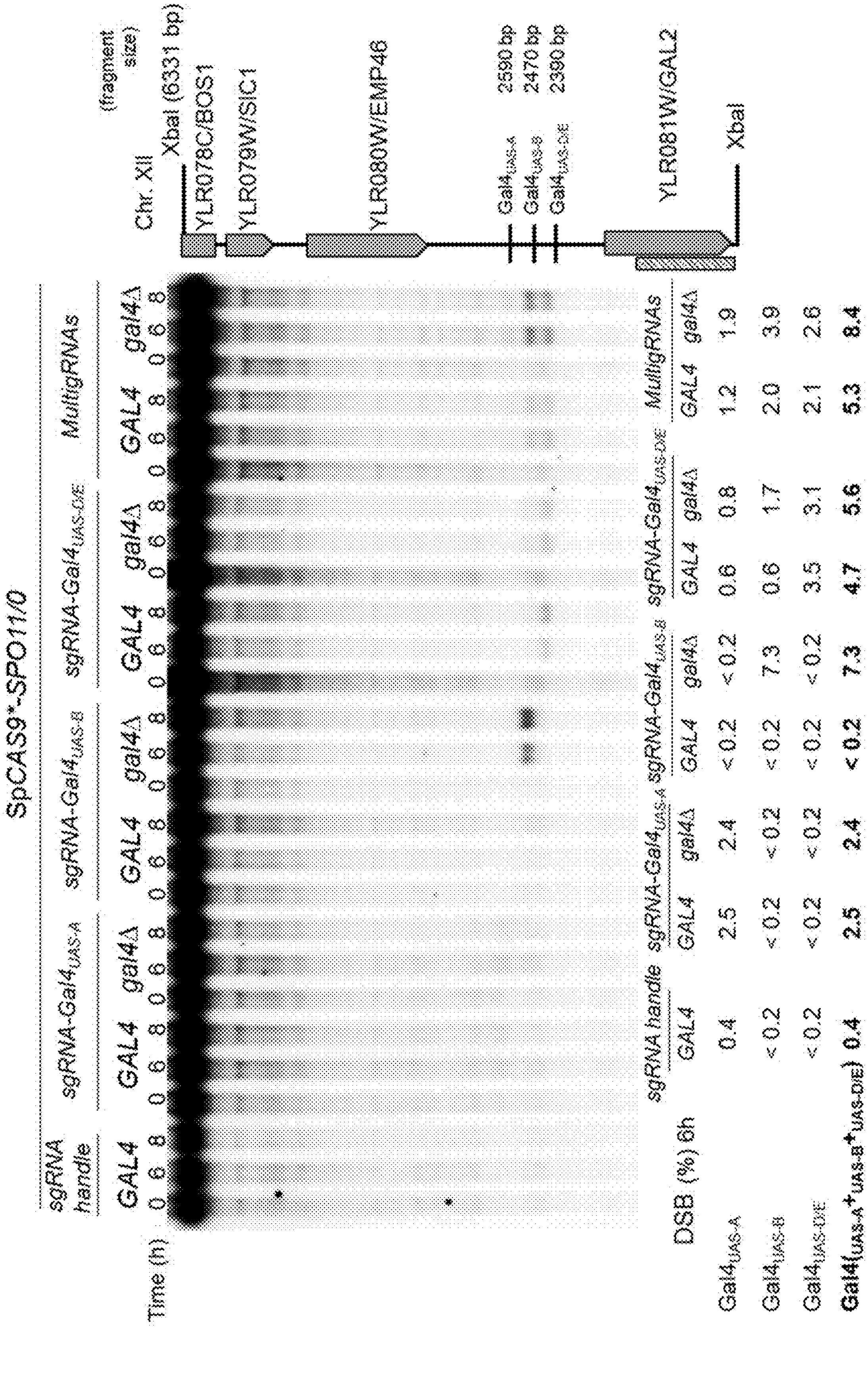

FIG. 10: Multiplexed targeting of meiotic DSBs by the SpCas9*-Spo11 fusion protein and several guide RNAs specific for the GAL2 region. On the right of the gel, a chart indicates the position of the genes (coding regions, gray arrows) and the position of the probe (hatched rectangle). The percentage of DSBs corresponds to the ratio between the signal intensity of the fragment concerned and the total signal of the lane.

Figure 11:
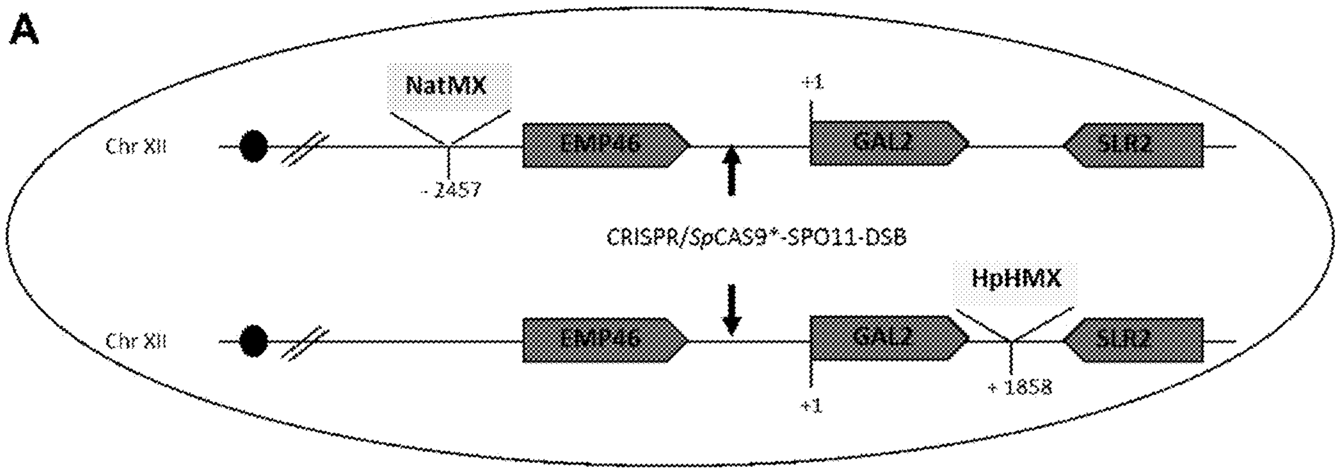

FIG. 11: Stimulation of meiotic recombination by the SpCas9*-SPO11 protein and a guide RNA in the GAL2 target region. (A) Diagram of the genetic test for detecting recombinants at the GAL2 site. (B) Test for genetic recombination at the GAL2 locus.

Figure 12:
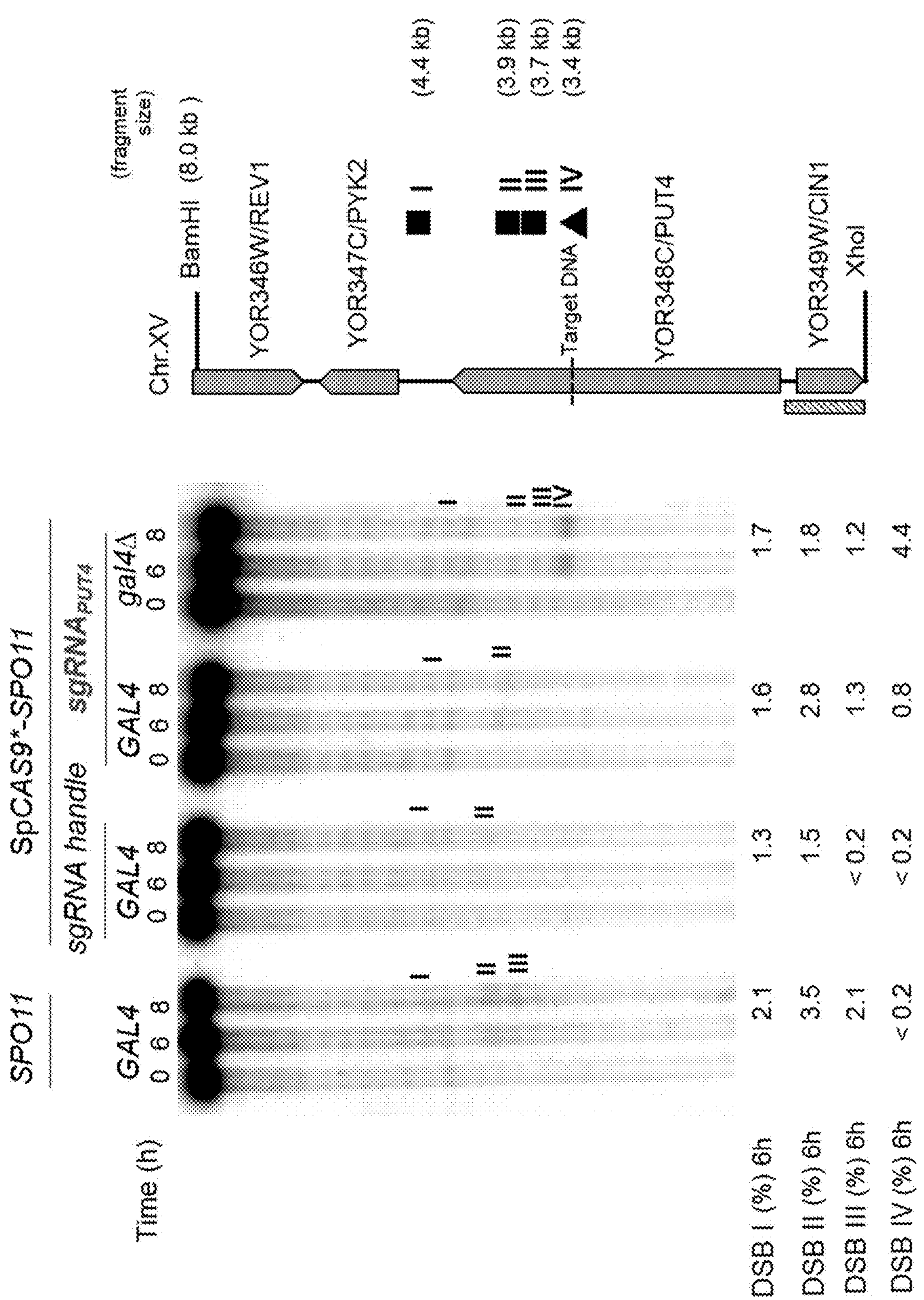

FIG. 12: Targeting of meiotic DSBs by the SpCas9*-Spo11 protein and a guide RNA specific for the PUT4 gene coding sequence. On the right of the gel, a chart indicates the position of the genes (coding regions, gray arrows) and the position of the probe (hatched rectangle). The percentage of DSBs corresponds to the ratio between the signal intensity of the fragment concerned and the total signal of the lane.

FIG. 13: Sequences of the gRNAs used. In uppercase and lowercase characters are respectively indicated the specificity-determining sequence of the gRNA (20 nucleotides in length) and the sequence constituting the structure of the gRNA ("handle", 82 nucleotides in length).

Figure 14:
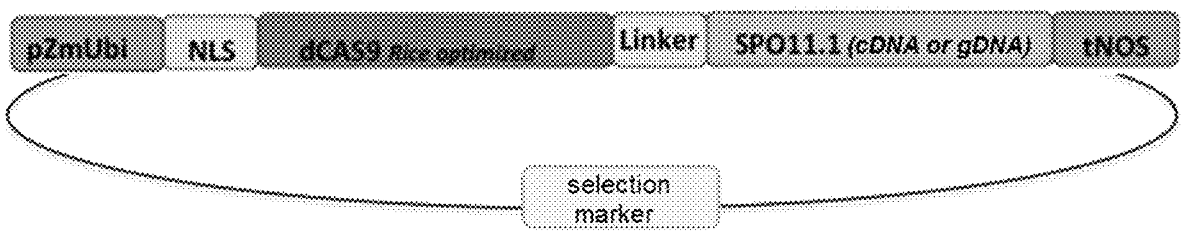

FIG. 14: Diagram of the construction for expressing the dCas9-Spo11 fusion protein in rice. pZmUbi and tNOS correspond, respectively, to the promoter and the terminator used in this construction.

DETAILED DESCRIPTION OF THE INVENTION

The Clustered Regularly Interspaced Shorts Palindromic Repeats (CRISPR)-Cas9 system is a bacterial defense system against foreign DNA. This system rests essentially on the association of a Cas9 protein and a "guide" RNA (gRNA or sgRNA) responsible for the specificity of the cleavage site. It can be used to create DNA double-strand breaks (DSBs) at the sites targeted by the CRISPR/Cas9 system. This system has already been used for targeted engineering of the genome in eukaryotic cells (see for example the patent application EP2764103), notably human cells (Cong L et al., 2013, Science 339(6121):819-823; Mali P et al., 2013, Science, 339(6121):823-826; Cho S W et al., 2013, Nature Biotechnology 31(3):230-232), rat cells (Li D, et al., 2013, Nature Biotechnology, 31(8):681-683; WO 2014/089290), mouse cells (Wang H et al., 2013, Cell, 153(4):910-918), rabbit cells (Yang D et al., 2014, Journal of Molecular Cell Biology, 6(1):97-99), frog cells (Nakayama T et al., 2013, Genesis, 51(12):835-843), fish cells (Hwang W Y et al., 2013, Nature Biotechnology, 31(3):227-229), plant cells (Shan Q et al., 2013, Nature Biotechnology, 31(8):686-688; Jiang W et al., 2013, Nucleic Acids Research, 41(20):e188), *drosophila* cells (Yu Z et al., 2013, Genetics, 195(1):289-291), nematode cells (Friedland A E et al., 2013, Nature Methods, 10(8):741-743), yeast cells (DiCarlo J, et al., 2013, Genome engineering in *Saccharomyces cerevisiae* using CRISPR-Cas systems. Nucleic Acids Research 41(7):4336-4343), but also bacterial cells (Jiang W et al., 2013, Nature Biotechnology, 31(3):233-239). On the other hand, this system has never been used to target meiotic recombination sites in any organism.

The inventors have shown that it is possible to modify the CRISPR-Cas9 system in order to induce targeted meiotic recombinations in a eukaryotic cell, and in particular in a yeast. They have in fact shown that the combined expression of a Spo11-Cas9 fusion protein and one or more guide RNAs made it possible to target the action of the transesterase Spo11 which is responsible for double-strand breaks during meiosis. Repair of these breaks by using as matrix a chromatid of the homologous chromosome induces the desired recombination phenomena.

Thus, the present invention relates to a method for inducing targeted meiotic recombinations in a eukaryotic cell comprising:

introducing into said cell:

a) a fusion protein comprising a Cas9 domain and a Spo11 domain, or a nucleic acid encoding said fusion protein; and b) one or more guide RNAs or one or more nucleic acids encoding said guide RNAs, said guide RNAs comprising an RNA structure for binding to the Cas9 domain of the fusion protein and a sequence complementary to the targeted chromosomal region; and inducing said cell to enter meiotic prophase I.

As used herein, the term "eukaryotic cell" refers to a yeast, plant, fungal or animal cell, in particular a mammalian cell such as a mouse cell or a rat cell, or an insect cell. The eukaryotic cell is preferably nonhuman and/or non-embryonic.

According to a particular embodiment, the eukaryotic cell is a yeast cell, in particular a yeast of industrial interest. Exemplary yeasts of interest include, but are not limited to, yeasts of the genus *Saccharomyces sensu stricto, Schizosaccharomyces, Yarrowia, Hansenula, Kluyveromyces, Pichia* or *Candida*, as well as the hybrids obtained from a strain belonging to one of these genera.

Preferably, the yeast of interest belongs to the genus *Saccharomyces*. It may notably belong to a species selected from the group consisting of *Saccharomyces cerevisiae, Saccharomyces bayanus, Saccharomyces castelli, Saccharomyces eubayanus, Saccharomyces kluyveri, Saccharomyces kudriavzevii, Saccharomyces mikatae, Saccharomyces uvarum, Saccharomyces paradoxus* and *Saccharomyces pastorianus* (also called *Saccharomyces carlsbergensis*), or is a hybrid obtained from a strain belonging to one of these species such as for example an *S. cerevisiae/S. paradoxus* hybrid or an *S. cerevisiae/S. uvarum* hybrid.

According to another particular embodiment, the eukaryotic cell is a fungal cell, in particular a fungal cell of industrial interest. Exemplary fungi include, but are not limited to, filamentous fungal cells. Filamentous fungi include fungi belonging to the subdivisions Eumycota and Oomycota. Filamentous fungal cells may be selected from the group consisting of *Trichoderma, Acremonium, Aspergillus, Aureobasidium, Bjerkandera, Ceriporiopsis, Chrysosporium, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium* or *Trametes* cells.

According to still another particular embodiment, the eukaryotic cell is a plant cell, in particular a plant cell of agronomic interest. Exemplary plants include, but are not limited to, rice, wheat, soy, maize, tomato, *Arabidopsis thaliana*, barley, rapeseed, cotton, sugarcane and beet. According to a preferred embodiment, the eukaryotic cell is a rice cell.

Preferably, the eukaryotic cell is heterozygous for the gene(s) targeted by the guide RNA(s).

As used herein, the term "fusion protein" refers to a chimeric protein comprising at least two domains derived from the combination of different proteins or protein fragments. The nucleic acid encoding this protein is obtained by recombination of the regions encoding the proteins or protein fragments so that they are in phase and transcribed on the same mRNA. The various domains of the fusion protein may be directly adjacent or may be separated by binding sequences (linkers) which introduce a certain structural flexibility into the construction.

The fusion protein used in the present invention comprises a Cas9 domain and a Spo11 domain.

The Cas9 domain is the domain of the fusion protein that is able to interact with the guide RNAs and to target the nuclease activity of the Spo11 domain toward a given chromosomal region. The Cas9 domain can consist of a Cas9 protein (also called Csn1 or Csx12), wildtype or modified, or a fragment of this protein capable of interacting with the guide RNAs. The Cas9 protein can notably be modified in order to modulate its enzymatic activity. Thus, the nuclease activity of the Cas9 protein can be modified or inactivated. The Cas9 protein can also be truncated to remove the protein domains not essential to the functions of the fusion protein, in particular the Cas9 protein domains that are not necessary to interaction with the guide RNAs.

The Cas9 protein or fragment thereof as used in the present invention can be obtained from any known Cas9 protein (Makarova et al., 2008, Nat. Rev. Microbiol., 9, pp. 466-477). Exemplary Cas9 proteins that can be used in the present invention include, but are not limited to, the Cas9 proteins from *Streptococcus pyogenes, Streptococcus thermophilus, Streptococcus* sp., *Nocardiopsis dassonvillei, Streptomyces pristinaespiralis, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicellulosiruptor bescii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsonii, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, or *Acaryochloris marina*. Other Cas9 proteins that can be used in the present invention are also described in the article by Makarova et al. (Makarova et al., 2008, Nat. Rev. Microbiol., 9, pp. 466-477). Preferably, the Cas9 domain comprises, or consists of, the Cas9 protein from *Streptococcus pyogenes* (NCBI entry number: WP_010922251.1, SEQ ID NO: 8) or a fragment thereof capable of interacting with the guide RNAs.

According to a particular embodiment, the Cas9 domain consists of a whole Cas9 protein, preferably the Cas9 protein from *Streptococcus pyogenes.*

Generally, Cas9 proteins comprise two nuclease domains: a domain related to a RuvC domain and a domain related to an HNH domain. These two domains cooperate to create DNA double-strand breaks (Jinek et al., Science, 337: 816-821). Each of these nuclease domains can be inactivated by deletion, insertion or substitution according to techniques well-known to a person skilled in the art such as directed mutagenesis, PCR mutagenesis or total gene synthesis. Thus, the RuvC domain can be inactivated for example by the substitution D10A and the HNH domain can be inactivated for example by the substitution H840A (Jinek et al., Science, 337: 816-821), the indicated positions being those of SEQ ID NO: 8.

In the peptide sequences described in this document, the amino acids are represented by their one-letter code according to the following nomenclature: C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan and Y: tyrosine.

According to an embodiment, the Cas9 domain is deficient in at least one nuclease activity. This domain can be obtained by inactivating at least one nuclease domain of the Cas9 protein as described above.

According to a particular embodiment, the Cas9 domain comprises, or consists of, a Cas9 protein or a Cas9 protein fragment, lacking nuclease activity (also called Cas9* or dCas9). This catalytically-inactive form can be obtained by inactivating the two nuclease domains of the Cas9 protein as mentioned above, for example by introducing the two point mutations substituting the aspartate at position 10 and the histidine at position 840 by alanines.

According to a preferred embodiment, the Cas9 domain comprises, or consists of, a Cas9 protein, preferably the Cas9 protein from *Streptococcus pyogenes* (spCas9), lacking nuclease activity (spCas9*).

According to a particular embodiment, the Cas9 domain comprises, or consists of, the sequence presented in SEQ ID NO: 8 wherein the aspartate at position 10 and the histidine at position 840 have been substituted by alanines.

Spo11 is a protein related to the catalytic A subunit of a type II topoisomerase present in archaebacteria (Bergerat et al., Nature, vol. 386, pp 414-7). It catalyzes the DNA double-strand breaks initiating meiotic recombinations. It is a highly conserved protein for which homologs exist in all eukaryotes. Spo11 is active as a dimer formed of two subunits, each of which cleaves a DNA strand. Although essential, Spo11 does not act alone to generate double-strand breaks during meiosis. In the yeast *S. cerevisiae*, for example, it cooperates with Rec102, Rec103/Sk18, Rec104, Rec114, Mer1, Mer2/Rec107, Mei4, Mre2/Nam8, Mre11, Rad50, Xrs2/Nbs1, Hop1, Red1, Mek1, Set1 and Spp1 proteins and with other partners described in the articles by Keeney et al. (2001 Curr. Top. Dev. Biol, 52, pp. 1-53), Smith et al. (Curr. Opin. Genet. Dev, 1998, 8, pp. 200-211) and Acquaviva et al. (2013 Science, 339, pp. 215-8). It was recently shown, however, that targeting Spo11 to a given site is sufficient to initiate the meiotic recombination process (Peciña et al., 2002 Cell, 111, 173-184). It should be noted that several Spo11 protein homologs can coexist in the same cell, notably in plants. Preferably, the Spo11 protein is one of the Spo11 proteins of the eukaryotic cell of interest.

The Spo11 domain of the Cas9-Spo11 fusion protein is generally the domain responsible for double-strand breaks. This domain may consist of a Spo11 protein or fragment thereof capable of inducing DNA double-strand breaks.

The Spo11 protein or fragment thereof as used in the present invention can be obtained from any known Spo11 protein such as the Spo11 protein from *Saccharomyces cerevisiae* (Gene ID: 856364, NCBI entry number: NP_011841 (SEQ ID NO: 9) Esposito and Esposito, Genetics, 1969, 61, pp. 79-89), the AtSpo11-1 and AtSpo11-2 proteins from *Arabidopsis thaliana* (Grelon M. et al., 2001, Embo J., 20, pp. 589-600), the mSpo11 murine protein (Baudat F et al., Molecular Cell, 2000, 6, pp. 989-998), the Spo11 protein from *C. elegans* or the Spo11 protein from *drosophila* meiW68 (McKim et al., 1998, Genes Dev, 12(18), pp. 2932-42). Of course, these examples are non-limiting and any known Spo11 protein can be used in the method according to the invention.

According to a preferred embodiment, the Spo11 domain comprises, or consists of, a Spo11 protein, preferably a Spo11 protein from *Saccharomyces cerevisiae*, such as for example the protein having the sequence SEQ ID NO: 9.

According to a particular embodiment, the Spo11 domain is nuclease-deficient. In particular, the Spo11 domain may comprise, or consist of, the Spo11-Y135F mutant protein, a mutant protein incapable of inducing DNA double-strand breaks (Neale M J, 2002, Molecular Cell, 9, 835-846). The position indicated is that of SEQ ID NO: 9.

The ability of the fusion protein according to the invention to induce DNA double-strand breaks may come from the Cas9 domain or from the Spo11 domain. Thus, the fusion protein comprises at least one domain, Cas9 or Spo11, having nuclease activity, preferably the Spo11 domain.

According to a particular embodiment, several fusion proteins according to the invention comprising various Spo11 domains can be introduced into the same cell. In particular, when several Spo11 homologs exist in the eukaryotic cell of interest, the various fusion proteins may each comprise a different Spo11 homolog. By way of example, two fusion proteins according to the invention comprising respectively the Spo11-1 and Spo11-2 domains of *Arabidopsis thaliana* may be introduced into the same cell, preferably into the same *Arabidopsis thaliana* cell. Still by way of example, one or more fusion proteins according to the invention comprising the Spo11-1, Spo11-2, Spo11-3 and/or Spo11-4 domains of rice may be introduced into the same cell, preferably into the same rice cell. Numerous Spo11 homologs have been identified in various species, in particular in plant species (Sprink T and Hartung F, Frontiers in Plant Science, 2014, Vol. 5, article 214, doi: 10.3389/fpls.2014.00214; Shingu Y et al., BMC Mol Biol, 2012, doi: 10.1186/1471-2199-13-1). A person skilled in the art can readily identify the Spo11 homologs in a given species, notably by means of well-known bioinformatics techniques.

The fusion protein according to the invention comprises a Spo11 domain and a Cas9 domain as defined above.

According to an embodiment, the Spo11 domain is on the N-terminal side and the Cas9 domain is on the C-terminal side of the fusion protein. According to another embodiment, the Spo11 domain is on the C-terminal side and the Cas9 domain is on the N-terminal side of the fusion protein.

The fusion protein may also comprise a nuclear localization signal (NLS) sequence. NLS sequences are well-known to a person skilled in the art and in general comprise a short sequence of basic amino acids. By way of example, the NLS sequence may comprise the sequence PKKKRKV (SEQ ID NO: 3). The NLS sequence may be present at the N-terminal end, at the C-terminal end, or in an internal region of the fusion protein, preferably at the N-terminal end of the fusion protein.

The fusion protein may also comprise an additional cell-penetrating domain, i.e., a domain facilitating the entry of the fusion protein into the cell. This type of domain is well-known to a person skilled in the art and may comprise for example a penetrating peptide sequence derived from the HIV-1 TAT protein such as GRKKRRQRRRPPQPKKKRKV (SEQ ID NO: 4), derived from the TLM sequence of the human hepatitis B virus such as PLSSIFSRIGDPPKKKRKV (SEQ ID NO: 5), or a polyarginine peptide sequence. This cell penetrating domain may be present at the N-terminal end or at the C-terminal end or may be inside the fusion protein, preferably at the N-terminal end.

The fusion protein may further comprise one or more binding sequences (linkers) between the Cas9 and Spo11 domains, and optionally between these domains and the other domains of the protein such as the nuclear localization signal sequence or the cell-penetrating domain. The length of these linkers is readily adjustable by a person skilled in the art. In general, these sequences comprise between 10 and 20 amino acids, preferably about 15 amino acids and more preferably 12 amino acids. The linkers between the various domains may be of identical or different lengths.

According to a particular embodiment, the fusion protein comprises, or consists of, successively, from the N-terminal end to the C-terminal end: a nuclear localization signal, a first linker (linker1), a Cas9 domain, a second linker (linker2) and a Spo11 domain.

According to another particular embodiment, the fusion protein comprises, or consists of, successively, from the N-terminal end to the C-terminal end: a nuclear localization signal, a first linker (linker1), a Spo11 domain, a second linker (linker2) and a Cas9 domain.

The fusion protein may further comprise a tag that is a defined amino acid sequence. This tag may notably be used to detect the expression of the fusion protein, to identify the proteins interacting with the fusion protein or to characterize the binding sites of the fusion protein in the genome. The detection of the tag attached to the fusion protein may be carried out with an antibody specific for said tag or by means of any other technique well-known to a person skilled in the art. The identification of the proteins interacting with the fusion protein may be carried out, for example, by co-immunoprecipitation techniques. The characterization of the binding sites of the fusion protein in the genome may be carried out, for example, by immunoprecipitation, chromatin immunoprecipitation coupled with realtime quantitative PCR (ChIP-qPCR), chromatin immunoprecipitation coupled with sequencing techniques (ChIP-Seq), cartography using oligonucleotide (oligo) mapping or any other technique well-known to a person skilled in the art.

This tag may be present at the N-terminal end of the fusion protein, at the C-terminal end of the fusion protein, or at a nonterminal position in the fusion protein. Preferably, the tag is present at the C-terminal end of the fusion protein. The fusion protein may comprise one or more tags, which may be identical or different.

The tags, as used in the present invention, may be selected from the many tags well-known to a person skilled in the art. In particular, the tags used in the present invention may be peptide tags and/or protein tags. Preferably, the tags used in the present invention are peptide tags. Exemplary peptide tags that can be used in the present invention include, but are not limited to, tags consisting of repeats of at least six histidines (His), in particular tags consisting of six or eight histidines, as well as Flag, polyglutamate, hemagglutinin (HA), calmodulin, Strep, E-tag, myc, V5, Xpress, VSV, S-tag, Avi, SBP, Softag 1, Softag 2, Softag 3, isopetag, SpyTag and tetracysteine tags and combinations thereof. Exemplary protein tags that can be used in the present invention include, but are not limited to, glutathione S-transferase (GST), *Staphylococcus aureus* protein A, Nus A, chitin-binding protein (CBP), thioredoxin, maltose binding protein (MBP), biotin carboxyl carrier protein (BCCP), and immunoglobulin constant fragment (Fc) tags, tags comprising a fluorescent protein such as green fluorescent protein (GFP), red fluorescent protein (RFP), cyan fluorescent protein (CFP) or yellow fluorescent protein (YFP), and combinations thereof.

According to a preferred embodiment, the fusion protein comprises a tag consisting of six histidines and/or one or more Flag motifs, preferably three Flag motifs. According to a particular embodiment, the fusion protein comprises a tag consisting of six histidines and three Flag motifs.

Alternatively, the Spo11 domain of the Cas9-Spo11 fusion protein may be replaced by one of the Spo11 partners capable of recruiting Spo11, i.e., a protein that forms a complex with Spo11 and thus induces the formation of double-strand breaks. This partner may be selected from the proteins cited in the articles by Keeney et al. (2001 Curr. Top. Dev. Biol, 52, pp. 1-53), Smith et al. (Curr. Opin. Genet. Dev, 1998, 8, pp. 200-211) and Acquaviva et al. (2013 Science, 339, pp. 215-8), and more particularly from the group consisting of Rec102, Rec103/Sk18, Rec104, Rec114, Mer1, Mer2/Rec107, Mei4, Mre2/Nam8, Mre11, Rad50, Xrs2/Nbs1, Hop1, Red1, Mek1, Set1 and Spp1. Preferably, the partner replacing the Spo11 domain is Mei4 or Spp1.

All the embodiments described for the Cas9-Spo11 fusion protein also apply to fusion proteins wherein the Spo11 domain is replaced by one of its partners.

The fusion protein as described above may be introduced into the cell in protein form, notably in mature form or in precursor form, preferably in mature form, or in the form of a nucleic acid encoding said protein.

When the fusion protein is introduced into the cell in protein form, protecting groups may be added at the C- and/or N-terminal ends in order to improve the fusion protein's resistance to peptidases. For example, the protecting group at the N-terminal end may be an acylation or an acetylation and the protecting group at the C-terminal end may be an amidation or an esterification. The action of the proteases may also be thwarted by the use of amino acids having the D-configuration, the cyclization of the protein by formation of disulfide bridges, lactam rings or bonds between the N- and C-terminal ends. The fusion protein of the invention may also comprise pseudopeptide bonds replacing the "conventional" peptide bonds (CONH) and conferring increased resistance to peptidases, such as $CHOH—CH_2$, NHCO, $CH_2—O$, $CH_2CH_2$, $CO—CH_2$, N—N, CH═CH, $CH_2NH$, and $CH_2—S$. The fusion protein may also comprise one or more amino acids that are rare amino acids, notably hydroxyproline, hydroxylysine, allo-hydroxylysine, 6-N-methylysine, N-ethylglycine, N-methylglycine, N-ethylasparagine, alloisoleucine, N-methylisoleucine, N-methylvaline, pyroglutamine, aminobutyric acid; or synthetic amino acids notably ornithine, norleucine, norvaline and cyclohexylalanine.

The fusion protein according to the invention can be obtained by conventional chemical synthesis (solid-phase or homogeneous liquid-phase) or by enzymatic synthesis (Kullmann W, Enzymatic peptide synthesis, 1987, CRC Press, Florida). It may also be obtained by a method consisting in growing a host cell expressing a nucleic acid encoding the fusion protein and recovering said protein from these cells or from the culture medium.

As used in the present application, the term "guide RNA" or "gRNA" refers to an RNA molecule capable of interacting with the Cas9 domain of the fusion protein in order to guide it toward a target chromosomal region.

Each gRNA comprises two regions:

- a first region (commonly called the "SDS" region), at the 5' end of the gRNA, which is complementary to the target chromosomal region and which imitates the crRNA of the endogenous CRISPR system, and
- a second region (commonly called the "handle" region), at the 3' end of the gRNA, which mimics the base-pair interactions between the transactivating crRNA (tracrRNA) and the crRNA of the endogenous CRISPR system and has a stem-loop double-stranded structure ending in the 3' direction with an essentially single-stranded sequence. This second region is essential to binding of the gRNA to the Cas9 domain of the fusion protein.

The first region of the gRNA varies according to the targeted chromosomal sequence. On the other hand, the handle regions of the various gRNAs used may be identical or different. According to a particular embodiment, the handle region comprises, or consists of, the 3' 82-nucleotide sequence of the sequences SEQ ID NO: 10 to 16 (sequence in lowercase in FIG. 13).

The SDS region of the gRNA, which is complementary to the target chromosomal region, generally comprises between 10 and 25 nucleotides. Preferably, this region has a length of 19, 20 or 21 nucleotides, and particularly preferably 20 nucleotides.

The second region of the gRNA has a stem-loop (or hairpin) structure. The lengths of the stem and the loop may vary. Preferably, the loop has a length of 3 to 10 nucleotides and the stem a length of 6 to 20 nucleotides. The stem may optionally have mismatched regions (forming "bulges") of 1 to 10 nucleotides. Preferably, the total length of this handle region is 50 to 100 nucleotides, and more particularly preferably 82 nucleotides.

The total length of a gRNA is generally 50 to 140 nucleotides, preferably 80 to 125 nucleotides, and more particularly preferably 90 to 110 nucleotides. According to a particular embodiment, a gRNA as used in the present invention has a length of 102 nucleotides.

The gRNA is preferably formed of a single RNA molecule comprising the two domains. Alternatively, the gRNA may be formed of two distinct RNA molecules, the first molecule comprising the SDS region and half of the stem of the second region, and the second molecule comprising the second half of the stem of the gRNA. Thus, the pairing of the two RNA molecules by their complementary sequences at the stem, forms a functional gRNA.

A person skilled in the art can, by using well-known techniques, readily define the sequence and the structure of the gRNAs according to the chromosomal region to be targeted (see for example the article by Di Carlo et al., Nucleic Acids Research 2013, 1-8).

In the method according to the invention, one or more gRNAs can be used simultaneously. These different gRNAs may target identical or different chromosomal regions, preferably different.

The gRNAs can be introduced into the eukaryotic cell as mature gRNA molecules, as precursors, or as one or more nucleic acids encoding said gRNAs.

When the gRNA(s) are introduced into the cell directly as RNA molecules (mature or precursors), these gRNAs may contain modified nucleotides or chemical modifications allowing them, for example, to increase their resistance to nucleases and thus to increase their lifespan in the cell. They may notably include at least one modified or non-natural nucleotide such as, for example, a nucleotide comprising a modified base, such as inosine, methyl-5-deoxycytidine, dimethylamino-5-deoxyuridine, deoxyuridine, diamino-2,6-purine, bromo-5-deoxyuridine or any other modified base allowing hybridization. The gRNAs used according to the invention may also be modified at the internucleotide bond such as for example phosphorothioates, H-phosphonates or alkylphosphonates, or at the backbone such as for example alpha oligonucleotides, 2'-O-alkyl-riboses or peptide nucleic acid (PNA) (Egholm et al., 1992 J. Am. Chem. Soc., 114, 1895-1897).

The gRNAs may be natural RNA, synthetic RNA, or RNA produced by recombination techniques. These gRNAs may be prepared by any methods known to a person skilled in the art such as, for example, chemical synthesis, in vivo transcription or amplification techniques.

According to an embodiment, the method comprises introducing into the eukaryotic cell the fusion protein and one or more gRNAs capable of targeting the action of the fusion protein toward a given chromosomal region. The protein and the gRNAs may be introduced into the cytoplasm or the nucleus of the eukaryotic cell by any method known to a person skilled in the art, for example by microinjection. The fusion protein may notably be introduced into the cell as an element of a protein-RNA complex comprising at least one gRNA.

According to another embodiment, the method comprises introducing into the eukaryotic cell the fusion protein and one or more nucleic acids encoding one or more gRNAs.

According to still another embodiment, the method comprises introducing into the eukaryotic cell a nucleic acid encoding the fusion protein and one or more gRNAs.

According to still another embodiment, the method comprises introducing into the eukaryotic cell a nucleic acid encoding the fusion protein and one or more nucleic acids encoding one or more gRNAs.

The fusion protein, or the nucleic acid encoding said fusion protein, and the gRNA(s), or the nucleic acid(s) encoding said gRNA(s), may be introduced into the cell simultaneously or sequentially.

Alternatively, and more particularly concerning plant cells, the nucleic acid encoding the fusion protein and the nucleic acid(s) encoding the gRNA(s) may be introduced into a cell by crossing two cells into which have been respectively introduced the nucleic acid encoding the fusion protein and the nucleic acid(s) encoding the gRNA(s).

Alternatively, and more particularly concerning plant cells, the nucleic acid encoding the fusion protein and the nucleic acid(s) encoding the gRNA(s) may be introduced into a cell by mitosis of a cell into which the nucleic acid encoding the fusion protein and the nucleic acid(s) encoding the gRNA(s) have been previously introduced.

In the embodiments where the fusion protein and/or the gRNA(s) are introduced into the eukaryotic cell as a nucleic acid encoding said protein and/or said gRNA(s), the expression of said nucleic acids makes it possible to produce the fusion protein and/or the gRNA(s) in the cell.

In the context of the invention, by "nucleic acid" is meant any molecule based on DNA or RNA. These molecules may be synthetic or semisynthetic, recombinant, optionally amplified or cloned into vectors, chemically modified, comprising non-natural bases or modified nucleotides comprising for example a modified bond, a modified purine or pyrimidine base, or a modified sugar. Preferably, the use of codons is optimized according to the nature of the eukaryotic cell.

The nucleic acids encoding the fusion protein and those encoding the gRNAs may be placed under the control of identical or different promoters, which may be constitutive or inducible, in particular meiosis-specific promoters. According to a preferred embodiment, the nucleic acids are placed under the control of constitutive promoters such as the ADH1 promoter or the RNA polymerase III-dependent pRPR1 and SNR52 promoters, more preferably the pRPR1 promoter.

The nature of the promoter may also depend on the nature of the eukaryotic cell. According to a particular embodiment, the eukaryotic cell is a plant cell, preferably a rice cell, and the nucleic acids are placed under the control of a promoter selected from the maize ubiquitin promoters (pZmUbi) and the polymerase III U3 and U6 promoters. According to a preferred embodiment, the nucleic acid encoding the fusion protein is placed under the control of the promoter pZmUbi and the nucleic acids encoding the gRNAs are placed under the control of the U3 or U6 promoter, preferably the U3 promoter.

The nucleic acids encoding the fusion protein and the gRNA(s) may be disposed on the same construction, in particular on the same expression vector, or on distinct constructions. Alternatively, the nucleic acids may be inserted into the genome of the eukaryotic cell in identical or distinct regions. According to a preferred embodiment, the nucleic acids encoding the fusion protein and the gRNA(s) are disposed on the same expression vector.

The nucleic acids as described above may be introduced into the eukaryotic cell by any method known to a person skilled in the art, in particular by microinjection, transfection, electroporation and biolistics.

Optionally, the expression or the activity of the endogenous Spo11 protein of the eukaryotic cell may be suppressed in order to better control meiotic recombination phenomena. This inactivation may be carried out by techniques well-known to a person skilled in the art, notably by inactivating the gene encoding the endogenous Spo11 protein or by inhibiting its expression by means of interfering RNA.

After introducing into the eukaryotic cell the fusion protein and one or more gRNAs, or nucleic acids encoding same, the method according to the invention comprises inducing said cell to enter meiotic prophase I.

This induction may be done according to various methods, well-known to a person skilled in the art.

By way of example, when the eukaryotic cell is a mouse cell, the cells may be induced to enter meiotic prophase I by adding retinoic acid (Bowles J et al., 2006, Science, 312 (5773), pp. 596-600).

When the eukaryotic cell is a plant cell, the induction of meiosis is carried out according to a natural process. According to a particular embodiment, after transforming a callus comprising one or more plant cells, a plant is regenerated and placed in conditions promoting the induction of a reproductive phase and thus of the meiotic process. These conditions are well-known to a person skilled in the art.

When the eukaryotic cell is a yeast, this induction may be carried out by transferring the yeast to sporulation medium, in particular from rich medium to sporulation medium, said sporulation medium preferably lacking a fermentable carbon source or a nitrogen source, and incubating the yeasts in the sporulation medium for a sufficient period of time to induce Spo11 dependent double-strand breaks. The initiation of the meiotic cycle depends on several signals: the presence of the two mating type alleles MATa and MATα, the absence of a nitrogen source and a fermentable carbon source.

As used in this document, the term "rich medium" refers to a culture medium comprising a fermentable carbon source and a nitrogen source as well as all the nutritive elements necessary for yeasts to multiply by mitotic division. This medium can be readily selected by a person skilled in the art and may, for example, be selected from the group consisting of YPD medium (1% yeast extract, 2% bactopeptone and 2% glucose), YPG medium (1% yeast extract, 2% bactopeptone and 3% glycerol) and synthetic complete (SC) medium (Treco and Lundblad, 2001, Curr. Protocol. Mol. Biol., Chapter 13, Unit 13.1).

As used in this document, the term "sporulation medium" refers to any medium that induces yeast cells to enter meiotic prophase without vegetative growth, in particular a culture medium not comprising a fermentable carbon source or a nitrogen source but comprising a carbon source that can be metabolized by respiration, such as acetate. This medium can be readily selected by a person skilled in the art and may, for example, be selected from the group consisting of 1% KAc medium (Wu and Lichten, 1994, Science, 263, pp. 515-518), SPM medium (Kassir and Simchen, 1991, Meth. Enzymol., 194, 94-110) and the sporulation media described in the article by Sherman (Sherman, Meth. Enzymol., 1991, 194, 3-21).

According to a preferred embodiment, before being incubated in the sporulation medium, the cells are grown for a few rounds of division in a pre-sporulation medium so as to obtain effective and synchronous sporulation. The pre-sporulation medium can be readily selected by a person skilled in the art. For example, this medium may be SPS medium (Wu and Lichten, 1994, Science, 263, pp. 515-518).

The choice of media (rich medium, pre-sporulation medium, sporulation medium) depends on the physiological and genetic characteristics of the yeast strain, notably if this strain is auxotrophic for one or more compounds.

Once the cell is engaged in meiotic prophase I, the meiotic process may continue until four daughter cells having the required recombinations are produced.

Alternatively, when the eukaryotic cell is a yeast, and in particular a yeast of the genus *Saccharomyces*, the cells can be returned to growth conditions in order to resume a mitotic process. This phenomenon, called "return-to-growth" or "RTG", was previously described in the patent application WO 2014/083142 and occurs when cells that have entered meiosis in response to a nutritional deficiency are placed in the presence of a carbon and nitrogen source after the formation of Spo11-dependent double-strand breaks but before the first meiotic division (Honigberg and Esposito, Proc. Nat. Acad. Sci USA, 1994, 91, 6559-6563). Under these conditions, they stop progressing through the stages of meiotic differentiation to resume a mitotic growth mode while inducing the desired recombinations during repair of the double strand breaks caused by Spo11 (Sherman and Roman, Genetics, 1963, 48, 255-261; Esposito and Esposito, Proc. Nat. Acad. Sci, 1974, 71, pp. 3172-3176; Zenvirth et al., Genes to Cells, 1997, 2, pp. 487-498).

The method may further comprise obtaining a cell or cells having the desired recombination(s).

The method according to the invention can be used in all applications where it is desirable to improve and control meiotic recombination phenomena. In particular, the invention makes it possible to associate, preferentially, genetic traits of interest. This preferential association makes it possible, on the one hand, to reduce the time necessary to select them and, on the other hand, to generate possible but improbable natural combinations. Lastly, according to the embodiment selected, the organisms obtained by this method may be regarded as non-genetically modified organisms (non-GMO).

According to another aspect, the present invention relates to a method for generating variants of a eukaryotic organism, with the exception of humans, preferably a yeast or a plant, more preferably a yeast, notably a yeast strain of industrial interest, comprising:

introducing into a cell of said organism:

a) a fusion protein comprising a Cas9 domain and a Spo11 domain, or a nucleic acid encoding said fusion protein; and b) one or more guide RNAs, or one or more nucleic acids encoding said guide RNAs, said guide RNAs comprising an RNA structure for binding to the Cas9 domain and a sequence complementary to a targeted chromosomal region; and inducing said cell to enter meiotic prophase I;

obtaining a cell or cells having the desired recombination(s) at the targeted chromosomal region(s); and generating a variant of the organism from said recombinant cell.

In this method, the term "variant" should be understood broadly to refer to an organism having at least one genotypic or phenotypic difference from the parent organisms.

The recombinant cells can be obtained by allowing meiosis to continue until spores are obtained, or, in the case of yeasts, by returning the cells to growth conditions after the induction of double-strand breaks in order to resume a mitotic process.

When the eukaryotic cell is a plant cell, a variant of the plant can be generated by fusion of plant gametes, at least one of the gametes being a recombinant cell by the method according to the invention.

The present invention also concerns a method for identifying or locating the genetic information encoding a characteristic of interest in the genome of a eukaryotic cell, preferably a yeast, comprising:

introducing into the eukaryotic cell:

a) a fusion protein comprising a Cas9 domain and a Spo11 domain, or a nucleic acid encoding said fusion protein; and b) one or more guide RNAs, or one or more nucleic acids encoding said guide RNAs, said guide RNAs comprising an RNA structure for binding to the Cas9 domain and a sequence complementary to a targeted chromosomal region; and inducing said cell to enter meiotic prophase I;

obtaining a cell or cells having the desired recombination(s) at the targeted chromosomal region(s); and analyzing the genotypes and phenotypes of the recombinant cells so as to identify or locate the genetic information encoding the characteristic of interest.

Preferably, the characteristic of interest is a quantitative trait of interest (QTL).

According to another aspect, the present invention relates to a fusion protein comprising a Cas9 domain and a Spo11 domain as described above.

The present invention also concerns a nucleic acid encoding said fusion protein according to the invention.

The nucleic acid according to the invention can be in the form of single-stranded or double-stranded DNA and/or RNA. According to a preferred embodiment, the nucleic acid is an isolated DNA molecule, synthesized by recombinant techniques well-known to a person skilled in the art. The nucleic acid according to the invention can be deduced from the sequence of the fusion protein according to the invention and the use of codons may be appropriate according to the host cell in which the nucleic acid must be transcribed.

The present invention further concerns an expression cassette comprising a nucleic acid according to the invention operably linked to the sequences necessary to its expression. Notably, the nucleic acid can be under the control of a promoter allowing its expression in a host cell. Generally, an expression cassette comprises, or consists of, a promoter for initiating transcription, a nucleic acid according to the invention, and a transcription terminator.

The term "expression cassette" refers to a nucleic acid construction comprising a coding region and a regulatory region, operably linked. The expression "operably linked" indicates that the elements are combined so that the expression of the coding sequence is under the control of the transcriptional promoter. Typically, the promoter sequence is placed upstream of the gene of interest, at a distance therefrom compatible with control of its expression. Spacer sequences may be present, between the regulatory elements and the gene, since they do not prevent the expression. The expression cassette may also comprise at least one activating sequence ("enhancer") operably linked to the promoter.

A wide variety of promoters that can be used for the expression of genes of interest in host cells or organisms are at the disposal of a person skilled in the art. They include constitutive promoters as well as inducible promoters which are activated or suppressed by exogenous physical or chemical stimuli.

Preferably, the nucleic acid according to the invention is placed under the control of a constitutive promoter or a meiosis-specific promoter.

Exemplary meiosis-specific promoters that can be used in the context of the present invention include, but are not limited to, endogenous Spo11 promoters, promoters of the Spo11 partners for forming double-strand breaks, the Rec8 promoter (Murakami & Nicolas, 2009, Mol. Cell. Biol, 29, 3500-16), or the Spo13 promoter (Malkova et al., 1996, Genetics, 143, 741-754).

Other inducible promoters may also be used such as the estradiol promoter (Carlile & Amon, 2008 Cell, 133, 280-91), the methionine promoter (Care et al., 1999, Molecular Microb 34, 792-798), promoters induced by heat-shock, metals, steroids, antibiotics and alcohol.

The constitutive promoters that can be used in the context of the present invention are, by way of nonlimiting examples: the cytomegalovirus (CMV) immediate-early gene promoter, the simian virus (SV40) promoter, the adenovirus major late promoter, the Rous sarcoma virus (RSV) promoter, the mouse mammary tumor virus (MMTV) promoter, the phosphoglycerate kinase (PGK) promoter, the elongation factor ED1-alpha promoter, ubiquitin promoters, actin promoters, tubulin promoters, immunoglobulin promoters, alcohol dehydrogenase 1 (ADH1) promoter, RNA polymerase III-dependent promoters such as the U6, U3, H1, 7SL, pRPR1 ("Ribonuclease P RNA 1"), SNR52 ("small nuclear RNA 52") promoters, or the promoter pZmUbi.

The transcription terminator can be readily selected by a person skilled in the art. Preferably, this terminator is RPR1t, the 3' flanking sequence of the *Saccharomyces cerevisiae* SUP4 gene or the nopaline synthase terminator (tNOS).

The present invention further concerns an expression vector comprising a nucleic acid or an expression cassette according to the invention. This expression vector can be used to transform a host cell and to express the nucleic acid according to the invention in said cell. The vectors can be constructed by conventional molecular biology techniques, well-known to a person skilled in the art.

Advantageously, the expression vector comprises regulatory elements for expressing the nucleic acid according to the invention. These elements may comprise for example transcription promoters, transcription activators, terminator sequences, initiation codons and termination codons. The methods for selecting these elements as a function of the host cell in which the expression is desired are well-known to a person skilled in the art.

In a particular embodiment, the expression vector comprises a nucleic acid encoding the fusion protein according to the invention, placed under the control of a constitutive promoter, preferably the ADH1 promoter (pADH1). It may also comprise a terminator sequence such as the ADH1 terminator (tADH1).

The expression vector may comprise one or more bacterial or eukaryotic origins of replication. The expression vector may in particular include a bacterial origin of replication functional in *E. coli* such as the ColE1 origin of replication. Alternatively, the vector may comprise a eukaryotic origin of replication, preferably functional in *S. cerevisiae.*

The vector may further comprise elements allowing its selection in a bacterial or eukaryotic host cell such as, for example, an antibiotic-resistance gene or a selection gene ensuring the complementation of the respective gene deleted in the host-cell genome. Such elements are well-known to a person skilled in the art and are extensively described in the literature.

In a particular embodiment, the expression vector comprises one or more antibiotic resistance genes, preferably a gene for resistance to ampicillin, kanamycin, hygromycin, geneticin and/or nourseothricin.

The expression vector may also comprise one or more sequences allowing targeted insertion of the vector, the expression cassette or the nucleic acid in the genome of a host cell. Preferably, the insertion is carried out at a gene whose inactivation allows the selection of the host cells having integrated the vector, the cassette or the nucleic acid, such as the TRP1 locus.

The vector may be circular or linear, single or double-stranded. It is advantageously selected from plasmids, phages, phagemids, viruses, cosmids and artificial chromosomes. Preferably, the vector is a plasmid.

The present invention concerns in particular a vector, preferably a plasmid, comprising a bacterial origin of replication, preferably the ColE1 origin, a nucleic acid as defined above under the control of a promoter, preferably a constitutive promoter such as the ADH1 promoter, a terminator, preferably the ADH1 terminator, one or more selection markers, preferably resistance markers such as the gene for resistance to kanamycin or to ampicillin, and one or more sequences allowing targeted insertion of the vector, the expression cassette or the nucleic acid into the host-cell genome, preferably at the TRP1 locus of the genome of a yeast.

In a particular embodiment, the nucleic acid according to the invention carried by the vector encodes a fusion protein comprising one or more tags, preferably comprising a tag consisting of six histidines and/or one or more Flag motifs, preferably three Flag motifs. Preferably the tag or tags are C-terminal.

According to a particular embodiment the expression vector is the plasmid P1 having the nucleotide sequence SEQ ID NO: 1 or the plasmid P2 having the nucleotide sequence SEQ ID NO: 2.

The present invention also concerns the use of a nucleic acid, an expression cassette or an expression vector according to the invention to transform or transfect a cell. The host cell may be transformed/transfected in a transient or stable manner and the nucleic acid, the cassette or the vector may be contained in the cell as an episome or integrated into the host-cell genome.

The present invention concerns a host cell comprising a fusion protein, a nucleic acid, an expression cassette or an expression vector according to the invention.

Preferably, the cell is a eukaryotic cell, in particular a yeast, plant, fungal or animal cell. Particularly preferably, the host cell is a yeast cell. In a particular embodiment, the host cell is nonhuman and/or non-embryonic.

According to a particular embodiment, the eukaryotic cell is a yeast cell, in particular a yeast of industrial interest. Exemplary yeasts of interest include, but are not limited to, yeasts of the genus *Saccharomyces sensu stricto, Schizosaccharomyces, Yarrowia, Hansenula, Kluyveromyces, Pichia* or *Candida*, as well as the hybrids obtained from a strain belonging to one of these genera.

Preferably, the yeast of interest belongs to the genus *Saccharomyces*, preferably a yeast selected from the group consisting of *Saccharomyces cerevisiae, Saccharomyces bayanus, Saccharomyces castelli, Saccharomyces eubayanus, Saccharomyces kluyveri, Saccharomyces kudriavzevii, Saccharomyces mikatae, Saccharomyces uvarum, Saccharomyces paradoxus, Saccharomyces pastorianus* (also called *Saccharomyces carlsbergensis*), and the hybrids obtained from at least one strain belonging to one of these species, more preferably said eukaryotic host cell is *Saccharomyces cerevisiae.*

According to another particular embodiment, the eukaryotic cell is a fungal cell, in particular a fungal cell of industrial interest. Exemplary fungi include, but are not limited to, filamentous fungal cells. Filamentous fungi include fungi belonging to the subdivisions Eumycota and Oomycota. The filamentous fungal cells may be selected from the group consisting of *Trichoderma, Acremonium, Aspergillus, Aureobasidium, Bjerkandera, Ceriporiopsis, Chrysosporium, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium* or *Trametes* cells.

In another preferred embodiment, the cell is a plant cell, preferably a plant cell selected from the group consisting of rice, wheat, soy, maize, tomato, *Arabidopsis thaliana*, barley, rapeseed, cotton, sugarcane and beet, more preferably said eukaryotic host cell is a rice cell.

The present invention also concerns the use of the fusion protein, the nucleic acid, the expression cassette or the expression vector according to the invention to (i) induce targeted meiotic recombinations in a eukaryotic cell, (ii) generate variants of a eukaryotic organism, and/or (iii) identify or locate the genetic information encoding a characteristic of interest in a eukaryotic cell genome.

The present invention further concerns a kit comprising a fusion protein, a nucleic acid, an expression cassette or an expression vector according to the invention, or a host cell transformed or transfected with a nucleic acid, an expression cassette or an expression vector according to the invention. It also concerns the use of said kit to implement a method according to the invention, in particular to (i) induce targeted meiotic recombinations in a eukaryotic cell, (ii) generate variants of a eukaryotic organism, and/or (iii) identify or locate the genetic information encoding a characteristic of interest in a eukaryotic cell genome.

The methods according to the invention may be in vitro, in vivo or ex vivo methods.

The following examples are presented for illustrative and nonlimiting purposes.

EXAMPLES

1. Design, Synthesis and Cloning of a Nucleotide Sequence Encoding the SpCas9 Protein and its Nuclease-Deficient Form SpCas9*

The SpCas9 gene encoding the Cas9 protein comes from the bacterial strain *Streptococcus pyogenes*. The catalytically inactive form of SpCas9 (SpCas9*) is distinguished from that of SpCas9 by two point mutations: the aspartate at position 10 and the histidine at position 840 have both been substituted by alanines ($Asp^{10} \rightarrow Ala^{10}$ and $His^{840} \rightarrow Ala^{840}$).

Because of variations in the frequency of use of genetic codons between *Streptococcus pyogenes* and *Saccharomyces cerevisiae*, the SpCas9 and SpCas9* gene sequences were adapted in order to optimize their expression in yeast (yeast_optim_SpCas9 and yeast_optim_SpCas9*). The amino acid sequences of the two proteins were not modified.

2. Engineering of the Sequences Yeast_Optim_SpCas9 and Yeast_Optim_SpCas9* in Order to Fuse the SpCas9 and SpCas9* Proteins With the Meiotic Transesterase Spo11

Figure 1:
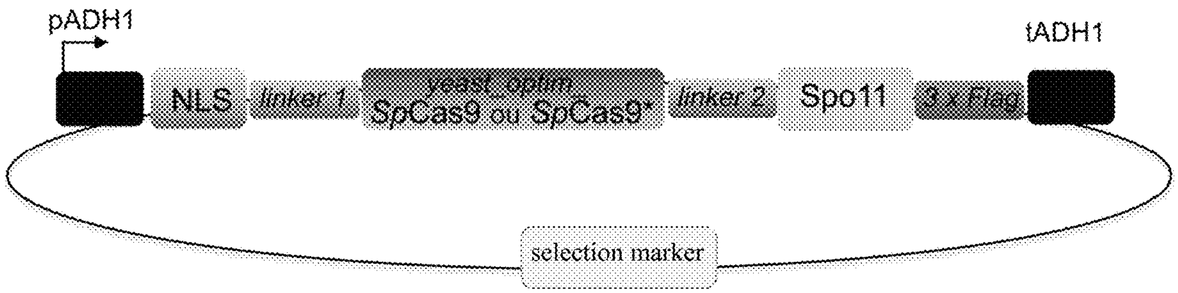
FIG. 1: Diagram representing the plasmids P1 (SEQ ID NO: 1) and P2 (SEQ ID NO: 2) of the SpCas9-Spo11 or SpCas9*-Spo11 fusion. P1 and P2 respectively encode NLS-SpCas9 Spo11 and NLS-SpCas9*-Spo11 expression in yeast. The black blocks represent the constitutive ADH1 promoter (pADH1) and the ADH1 terminator (tADH1). The arrow indicates the direction of transcription under the control of the ADH1 promoter.

Engineering of the yeast_optim_SpCas9 and yeast_optim_SpCas9* sequences made it possible to fuse the SpCas9 and SpCas9* proteins with a nuclear localization signal (NLS) associated with an N-terminal inker (linker 1) and with a second C-terminus linker (linker 2) (which will separate the SpCas9 and SpCas9* proteins from the Spo11 protein in the final construction). The nucleotide sequences thus obtained and encoding the protein sequences NLS-linker1-SpCas9-linker2 and NLS-linker1-SpCas9*-linker2 were then cloned into an integrative plasmid, containing the complete form of the Spo11 protein from *Saccharomyces cerevisiae* tagged with a sequence encoding the C-terminal double 6×His-3×Flag motif and whose expression is controlled by the constitutive promoter pADH1. The resulting plasmid constructions, P1 and P2, thus contained inphase fusion of the N-terminus of NLS-linker1-SpCas9-linker2 and NLS-linker1-SpCas9*-linker2 to the Spo11 protein. Consequently, P1 and P2 respectively allowed the constitutive expression in yeast of the NLS-SpCas9-Spo11-6×His-3×Flag (SEQ ID NO: 6) and NLS-SpCas9*-Spo11-6×His-3×Flag (SEQ ID NO: 7) fusion proteins (FIG. 1).

3. Engineering of Single and Multiple Guide RNA Expression Vectors

Figure 2:
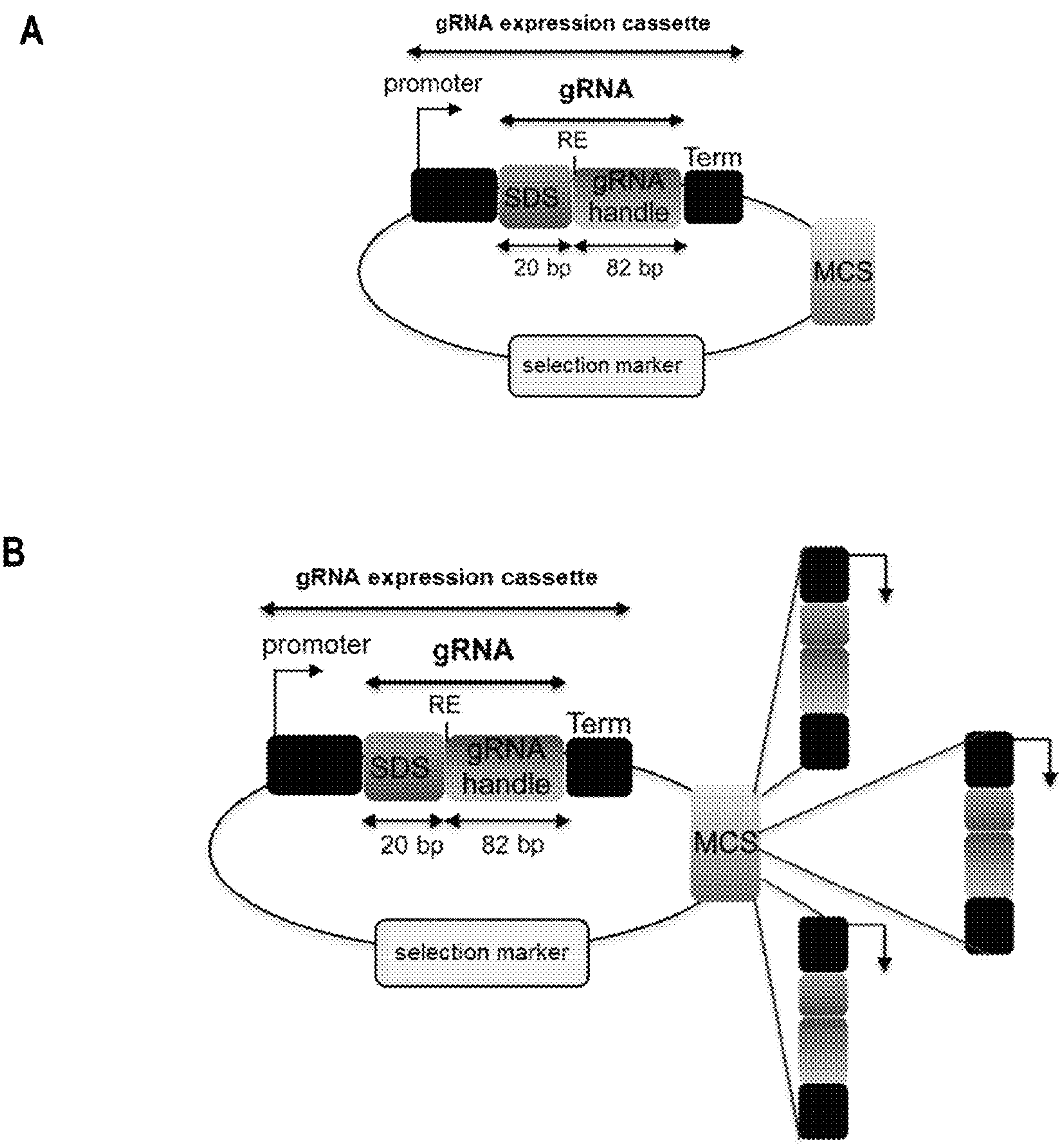
FIG. 2: Diagram representing the gRNA expression plasmids in yeast cells. (A) Diagram of the plasmid containing a single gRNA expression cassette for targeting a single region of the yeast genome. RE indicates the restriction site where the specificity-determining sequence (SDS) of the gRNA is inserted by the Gibson method. The promoter and the terminator (Term) are RNA polymerase III-dependent. The arrow on the promoter indicates the direction of transcription of the sequence. A gRNA expression cassette contains a gRNA flanked by a promoter and a terminator. (B) Diagram of the plasmid containing several gRNA expression cassettes for targeting multiple regions of the yeast genome (multiplexed targeting). The various gRNA cassettes are distinguished by their specificity-determining sequence (SDS). They were introduced successively into the multiple cloning site (MCS) by conventional cloning/ligation techniques.
Figure 3:
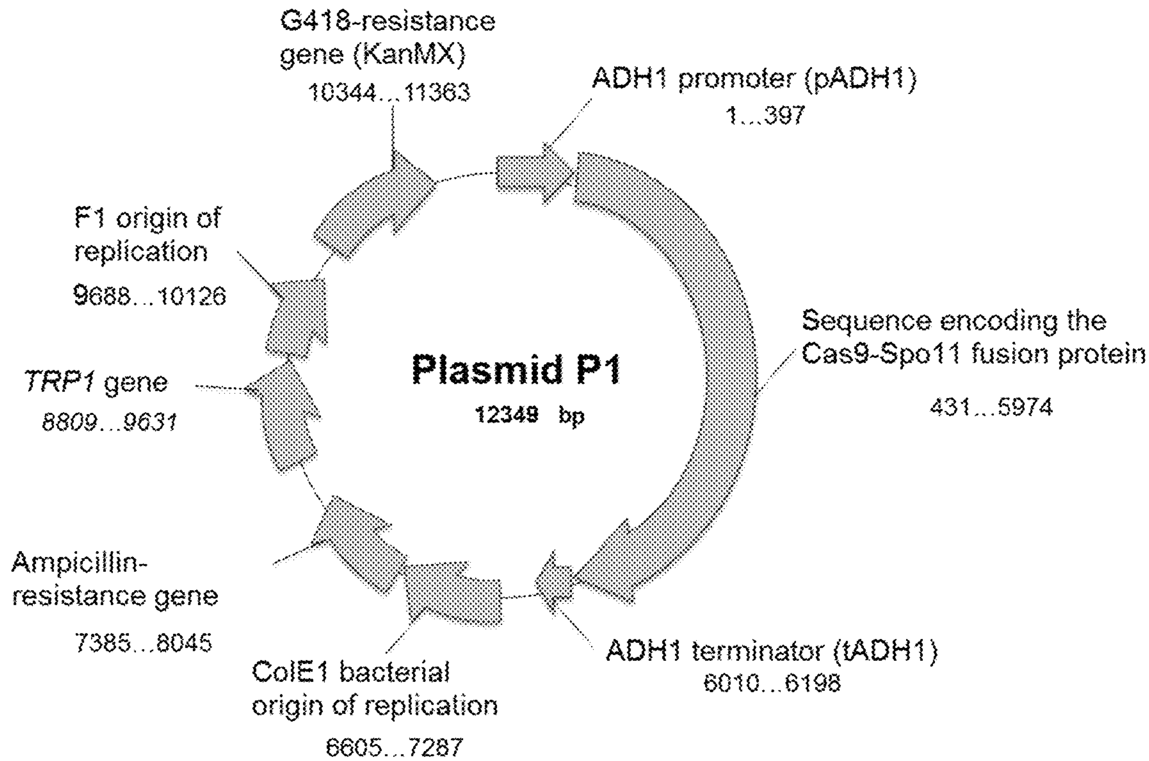
FIG. 3: Diagram representing the plasmid P1 (SEQ ID NO: 1).
Figure 4:
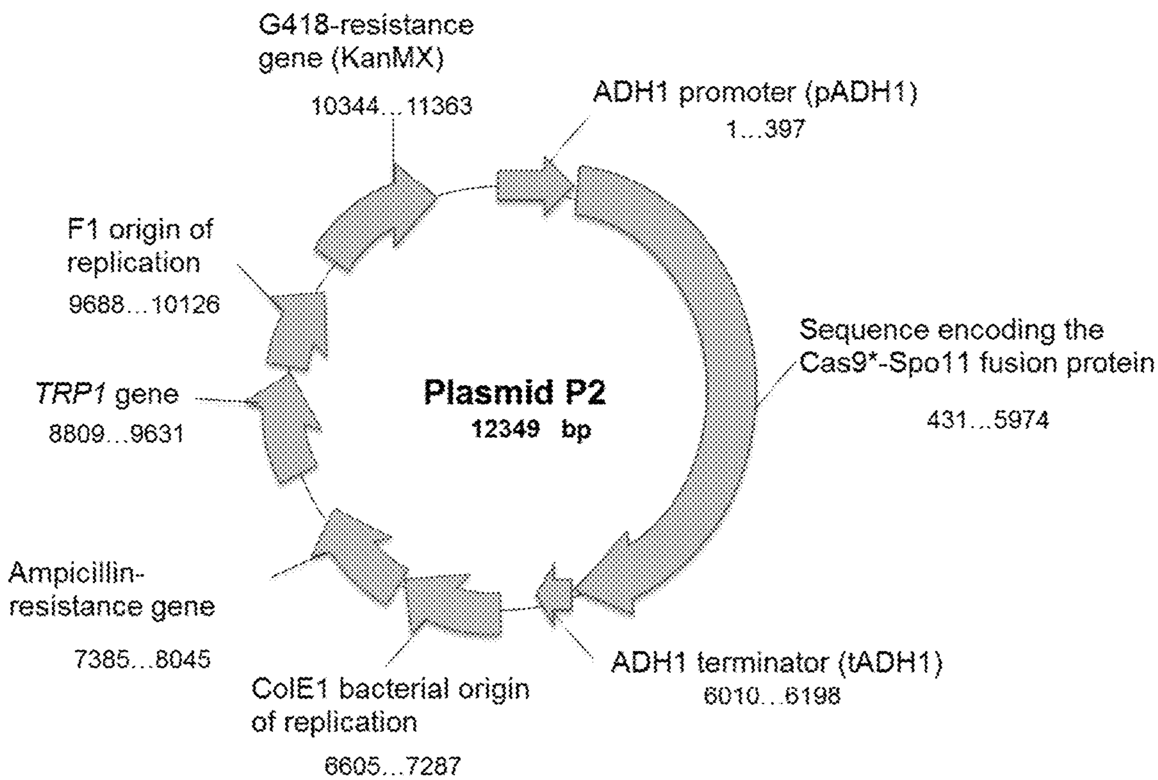
FIG. 4: Diagram representing the plasmid P2 (SEQ ID NO: 2).

Starting with a 2 micron (2 μ)plasmid (Farzadfard F et al., 2013, ACS Synth. Biol., 2, pp. 604-613; DiCarlo J E et al., 2013, Nucleic Acids Res., 41(7), pp. 4336-4343) containing the handle region (82 nucleotides) of a guide RNA (gRNA), placed under the control of a constitutive RNA polymerase III-dependent promoter such as pRPR1 or SNR52, the expression vector for a single 102-nucleotide gRNA was constructed by cloning the 20-nucleotide specificity-determining sequence (SDS region) of the gRNA at a restriction site located immediately 5' of the sequence encoding the handle region of the linearized vector, by the Gibson assembly method (FIG. 2A).

This expression vector contained a sequence comprising numerous unique restriction sites (multiple cloning site (MCS)) downstream of the terminator (RPR1t or 3' flanking sequence of SUP4). Also, in order to obtain a system allowing multiplexed targeting of meiotic recombination sites, several gRNA expression cassettes were inserted into the expression vector at its MCS. The gRNA expression cassettes consist of a constitutive RNA polymerase III-dependent promoter (pRPR1 or SNR52), the specific gRNA and a terminator (RPR1t or the 3' flanking sequence of SUP4). These gRNA expression cassettes were first cloned into unique gRNA expression vectors (see above), then were amplified by PCR before being cloned successively into the multiple cloning site (MCS) of the expression vector for a single gRNA by conventional insertion/ligation techniques (FIG. 2B). This strategy ends up in concatenating several gRNA cassettes into a single expression vector.

4. Co-expression of SpCas9-Spo11 and SpCas9*-Spo11 Fusion Proteins with gRNAs in Yeast In order to introduce the NLS-SpCas9-Spo11 or NLS-SpCas9*-Spo11 fusions into the chromosomal TRP1 locus, strains of the yeast *Saccharomyces cerevisiae* were transformed by heat shock with the linearized vectors P1 or P2. These fusion proteins, carrying the C-terminal 3×Flag tag, were placed under the control of the constitutive ADH1 promoter. After transformation, the cells were plated on Petri dishes containing selective medium (adapted to the selection markers carried by the plasmids P1 and P2) in order to select the transformants having integrated the fusion into their genome.

The expression vector for the gRNA(s) was then introduced into diploid yeast strains expressing the NLS-SpCas9-Spo11 or NLS-SpCas9*-Spo11 fusion proteins by heat-shock transformation. The cells were then plated on medium selective for the selection markers for the gRNA expression plasmids. The gRNA expression plasmids comprised a 2 micron (4) origin of replication which enabled them to be maintained with a high copy number in each yeast cell (50-100 copies/cell).

The formation of meiotic double-strand breaks generated in a single or multiplexed manner by the SpCas9-Spo11 or SpCas9*-Spo11 fusion proteins at the genomic sites targeted by single or multiple gRNAs is then detected by Southern Blot analysis of genomic DNA extracted from diploid cells grown in sporulation medium.

5. Complementation of Spores Derived From Sporulation of SPO11 Gene-Inactivated Strains by the Expression of the SpCas9*-Spo11 Fusion Protein The inventors analyzed the viability of spores derived from meiosis of the following diploid strains of *Saccharomyces cerevisiae:*

- a SPO11/SPO11 strain (ORD7339) comprising two copies of the wildtype allele of the SPO11 gene,
- a spo11/spo11 strain (AND2822) comprising two copies of the mutated allele of the SPO11 gene. This mutated allele corresponds to the wildtype allele in which a genetic marker totally inactivating the gene was inserted,
- a spo11/spo11 dCAS9-SPO11/0 strain (AND2820) comprising two copies of the mutated allele of the SPO11 gene and one copy of the gene encoding the SpCas9*-Spo11 fusion protein integrated into one of the two copies of chromosome IV into the TRP1 locus, and
- a spo11/spo11 dCAS9-SPO11/dCAS9-SPO11 strain (AND2823) comprising two copies of the mutated allele of the SPO11 gene and two copies of the gene encoding the SpCas9*-Spo11 fusion protein integrated into both copies of chromosome IV into the TRP1 locus.

Figure 5:
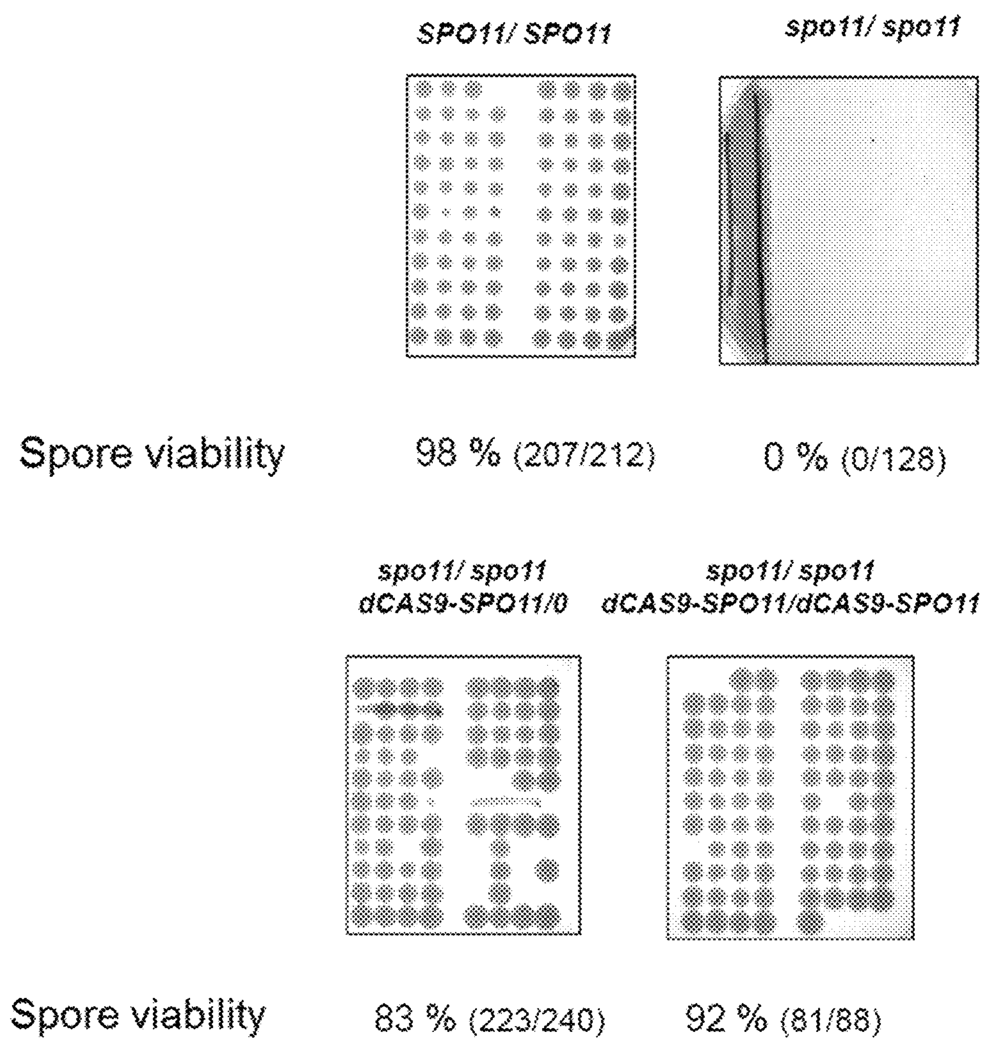
FIG. 5: Viability of spores derived from sporulation of strains expressing or not expressing the SpCas9*-Spo11 fusion protein. Growth of spores derived from meiosis of the diploid strains SPO11/SPO11 (ORD7339), spo11/spo11

The results presented in FIG. 5 show that the expression of the SpCas9*-Spo11 fusion protein complements the inviability of spores derived from sporulation of SPO11 gene inactivated strains.

6. Targeting of Meiotic Double-Strand Breaks by the SpCas9*-Spo11 Fusion Protein and a Guide RNA Specific for the YCR048W Region The SpCas9*-Spo11 expression cassette (dCAS9-SPO11) was integrated into the chromosomal TRP1 locus (chromosome IV). The UAS1-YCR048W guide RNA (sgRNA) (SEQ ID NO: 10) was expressed by the multicopy replicative (non-integrative) plasmid as described in FIG. 2A. The fusion gene carrying the dCAS9-SPO11 construction was expressed under the control of the constitutive ADH1 promoter. The guide RNA was expressed under the control of the constitutive RPR1 promoter. The yeast cells were transformed by the conventional electroporation method. The integration of the cassette carrying the dCAS9-SPO11 construction was confirmed by Southern blot.

The following strains were used:

SPO11/SPO11 (ORD7304),

SPO11/SPO11 expressing the UAS1-YCR48W guide RNA (sgRNA) (ANT2524), spo11/spo11 dCAS9-SPO11/0 expressing the guide RNA handle, i.e., a guide RNA without the SDS region which is specific for the chromosomal target (ANT2527), spo11/spo11 dCAS9-SPO11/0 expressing the UAS1-YCR48W guide RNA (sgRNA) (ANT2528), and spo11/spo11 dCAS9-SPO11/dCAS9-SPO11 expressing the UAS1-YCR48W guide RNA (sgRNA) (ANT2529).

The cells were collected after transfer to sporulation medium (1% KAc) and were taken at the indicated times (hours). The strains are homozygous for deletion of the SAE2 gene which inhibits repair of DNA double-strand breaks (DSBs). The accumulation of DSBs was detected by Southern blot after genomic DNA digestion by the restriction enzyme AseI. The DNA was probed with a fragment internal to the YCR048W locus. The bands were quantified using the ImageJ software.

The results presented in FIG. 6 show that the expression of the SpCas9*-Spo11 construction (dCAS9-SPO11) induces meiotic DNA double-strand breaks (DSBs) at the natural cleavage sites of the Spo11 protein (YCR043C-YCR048W region of chromosome III (DSBs I to VI symbolized by black squares in FIG. 6) and at the UAS1 site (DSB VII, black triangle) targeted by the UAS1-YCR048W guide RNA and located in the coding region of the YCR048W gene.

7. Targeting of Meiotic Double-Strand Breaks by the SpCas9*-Spo11 Fusion Protein and a Guide RNA Specific for the YCR048W Region The SpCas9*-Spo11 expression cassette (dCAS9-SPO11) was integrated into the chromosomal TRP1 locus (chromosome IV). The UAS1-YCR048W or UAS2-YCR048W (SEQ ID NO: 11) guide RNA (sgRNA) was expressed by the multicopy replicative (non integrative) plasmid as described in FIG. 2A. The fusion gene carrying the dCAS9-SPO11 construction was expressed under the control of the constitutive ADH1 promoter. The guide RNA was expressed under the control of the constitutive RPR1 promoter. The yeast cells were transformed by the conventional electroporation method. The integration of the cassette carrying the dCAS9-SPO11 construction was confirmed by Southern blot.

The following strains were used:

SPO11/SPO11 (ORD7304),

SPO11/SPO11 expressing the UAS1-YCR048W guide RNA (sgRNA) (ANT2524),

SPO11/SPO11 dCAS9-SPO11/0 expressing the guide RNA handle, i.e., a guide RNA without the SDS region which is specific for the chromosomal target (ANT2518), SPO11/SPO11 dCAS9-SPO11/0 expressing the UAS1-YCR048W guide RNA (sgRNA) (ANT2519), SPO11/SPO11 dCAS9-SPO11/dCAS9-SPO11 expressing the UAS1-YCR48W guide RNA (sgRNA) (ANT2522), SPO11/SPO11 dCAS9-SPO11/0 expressing the UAS2-YCR048W guide RNA (sgRNA) (ANT2520), SPO11/SPO11 dCAS9-SPO11/dCAS9-SPO11 expressing the UAS2-YCR048W guide RNA (sgRNA) (ANT2523), and spo11/spo11 dCAS9-SPO11/0 expressing the UAS1-YCR048W guide RNA (sgRNA) (ANT2528).

The cells were collected after transfer to sporulation medium (1% KAc) and were taken at the indicated times (hours). The strains are homozygous for deletion of the SAE2 gene which inhibits repair of DNA double-strand breaks (DSBs). The accumulation of DSBs was detected by Southern blot after digestion of genomic DNA by the restriction enzymes AseI and SacI. The DNA was probed with a fragment internal to the YCR048W locus. The bands were quantified using the ImageJ software.

The results presented in FIG. 7 indicate that the expression of the dCAS9-SPO11 construction induces meiotic DNA double-strand breaks (DSBs) at the natural cleavage sites of the Spo11 protein (YCR047C-YCR048W region of chromosome III (DSBs V and VI symbolized by squares) and at the UAS1-YCR048W site (DSB VII symbolized by a triangle) targeted by the UAS1-YCR048W guide RNA in the 5' coding region of the YCR048W gene and at the UAS2 YCR048W site (DSB VIII symbolized by a circle) targeted by the UAS2-YCR048W guide RNA in the 3' coding region of the YCR048W gene. These results show that the targeting is effective in the strains carrying the wildtype SPO11 gene or the mutated spo11 gene.

8. Targeting of Meiotic Double-Strand Breaks by the SpCas9*-Spo11 Fusion Protein and a Guide RNA Specific for the GAL2 Region The SpCas9*-Spo11 expression cassette (dCAS9-SPO11) was integrated into the chromosomal TRP1 locus (chromosome IV). The UAS D/E-GAL2 guide RNA (sgRNA) (SEQ ID NO: 12) was expressed by the multicopy replicative (non-integrative) plasmid as described in FIG. 2A. The fusion gene carrying the dCAS9-SPO11 construction was expressed under the control of the constitutive ADH1 promoter. The guide RNA was expressed under the control of the constitutive RPR1 promoter. The yeast cells were transformed by the conventional electroporation method. The integration of the cassette carrying the dCAS9-SPO11 construction was confirmed by Southern blot.

The following strains were used:

SPO11/SPO11 (ORD7304), spo11/spo11 GAL4/GAL4 dCAS9-SPO11/0 expressing the guide RNA handle, i.e., a guide RNA without the SDS region which is specific for the chromosomal target (ANT2527), spo11/spo11 gal4/gal4 dCAS9-SPO11/0 expressing the guide RNA handle (ANT2536) (both alleles of the GAL4 gene are mutated and thus inactive), spo11/spo11 GAL4/GAL4 dCAS9-SPO11/0 expressing the UAS D/E-GAL2 guide RNA (ANT2530), and spo11/spo11 gal4/gal4 dCAS9-SPO11/0 expressing the UAS D/E-GAL2 guide RNA (ANT2533).

The cells were collected after transfer to sporulation medium (1% KAc) and were taken at the indicated times (hours). The strains are homozygous for deletion of the SAE2 gene which inhibits repair of DNA double-strand breaks (DSBs). The accumulation of DSBs was detected by Southern blot after digestion of genomic DNA by the restriction enzyme XbaI. The DNA was probed with the terminal portion of the GAL2 gene. The bands were quantified using the ImageJ software.

The results presented in FIG. 8 show that the expression of the dCAS9-SPO11 construction induces meiotic DNA double-strand breaks (DSBs) at the UAS D/E site of the GAL2 gene promoter targeted by the UAS D/E-GAL2 guide RNA.

9. Targeting of Meiotic Double-Strand Breaks by the SpCas9*-Spo11 Fusion Protein and a Guide RNA Specific for the SWC3 Region The SpCAS9*-SPO11 expression cassette (dCas9-SPO11) was integrated into the chromosomal TRP1 locus (chromosome IV). The SWC3 guide RNA ($sgRNA_{SWC3}$) (SEQ ID NO: 13) was expressed by the multicopy replicative (non-integrative) plasmid as described above (FIG. 2A). The fusion gene carrying the SpCAS9*-SPO11 construction was expressed under the control of the constitutive ADH1 promoter. The guide RNA was expressed under the control of the constitutive RPR1 promoter. The yeast cells were transformed by the conventional electroporation method. The integration of the cassette carrying the SpCAS9* SPO11 construction was confirmed by Southern blot.

The following strains were used:

SPO11/SPO11 (ORD7304), spo11/spo11 SpCAS9*-SPO11/0 expressing the guide RNA handle, i.e., a guide RNA without the SDS region which is specific for the chromosomal target (ANT2527), spo11/spo11 SpCAS9*-SPO11/0 expressing the SWC3 guide RNA ($sgRNA_{SWC3}$) (ANT2564).

The cells were collected after transfer to sporulation medium (1% KAc) and were taken at the indicated times (hours). The strains are homozygous for deletion of the SAE2 gene which inhibits repair of DNA double-strand breaks (DSBs). The accumulation of DSBs was detected by Southern blot after digestion of genomic DNA by the restriction enzymes PacI and AvrII. The DNA was probed with a fragment internal to the SPOT locus. The bands were quantified using the ImageJ software.

The results presented in FIG. 9 show that the expression of the SpCAS9*-Spo11 construction induces meiotic DNA double-strand breaks (DSBs) at the natural cleavage sites of the Spo11 protein (SIN8-SWC3 region) of chromosome I (DSBs I, II and III symbolized by black squares in FIG. 9) and at the target site (DSBs IV symbolized by a circle) by the SWC3 guide RNA ($sgRNA_{SWC3}$) and located in the coding region of the SWC3 gene.

10. Targeting of Meiotic DNA Double-Strand Breaks by the SpCas9*-Spo11 Protein and Several Multiplexed RNA Guides Specific for the GAL2 Region The SpCAS9*-Spo11 expression cassette (dCas9-SPO11) was integrated into the chromosomal TRP1 locus (chromosome IV). The UAS-A guide RNA ($sgRNA_{UAS\text{-}A}$) (SEQ ID NO: 14), UAS-B guide RNA ($sgRNA_{UAS\text{-}B}$) (SEQ ID NO: 15) and UASD/E guide RNA ($sgRNA_{UAS\text{-}D/E}$) (SEQ ID NO: 12) were expressed individually and in multiplex (Multi gRNAs) by the multicopy replicative (non-integrative) plasmid as described above (FIG. 2A).

The fusion gene carrying the SpCAS9*-SPO11 construction was expressed under the control of the constitutive ADH1 promoter. The guide RNAs were expressed under the control of the constitutive RPR1 promoter. The yeast cells were transformed by the conventional electroporation method. The integration of the cassette carrying the SpCAS9*-SPO11 construction was confirmed by Southern blot.

The following strains were used:

spo11/spo11 GAL4/GAL4 SpCAS9*-SPO11/0 expressing the guide RNA handle, i.e., a guide RNA without the SDS region which is specific for the chromosomal target (ANT2527), spo11/spo11 GAL4/GAL4 SpCAS9*-SPO11/0 expressing the UAS-A guide RNA ($sgRNA_{UAS\text{-}A}$) (ANT2532), spo11/spo11 gal4/gal4 SpCAS9*-SPO11/0 expressing the UAS-A guide RNA ($sgRNA_{UAS\text{-}A}$) (ANT2534), spo11/spo11 GAL4/GAL4 SpCAS9*-SPO11/0 expressing the UASD/E guide RNA ($sgRNA_{UAS\text{-}D/E}$) (ANT2530), spo11/spo11 gal4/gal4 SpCAS9*-SPO11/0 expressing the UASD/E guide RNA ($sgRNA_{UAS\text{-}D/E}$) (ANT2533), spo11/spo11 GAL4/GAL4 SpCAS9*-SPO11/0 expressing in multiplex the UAS-A guide RNA ($sgRNA_{UAS\text{-}A}$), the UAS-B guide RNA ($sgRNA_{UAS\text{-}B}$) and the UASD/E guide RNA ($sgRNA_{UAS\text{-}D/E}$) (MultigRNAs) (ANT2551), spo11/spo11 gal4/gal4 SpCAS9*-SPO11/0 expressing in multiplex the UAS-A guide RNA ($sgRNA_{UAS\text{-}A}$), the UAS-B guide RNA ($sgRNA_{UAS\text{-}B}$) and the UASD/E guide RNA ($sgRNA_{UAS\text{-}D/E}$) (MultigRNAs) (ANT2552).

The cells were collected after transfer to sporulation medium (1% KAc) and were taken at the indicated times (hours). The strains are homozygous for deletion of the SAE2 gene which inhibits repair of DNA double-strand breaks (DSBs). The accumulation of DSBs was detected by Southern blot after digestion of genomic DNA by the restriction enzyme XbaI. The DNA was probed with the terminal portion of the GAL2 gene. The bands were quantified using the ImageJ software.

The results presented in FIG. 10 indicate that the expression of the SpCAS9*-Spo11 construction (dCas9-SPO11) induces meiotic DNA double-strand breaks (DSBs) at the target sites in the GAL2 gene promoter on chromosome XII by the guide RNA(s). In particular, the co expression of SpCas9*-Spo11 with the individual sgRNAs $sgRNA_{UAS\text{-}A}$ and $sgRNA_{UAS\text{-}D/E}$ leads to the generation of DSBs, respectively, at the UAS-A and UASD/E sites. Interestingly, the targeting of SpCas9*-Spo11 by the coexpression of $sgRNA_{UAS\text{-}A}$, $sgRNA_{UAS\text{-}B}$ and $sgRNA_{UAS\text{-}D/E}$ leads to the formation of multiplex DSBs at the various target sites.

11. Stimulation of Meiotic Recombination by the SpCas9*-SPO11 Protein and Several Multiplexed Guide RNAs in the GAL2 Target Region In order to detect the crossovers induced by the expression of CRISPR/SpCas9*-Spo11, the NatMX and HphMX cassettes (which respectively confer resistance to nourseothricin and to hygromycin) were trans inserted upstream and downstream of the GAL2 gene in diploid cells (see FIG. 11A).

The SpCAS9*-Spo11 expression cassette (dCAS9-SPO11) was integrated into the chromosomal TRP1 locus (chromosome IV). The UASD/E guide RNA ($sgRNA_{UAS\text{-}D/E}$) (SEQ ID NO: 12) was expressed by the multicopy replicative (non-integrative) plasmid as described above (FIG. 2A). The multiplex expression of the UAS-A guide RNA ($sgRNA_{UAS\text{-}A}$) (SEQ ID NO: 14), the UAS-B guide RNA ($sgRNA_{UAS\text{-}B}$) (SEQ ID NO: 15) and the UASD/E guide RNA ($sgRNA_{UAS\text{-}D/E}$) (SEQ ID NO: 12) was carried out from the same guide RNA expression plasmid described above (Multi gRNAs). The fusion gene carrying the SpCAS9*-SPO11 construction was expressed under the control of the constitutive ADH1 promoter. The guide RNA was expressed under the control of the constitutive RPR1 promoter. The yeast cells were transformed by the conventional electroporation method. The integration of the cassette carrying the SpCAS9*-SPO11 construction was confirmed by Southern blot.

The following strains were used:

SPO11/SPO11 pEMP46::NatMX/0 tGAL2::KanMX/0 (ANT2527), spo11/spo11 pEMP46::NatMX/0 tGAL2::KanMX/0 SpCAS9*-SPO11/0 expressing the guide RNA handle, i.e., a guide RNA without the SDS region which is specific for the chromosomal target (ANT2539), spo11/spo11 pEMP46::NatMX/0 tGAL2::KanMX/0 SpCAS9*-SPO11/0 expressing the UASD/E guide RNA ($sgRNA_{UAS-D/E}$) (ANT2540), spo11/spo11 pEMP46::NatMX/0 tGAL2::KanMX/0 SpCAS9*-SPO11/0 expressing in multiplex the UAS-A guide RNA ($sgRNA_{UAS-A}$), the UAS-B guide RNA ($sgRNA_{UAS-B}$) and the UASD/E guide RNA ($sgRNA_{UAS-D/E}$) (MultigRNAs) (ANT2557).

After sporulation, the tetrads composed of 4 spores were dissected and the spores genotyped after germination for nourseothricin and hygromycin segregation. The number of tetrads showing a parental ditype (PD) was compared with those showing a tetratype (T) and a non parental ditype (NPD). The genetic distance in centimorgans was determined according to the formula cM=100(T+6NPD)/2(PD+T+NPD). The increase in the number of tetratypes in the cells expressing SpCAS9*-SPO11 (strains ANT2540 and ANT2557) was tested statistically with Fisher's test by calculating the p-value with respect to the cells co-expressing SpCAS9*-SPO11 and the guide RNA handle (strain ANT2539).

The results presented in FIG. 11B show that the expression of the SpCas9*-SPO11 construction (dCAS9-SPO11) stimulates meiotic recombination in the GAL2 target region.

12. Targeting of Meiotic DNA Double-Strand Breaks by the SpCas9*-Spo11 Fusion Protein and a Guide RNA Specific for the Sequence Encoding the PUT4 Gene The SpCAS9*-Spo11 expression cassette (dCAS9-SPO11) was integrated into the chromosomal TRP1 locus (chromosome IV). The PUT4 guide RNA ($sgRNA_{PUT4}$) (SEQ ID NO: 16) was expressed by the multicopy replicative (non-integrative) plasmid as described above (FIG. 2A). The fusion gene carrying the SpCAS9*-SPO11 construction was expressed under the control of the constitutive ADH1 promoter. The guide RNA was expressed under the control of the constitutive RPR1 promoter. The yeast cells were transformed by the conventional electroporation method. The integration of the cassette carrying the SpCAS9* SPO11 construction was confirmed by Southern blot.

The following strains were used:

SPO11/SPO11 (ORD7304), spo11/spo11 SpCAS9*-SPO11/0 expressing the guide RNA handle, i.e., a guide RNA without the SDS region which is specific for the chromosomal target (ANT2527), spo11/spo11 SpCAS9*-SPO11/0 expressing the PUT4 guide RNA ($sgRNA_{PUT4}$) (ANT2547).

The cells were collected after transfer to sporulation medium (1% KAc) and were taken at the indicated times (hours). The strains are homozygous for deletion of the SAE2 gene which inhibits repair of DNA double-strand breaks (DSBs). The accumulation of DSBs was detected by Southern blot after digestion of genomic DNA by the restriction enzymes BamHI and XhoI. The DNA was probed with a fragment internal to the CIN1 locus. The bands were quantified using the ImageJ software.

The results presented in FIG. 12 show that the expression of the SpCAS9*-SPO11 construction (dCas9-SPO11) induces meiotic DNA double-strand breaks (DSBs) at the natural cleavage sites of the Spo11 protein (PYK2-PUT4 region) of chromosome XV (DSBs I, II, III and V symbolized by black squares in FIG. 11) and at the target site (DSBs IV symbolized by a black triangle) by the PUT4 guide RNA ($sgRNA_{PUT4}$) and located in the coding region of the PUT4 gene.

13. Conclusion

The results presented in FIGS. 5 to 12 show that:

the expression of the SpCas9*-Spo11 fusion protein (dCAS9-SPO11) complements the inviability of spores derived from sporulation of SPO11 gene-inactivated strains, the expression of the SpCas9*-Spo11 fusion protein (dCAS9-SPO11) induces the formation of meiotic double-strand breaks at natural DSB sites, the coexpression of the SpCas9*-Spo11 fusion protein (dCAS9-SPO11) and a gRNA induces the formation of meiotic double-strand breaks at natural DSB sites and at the target site, the coexpression of the SpCas9*-Spo11 fusion protein (dCAS9-SPO11) and multiplexed gRNA induces the formation of meiotic double-strand breaks (DSBs) at the various target sites, and the targeting is effective in the strains having the wildtype SPO11 and the mutated spo11 genetic background.

14. Induction of Meiotic Double-Strand Breaks by the SpCas9*-Spo11 Fusion Protein in Rice a) Preparation of the dCas9-SPO11 Transformation Vector (See FIG. 14)

Cas9 being a protein of prokaryotic origin, the codons used are optimized for the plant species in which the protein is to be expressed. The codons of the Cas9 protein from *Streptococcus pyogenes* are thus optimized for its expression in rice (see Miao et al., Cell Research, 2013, pp. 1-4). Furthermore, the Cas9 protein is inactivated by mutation of two catalytic sites, RuvC and HNH ($Asp^{10}\rightarrow Ala^{10}$ and $His^{840}\rightarrow Ala^{840}$). The catalytically inactive form of SpCas9 is called SpCas9* or dCas9.

First, the dCas9 stop codon is removed and a linker is added in phase at the C-terminal end of dCas9. The linker may be a sequence already known in the literature for use in the plant species concerned or an optimized sequence. The linker CCGGAATTTATGGCCATGGAGGCCCCGGGGATCCGT (SEQ ID NO: 17) used in yeast is also compatible with use in rice.

A nuclear localization signal (NLS) is also added at the N-terminal end of dCas9. Optionally, a linker may be added between the NLS and dCas9, such as for example the sequence GGTATTCATGGAGTTCCTGCTGCG (SEQ ID NO: 18).

The SPO11 sequence is then added in phase at the C-terminal end of the NLS-dCas9-Linker construction. It is possible to use a sequence of complementary DNA (cDNA), of genomic DNA (gDNA) or a complementary DNA sequence with addition of several introns. It is possible to use rice SPO11-1 and/or SPO11-2.

The nopaline synthase terminator (tNOS), adapted to rice, is added in phase to the NLS dCas9-Linker-SPO11 construction.

The maize ubiquitin promoter pZmUbi1 (Christensen A H et al., 1992, Plant Mol Biol, 18(4), pp. 675-689 or Christensen A H and Quail P H, 1995, Transgenic Res, 5(3), pp. 213-218), is a promoter allowing ubiquitous and strong expression in rice.

For stable transformation of rice cells, the transfection is carried out with a binary vector, for example the binary vector pCAMBIA5300 carrying a hygromycin-resistance gene interrupted by an intron of the catalase gene. This resistance gene makes it possible to effectively select, on a selective medium, the individuals having integrated dCas9-SPO11 into their genome. This vector also contains a kanamycin-resistance gene, which facilitates cloning and engineering in bacterial hosts.

b) Preparation of the Construct Carrying the Guide RNA

With regard to the "handle" region of the guide RNA (gRNA), the "native" sequence of the bacterium *S. pyogenes* is used. The SDS region determining the specificity of the gRNA is selected as a function of the zone of interest to be targeted using software freely available on the Internet (for example CRISPR PLANT).

The guide RNA is placed under the control of the rice polymerase III U3 promoter (see Miao et al. Cell Research, 2013, pp. 1-4). Alternatively, it is placed under the control of the U6 promoter.

Single Binary Vector

The construction comprising the guide RNA placed under the control of the U3 promoter is integrated into the vector comprising dCAS9-SPO11.

Separate Binary Vectors

In order to target several regions, the guide RNAs are carried by a separate vector, a binary vector carrying a resistance to geneticin (pCAMBIA2300), which makes it possible to apply a dual selection for the presence of the dCas9-SPO11 T-DNA and the gRNA T-DNA.

Several transformation strategies are possible:

- Co-transformation: Starting with two binary vectors, one carrying dCas9-SPO11 and the other the gRNA(s). They are introduced into the same bacterial strain or two different bacterial strains which are then mixed before co-culture with the plant cells.
- Sequential transformations: Stable transformants carrying the dCas9-SPO11 construct are produced and their seeds used to produce calli which are then used for transformation with the gRNA construct by *Agrobacterium* or by bombardment.
- Independent transformations: Plants carrying dCAS9-SPO11 without a guide and plants carrying gRNAs alone are generated. The stable transformants are then crossed so as produce multiple combinations.

c. Transformation of Rice

The transformation of rice is carried out from calli of mature seed embryos according to the protocol detailed in Sallaud C et al., 2003, Theor Appl Genet, 106(8), pp. 1396-1408.

Use of the dCas9-SPO11 Technology to Induce a Targeted Recombination in Wildtype SPO11

The dCas9-SPO11 fusion protein is produced with the native SPO11 protein (SPO11-1 or SPO11-2), as gDNA or cDNA.

- by direct transformation of calli derived from F1 seeds: calli are induced from mature F1 seed embryos obtained by castration and manual fertilization between two parental lines of agronomic interest. The calli are transformed simultaneously with the T-DNA or T-DNAs carrying dCas9-SPO11 and the gRNA(s) (co-transformation). Transformants without gRNA or with a gRNA targeting another region are used as controls to test the efficacy of the system. The recombination analysis is carried out on the F2 plants.
- by separate transformation of calli of each parent: a line is transformed stably and homozygously with the dCas9-SPO11 construct and crossed with the other line carrying the gRNA(s) with heterozygous insertion. The F1 plants carrying both constructs or only the dCas9 SPO11 construct are selected. The recombinations at the target locus (loci) are quantified in the F2 populations derived from the two types of plants.

Use of the dCAS9-SPO11 Technology to Induce a Targeted Recombination in Mutant Spo11

One of the parental lines (seeds carried by a SPO11/spo11 heterozygote) is transformed with the dCas9-SPO11 construct and plants homozygous for the transgene and the spo11 mutation are obtained in T1 generation. The second parental line (seeds carried by a SPO11/spo11 heterozygote) is transformed with the construct carrying the gRNA(s). Plants heterozygous for the gRNA construct and the spo11 mutation are obtained in T1 generation. The two types of plants are crossed: 4 genotypes of F1 seeds are obtained, all carrying the dCas9-SPO11 construct but carrying or not carrying the gRNA and producing or not producing endogenous SPO11. The recombination analysis is carried out on the F2 populations.

We claim:

1. A method for inducing targeted meiotic recombination in a plant cell comprising:

expressing in the plant cell:

a) a fusion protein comprising a bacterial Cas9 protein lacking nuclease activity and a Spo11 protein; and b) one or more guide RNAs, the guide RNAs comprising an RNA structure for binding to the Cas9 protein of the fusion protein and a sequence complementary to a targeted chromosomal region;

thereby inducing meiotic recombination at the targeted chromosomal region, wherein the meiotic recombination at the targeted chromosomal region is increased as compared to the meiotic recombination at the targeted chromosomal region in a control plant cell lacking the fusion protein or the one or more guide RNAs.

2. The method of claim 1, wherein the fusion protein further comprises a nuclear localization signal sequence.

3. The method of claim 1, further comprising expressing one or more additional guide RNAs targeting one or more other chromosomal regions, or nucleic acids encoding the one or more additional guide RNAs.

4. The method of claim 1, further comprising inducing the plant cell to enter meiotic prophase I.

5. The method of claim 1, further comprising regenerating a plant from the plant cell.

6. The method of claim 1, wherein the plant cell is a monocot.

7. The method of claim 1, wherein the plant cell is a dicot.

8. The method of claim 1, wherein the plant cell is selected from the group consisting of rice, wheat, soy, maize, tomato, *Arabidopsis thaliana*, barley, rapeseed, cotton, sugarcane and beet.

9. The method of claim 8, wherein the plant cell is a rice cell.

10. The method of claim 8, wherein the plant cell is a tomato cell.

11. The method of claim 8, wherein the plant cell is a maize cell.

12. The method of claim 1, wherein the Spo11 protein is from rice, wheat, soy, maize, tomato, *Arabidopsis thaliana*, barley, rapeseed, cotton, sugarcane or beet.

13. The method of claim 1, wherein the Spo11 protein is Spo11-1 or Spo11-2.

14. The method of claim 1, wherein the Cas9 protein is from *Streptococcus pyogenes*.

15. The method of claim 1, wherein the fusion protein comprises a linker between the Cas9 protein and the Spo11 protein.

16. The method of claim 15, wherein the fusion protein comprises from N-terminal end to C-terminal end the Cas9 protein, a first linker, and the Spo11 protein.

17. The method of claim 16, wherein the fusion protein comprises from the N-terminal end to the C-terminal end a nuclear localization signal, a second linker, the Cas9 protein, the first linker, and the Spo11 protein.

18. The method of claim 1, wherein the targeted chromosomal region is a region with a reduced recombination frequency relative to an average recombination frequency in the plant cell.

19. The method of claim 1, wherein the targeted chromosomal region is proximal to a centromeric region in a chromosome of the plant cell.

20. The method of claim 1, wherein the plant cell is a meiotic cell.

21. The method of claim 20, wherein the expression in the meiotic plant cell comprises:

transforming a somatic plant cell or a meiotic plant cell with nucleic acid encoding the fusion protein and the one or more guide RNAs.

22. The method of claim 21, wherein the nucleic acid encoding the fusion protein and the nucleic acid encoding the one or more guide RNAs are each located on a single vector.

23. The method of claim 21, wherein the nucleic acid encoding the fusion protein and the nucleic acid encoding the one or more guide RNA are each located on different vectors.

24. The method of claim 21, wherein the nucleic acid encoding the fusion protein and the nucleic acid encoding the one or more guide RNAs are each located on a T-DNA vector.

25. The method of claim 24, wherein the T-DNA vector is transformed into the plant cell by *Agrobacterium* or by bombardment.

26. The method of claim 21, wherein the nucleic acid encoding the fusion protein is operably linked to a constitutive, inducible or meiosis-specific promoter.

27. The method of claim 26, wherein the constitutive, inducible or meiosis-specific promoter is from rice, wheat, soy, maize, tomato, *Arabidopsis thaliana*, barley, rapeseed, cotton, sugarcane or beet.

28. The method of claim 26, wherein the constitutive, inducible or meiosis-specific promoter is a Spo11 promoter or a ubiquitin promoter.

29. The method of claim 21, wherein the nucleic acid encoding the one or more guide RNAs is operably linked to a polymerase III promoter.

30. The method of claim 29, wherein the polymerase III promoter is a U3 promoter or a U6 promoter.

31. The method of claim 1, wherein the bacterial Cas9 protein comprises a RuvC domain and an HNH domain.

32. The method of claim 21, further comprising:

regenerating a plant from the plant cell; and placing the plant in conditions to promote induction of a reproductive phase, thereby inducing expression of the fusion protein and the one or more guide RNAs.

33. The method of claim 21, wherein the transformation is achieved using a transient expression system.

* * * * *

SEQUENCE LISTING

```
<160> NUMBER OF SEQ ID NOS: 18

<210> SEQ ID NO 1
<211> LENGTH: 12349
<212> TYPE: DNA
<213> ORGANISM: Artificial Sequence
<220> FEATURE:
<223> OTHER INFORMATION: Plasmid P1 comprising a nucleic acid encoding
      the wild-type Cas9-Spo11 fusion protein
<220> FEATURE:
<221> NAME/KEY: promoter
<222> LOCATION: (1)..(397)
<223> OTHER INFORMATION: ADH1 promoter
```

<220> FEATURE:
<221> NAME/KEY: gene
<222> LOCATION: (431)..(5974)
<223> OTHER INFORMATION: Gene encoding the Cas9-Spo11 fusion protein
<220> FEATURE:
<221> NAME/KEY: terminator
<222> LOCATION: (6010)..(6198)
<223> OTHER INFORMATION: ADH1 terminator
<220> FEATURE:
<221> NAME/KEY: rep_origin
<222> LOCATION: (6605)..(7287)
<223> OTHER INFORMATION: ColE1 bacterial origin of replication
<220> FEATURE:
<221> NAME/KEY: gene
<222> LOCATION: (7385)..(8045)
<223> OTHER INFORMATION: Ampicillin-resistance gene
<220> FEATURE:
<221> NAME/KEY: gene
<222> LOCATION: (8809)..(9631)
<223> OTHER INFORMATION: TRP1 gene
<220> FEATURE:
<221> NAME/KEY: rep_origin
<222> LOCATION: (9688)..(10126)
<223> OTHER INFORMATION: F1 origin of replication
<220> FEATURE:
<221> NAME/KEY: gene
<222> LOCATION: (10344)..(11363)
<223> OTHER INFORMATION: G418-resistance gene (KanMx)

<400> SEQUENCE: 1
caacttcttt tcttttttttt tcttttctct ctccccgtt gttgtctcac catatccgca 60
atgacaaaaa aatgatggaa gacactaaag gaaaaaatta acgacaaaga cagcaccaac 120
agatgtcgtt gttccagagc tgatgagggg tatctcgaag cacacgaaac tttttccttc 180
cttcattcac gcacactact ctctaatgag caacggtata cggccttcct tccagttact 240
tgaatttgaa ataaaaaaaa gtttgctgtc ttgctatcaa gtataaatag acctgcaatt 300
attaatcttt tgtttcctcg tcattgttct cgttcccttt cttccttgtt tctttttctg 360
cacaatattt caagctatac caagcataca atcaactcca agcttgaagc aagcctcctg 420
aaagactagt atgggaaaac ctattcctaa tcctctgctg ggcctggatt ctaccggagg 480
catggcccct aagaaaaagc ggaaggtgga cggcggaggt attcatggag ttcctgctgc 540
gatggacaag aagtattcta tcggactgga tatcgggact aatagcgtcg ggtgggccgt 600
gatcactgac gagtacaagg tgccctctaa gaagttcaag gtgctcggga acaccgaccg 660
gcattccatc aagaaaaatc tgatcggagc tctcctcttt gattcagggg agaccgctga 720
agcaacccgc ctcaagcgga ctgctagacg gcggtacacc aggaggaaga accggatttg 780
ttaccttcaa gagatattct ccaacgaaat ggcaaaggtc gacgacagct tcttccatag 840
gctggaagaa tcattcctcg tggaagagga taagaagcat gaacggcatc ccatcttcgg 900
taatatcgtc gacgaggtgg cctatcacga gaaataccca accatctacc atcttcgcaa 960
aaagctggtg gactcaaccg acaaggcaga cctccggctt atctacctgg ccctggccca 1020
catgatcaag ttcagaggcc acttcctgat cgagggcgac ctcaatcctg acaatagcga 1080
tgtggataaa ctgttcatcc agctggtgca gacttacaac cagctctttg aagagaaccc 1140
catcaatgca agcggagtcg atgccaaggc cattctgtca gcccggctgt caaagagccg 1200
cagacttgag aatcttatcg ctcagctgcc gggtgaaaag aaaaatggac tgttcgggaa 1260
cctgattgct ctttcacttg ggctgactcc caatttcaag tctaatttcg acctggcaga 1320
ggatgccaag ctgcaactgt ccaaggacac ctatgatgac gatctcgaca acctcctggc 1380
ccagatcggt gaccaatacg ccgacctttt ccttgctgct aagaatcttt ctgacgccat 1440

-continued

```
cctgctgtct gacattctcc gcgtgaacac tgaaatcacc aaggcccctc tttcagcttc   1500
aatgattaag cggtatgatg agcaccacca ggacctgacc ctgcttaagg cactcgtccg   1560
gcagcagctt ccggagaagt acaaggaaat cttctttgac cagtcaaaga atggatacgc   1620
cggctacatc gacggaggtg cctcccaaga ggaattttat aagtttatca aacctatcct   1680
tgagaagatg gacggcaccg aagagctcct cgtgaaactg aatcgggagg atctgctgcg   1740
gaagcagcgc actttcgaca atgggagcat tccccaccag atccatcttg gggagcttca   1800
cgccatcctt cggcgccaag aggacttcta cccctttctt aaggacaaca gggagaagat   1860
tgagaaaatt ctcactttcc gcatccccta ctacgtggga cccctcgcca gaggaaatag   1920
ccggtttgct tggatgacca gaaagtcaga agaaactatc actccctgga acttcgaaga   1980
ggtggtggac aagggagcca gcgctcagtc attcatcgaa cggatgacta acttcgataa   2040
gaacctcccc aatgagaagg tcctgccgaa acattccctg ctctacgagt actttaccgt   2100
gtacaacgag ctgaccaagg tgaaatatgt caccgaaggg atgaggaagc ccgcattcct   2160
gtcaggcgaa caaaagaagg caattgtgga ccttctgttc aagaccaata gaaaggtgac   2220
cgtgaagcag ctgaaggagg actatttcaa gaaaattgaa tgcttcgact ctgtggagat   2280
tagcggggtc gaagatcggt tcaacgcaag cctgggtacc taccatgatc tgcttaagat   2340
catcaaggac aaggattttc tggacaatga ggagaacgag gacatccttg aggacattgt   2400
cctgactctc actctgttcg aggaccggga aatgatcgag gagaggctta agacctacgc   2460
ccatctgttc gacgataaag tgatgaagca acttaaacgg agaagatata ccggatgggg   2520
acgccttagc cgcaaactca tcaacggaat ccgggacaaa cagagcggaa agaccattct   2580
tgatttcctt aagagcgacg gattcgctaa tcgcaacttc atgcaactta tccatgatga   2640
ttccctgacc tttaaggagg acatccagaa ggcccaagtg tctggacaag gtgactcact   2700
gcacgagcat atcgcaaatc tggctggttc acccgctatt aagaagggta ttctccagac   2760
cgtgaaagtc gtggacgagc tggtcaaggt gatgggtcgc cataaaccag agaacattgt   2820
catcgagatg gccagggaaa accagactac ccagaaggga cagaagaaca gcagggagcg   2880
gatgaaaaga attgaggaag ggattaagga gctcgggtca cagatcctta aagagcaccc   2940
ggtggaaaac acccagcttc agaatgagaa gctctatctg tactaccttc aaaatggacg   3000
cgatatgtat gtggaccaag agcttgatat caacaggctc tcagactacg acgtggacca   3060
tatcgtccct cagagcttcc tcaaagacga ctcaattgac aataaggtgc tgactcgctc   3120
agacaagaac cggggaaagt cagataacgt gccctcagag gaagtcgtga aaaagatgaa   3180
gaactattgg cgccagcttc tgaacgcaaa gctgatcact cagcggaagt tcgacaatct   3240
cactaaggct gagagggggcg gactgagcga actggacaaa gcaggattca ttaaacggca   3300
acttgtggag actcggcaga ttactaaaca tgtcgcccaa atccttgact cacgcatgaa   3360
taccaagtac gacgaaaacg acaaacttat ccgcgaggtg aaggtgatta ccctgaagtc   3420
caagctggtc agcgatttca gaaaggactt tcaattctac aaagtgcggg agatcaataa   3480
ctatcatcat gctcatgacg catatctgaa tgccgtggtg ggaaccgccc tgatcaagaa   3540
gtacccaaag ctggaaagcg agttcgtgta cggagactac aaggtctacg acgtgcgcaa   3600
gatgattgcc aaatctgagc aggagatcgg aaaggccacc gcaaagtact tcttctacag   3660
caacatcatg aatttcttca agaccgaaat cacccttgca aacggtgaga tccggaagag   3720
gccgctcatc gagactaatg gggagactgg cgaaatcgtg tgggacaagg gcagagattt   3780
cgctaccgtg cgcaaagtgc tttctatgcc tcaagtgaac atcgtgaaga aaaccgaggt   3840
```

-continued

```
gcaaaccgga ggcttttcta aggaatcaat cctccccaag cgcaactccg acaagctcat   3900
tgcaaggaag aaggattggg accctaagaa gtacggcgga ttcgattcac caactgtggc   3960
ttattctgtc ctggtcgtgg ctaaggtgga aaaaggaaag tctaagaagc tcaagagcgt   4020
gaaggaactg ctgggtatca ccattatgga gcgcagctcc ttcgagaaga acccaattga   4080
ctttctcgaa gccaaaggtt acaaggaagt caagaaggac cttatcatca agctcccaaa   4140
gtatagcctg ttcgaactgg agaatgggcg gaagcggatg ctcgcctccg ctggcgaact   4200
tcagaagggt aatgagctgg ctctcccctc caagtacgtg aatttcctct accttgcaag   4260
ccattacgag aagctgaagg ggagccccga ggacaacgag caaaagcaac tgtttgtgga   4320
gcagcataag cattatctgg acgagatcat tgagcagatt tccgagtttt ctaaacgcgt   4380
cattctcgct gatgccaacc tcgataaagt ccttagcgca tacaataagc acagagacaa   4440
accaattcgg gagcaggctg agaatatcat ccacctgttc accctcacca atcttggtgc   4500
ccctgccgca ttcaagtact tcgacaccac catcgaccgg aaacgctata cctccaccaa   4560
agaagtgctg gacgccaccc tcatccacca gagcatcacc ggactttacg aaactcggat   4620
tgacctctca cagctcggag gggatccgga atttatggcc atggaggccc cggggatccg   4680
tatggctttg gagggattgc ggaaaaaata taaaacaagg caggaattgg tcaaagcact   4740
cactcctaaa agacggtcca ttcacttgaa ctccaatggt cactccaacg gaactccctg   4800
ttcaaacgca gatgttttgg ctcatattaa gcatttcctg tcattggcgg ctaattcatt   4860
agagcaacat caacagccta tttcaatcgt ctttcaaaac aaaaaaaaaa aaggcgatac   4920
aagcagtcct gacattcaca caacattgga cttccctttg aatggcccgc atctatgcac   4980
tcatcagttc aagttgaaaa gatgcgcaat ccttttaaac ttattgaaag tcgttatgga   5040
aaaattaccg ctaggtaaaa acactacagt gagagatatc ttctactcca acgtggaatt   5100
gtttcaaaga caagcaaacg tagtccagtg gctggacgtt atacgcttta atttcaagct   5160
ctctccaaga aaatccttaa acattatacc agctcaaaag ggtttagttt attcgccttt   5220
ccccattgat atttatgaca atattctgac atgtgaaaat gaaccaaaga tgcaaaagca   5280
aacaattttc cctggtaagc cctgtctaat tccatttttc caagatgatg cggtcatcaa   5340
gttagggaca acaagtatgt gtaatattgt aatagtggaa aaagaagctg tcttcaccaa   5400
attagtaaat aattatcaca agttgagtac aaataccatg ctcattacag gtaagggatt   5460
tccagatttc ttgacaaggt tattcctaaa aaaactagaa caatattgct ccaaattgat   5520
atcggactgt tctatattta ccgatgcgga cccctatggg attagcatag ccctaaatta   5580
tactcactcg aatgaacgca acgcttatat ttgcacgatg gcaaactata aaggaattcg   5640
tattacgcaa gttttggcac aaaataatga agtgcataac aaatccattc aattattgag   5700
tttgaatcag cgcgactact ccttagccaa gaatttgata gcatctctga ctgccaacag   5760
ctgggatatt gcaacttcac cattaaagaa cgtcatcata gaatgtcagc gggaaatttt   5820
tttccaaaag aaagctgaaa tgaacgagat tgatgccaga atttttgaat acaaatccca   5880
ccaccatcat catcacggag actacaagga tgacgatgac aaggactaca aggatgacga   5940
tgacaaggac tacaaggatg acgatgacaa gtaatgagtc gacaacccct gcagccaagc   6000
taattccggg cgaatttctt atgatttatg atttttatta ttaaataagt tataaaaaaa   6060
ataagtgtat acaaatttta aagtgactct taggttttaa aacgaaaatt cttgttcttg   6120
agtaactctt tcctgtaggt caggttgctt tctcaggtat agcatgaggt cgctcttatt   6180
```

-continued

```
gaccacacct ctaccggcat gcaagcttgg cgtaatcatg gtcatagctg tttcctgtgt   6240
gaaattgtta tccgctcaca attccacaca acatacgagc cggaagcata aagtgtaaag   6300
cctggggtgc ctaatgagtg aggtaactca cattaattgc gttgcgctca ctgcccgctt   6360
tccagtcggg aaacctgtcg tgccagctgg attaatgaat cggccaacgc gcggggagag   6420
gcggtttgcg tattgggcgc tcttccgctt cctcgctcac tgactcgctg cgctcggtcg   6480
ttcggctgcg gcgagcggta tcagctcact caaaggcggt aatacggtta tccacagaat   6540
caggggataa cgcaggaaag aacatgtgag caaaaggcca gcaaaaggcc aggaaccgta   6600
aaaaggccgc gttgctggcg tttttccata ggctccgccc ccctgacgag catcacaaaa   6660
atcgacgctc aagtcagagg tggcgaaacc cgacaggact ataaagatac caggcgtttc   6720
cccctggaag ctccctcgtg cgctctcctg ttccgaccct gccgcttacc ggatacctgt   6780
ccgcctttct cccttcggga agcgtggcgc tttctcatag ctcacgctgt aggtatctca   6840
gttcggtgta ggtcgttcgc tccaagctgg gctgtgtgca cgaacccccc gttcagcccg   6900
accgctgcgc cttatccggt aactatcgtc ttgagtccaa cccggtaaga cacgacttat   6960
cgccactggc agcagccact ggtaacagga ttagcagagc gaggtatgta ggcggtgcta   7020
cagagttctt gaagtggtgg cctaactacg gctacactag aaggacagta tttggtatct   7080
gcgctctgct gaagccagtt accttcggaa aaagagttgg tagctcttga tccggcaaac   7140
aaaccaccgc tggtagcggt ggtttttttg tttgcaagca gcagattacg cgcagaaaaa   7200
aaggatctca agaagatcct ttgatctttt ctacggggtc tgacgctcag tggaacgaaa   7260
actcacgtta agggattttg gtcatgagat tatcaaaaag gatcttcacc tagatccttt   7320
taaattaaaa atgaagtttt aaatcaatct aaagtatata tgagtaaact tggtctgaca   7380
gttaccaatg cttaatcagt gaggcaccta tctcagcgat ctgtctattt cgttcatcca   7440
tagttgcctg actccccgtc gtgtagataa ctacgatacg ggagggctta ccatctggcc   7500
ccagtgctgc aatgataccg cgagacccac gctcaccggc tccagattt atcagcaata    7560
aaccagccag ccggaagggc cgagcgcaga agtggtcctg caactttatc cgcctccatc   7620
cagtctatta attgttgccg ggaagctaga gtaagtagtt cgccagttaa tagtttgcgc   7680
aacgttgttg ccattgctac aggcatcgtg gtgtcacgct cgtcgtttgg tatggcttca   7740
ttcagctccg gttcccaacg atcaaggcga gttacatgat cccccatgtt gtgcaaaaaa   7800
gcggttagct ccttcggtcc tccgatcgtt gtcagaagta agttggccgc agtgttatca   7860
ctcatggtta tggcagcact gcataattct cttactgtca tgccatccgt aagatgcttt   7920
tctgtgactg gtgagtactc aaccaagtca ttctgagaat agtgtatgcg gcgaccgagt   7980
tgctcttgcc cggcgtcaat acgggataat accgcgccac atagcagaac tttaaaagtg   8040
ctcatcattg gaaaacgttc ttcggggcga aaactctcaa ggatcttacc gctgttgaga   8100
tccagttcga tgtaacccac tcgtgcaccc aactgatctt cagcatcttt tactttcacc   8160
agcgtttctg ggtgagcaaa aacaggaagg caaaatgccg caaaaaaggg aataagggcg   8220
acacggaaat gttgaatact catactcttc ctttttcaat attattgaag catttatcag   8280
ggttattgtc tcatgagcgg atacatattt gaatgtattt agaaaaataa acaaataggg   8340
gttccgcgca catttccccg aaaagtgcca cctgacgtct aagaaaccat tattatcatg   8400
acattaacct ataaaaatag gcgtatcacg aggccctttc gtctcgcgcg tttcggtgat   8460
gacggtgaaa acctctgaca catgcagctc ccggagacgg tcacagcttg tctgtaagcg   8520
gatgccggga gcagacaagc ccgtcagggc gcgtcagcgg gtgttggcgg gtgtcggggc   8580
```

-continued

```
tggcttaact atgcggcatc agagcagatt gtactgagag tgcaccataa acgacattac   8640
tatatatata atataggaag catttaatag acagcatcgt aatatatgtg tactttgcag   8700
ttatgacgcc agatggcagt agtggaagat attctttatt gaaaaatagc ttgtcacctt   8760
acgtacaatc ttgatccgga gcttttcttt ttttgccgat taagaattaa ttcggtcgaa   8820
aaaagaaaag gagagggcca agagggaggg cattggtgac tattgagcac gtgagtatac   8880
gtgattaagc acacaaaggc agcttggagt atgtctgtta ttaatttcac aggtagttct   8940
ggtccattgg tgaaagtttg cggcttgcag agcacagagg ccgcagaatg tgctctagat   9000
tccgatgctg acttgctggg tattatatgt gtgcccaata gaaagagaac aattgacccg   9060
gttattgcaa ggaaaatttc aagtcttgta aaagcatata aaaatagttc aggcactccg   9120
aaatacttgg ttggcgtgtt tcgtaatcaa cctaaggagg atgttttggc tctggtcaat   9180
gattacggca ttgatatcgt ccaactgcat ggagatgagt cgtggcaaga ataccaagag   9240
ttcctcggtt tgccagttat taaaagactc gtatttccaa aagactgcaa catactactc   9300
agtgcagctt cacagaaacc tcattcgttt attcccttgt ttgattcaga agcaggtggg   9360
acaggtgaac ttttggattg gaactcgatt tctgactggg ttggaaggca agagagcccc   9420
gaaagcttac attttatgtt agctggtgga ctgacgccag aaaatgttgg tgatgcgctt   9480
agattaaatg gcgttattgg tgttgatgta agcggaggtg tggagacaaa tggtgtaaaa   9540
gactctaaca aaatagcaaa tttcgtcaaa aatgctaaga aataggttat tactgagtag   9600
tatttattta agtattgttt gtgcacttgc cgatctatgc ggtgtgaaat accgcacaga   9660
tgcgtaagga gaaaataccg catcaggaaa ttgtaaacgt taatattttg ttaaaattcg   9720
cgttaaattt ttgttaaatc agctcatttt ttaaccaata ggccgaaatc ggcaaaatcc   9780
cttataaatc aaaagaatag accgagatag ggttgagtgt tgttccagtt tggaacaaga   9840
gtccactatt aaagaacgtg gactccaacg tcaaagggcg aaaaaccgtc tatcagggcg   9900
atggcccact acgtgaacca tcaccctaat caagtttttt ggggtcgagg tgccgtaaag   9960
cactaaatcg gaaccctaaa gggagccccc gatttagagc ttgacgggga aagccggcga  10020
acgtggcgag aaaggaaggg aagaaagcga aaggagcggg cgctagggcg ctggcaagtg  10080
tagcggtcac gctgcgcgta accaccacac ccgccgcgct taatgcgccg ctacagggcg  10140
cgtcgcgcca ttcgccattc aggctgcgca actgttggga agggcgatcg gtgcgggcct  10200
cttcgctatt acgccagctg gcgaaagggg gatgtgctgc aaggcgatta agttgggtaa  10260
cgccagggtt ttcccagtca cgacgttgta aaacgacggc cagtcgtcca agctttcgat  10320
catcgatgaa ttcgagctcg ttttcgacag cagtatagcg accagcattc acatacgatt  10380
gacgcatgat attactttct gcgcacttaa cttcgcatct gggcagatga tgtcgaggcg  10440
aaaaaaaata taaatcacgc taacatttga ttaaaataga acaactacaa tataaaaaaa  10500
ctatacaaat gacaagttct tgaaaacaag aatcttttta ttgtcagtac tgattagaaa  10560
aactcatcga gcatcaaatg aaactgcaat ttattcatat caggattatc aataccatat  10620
ttttgaaaaa gccgtttctg taatgaagga gaaaactcac cgaggcagtt ccataggatg  10680
gcaagatcct ggtatcggtc tgcgattccg actcgtccaa catcaataca acctattaat  10740
ttcccctcgt caaaaataag gttatcaagt gagaaatcac catgagtgac gactgaatcc  10800
ggtgagaatg gcaaaagctt atgcatttct ttccagactt gttcaacagg ccagccatta  10860
cgctcgtcat caaaatcact cgcatcaacc aaaccgttat tcattcgtga ttgcgcctga  10920
```

```
gcgagacgaa atacgcgatc gctgttaaaa ggacaattac aaacaggaat cgaatgcaac  10980
cggcgcagga acactgccag cgcatcaaca atattttcac ctgaatcagg atattcttct  11040
aatacctgga atgctgtttt gccggggatc gcagtggtga gtaaccatgc atcatcagga  11100
gtacggataa aatgcttgat ggtcggaaga ggcataaatt ccgtcagcca gtttagtctg  11160
accatctcat ctgtaacatc attggcaacg ctacctttgc catgtttcag aaacaactct  11220
ggcgcatcgg gcttcccata caatcgatag attgtcgcac ctgattgccc gacattatcg  11280
cgagcccatt tatacccata taaatcagca tccatgttgg aatttaatcg cggcctcgaa  11340
acgtgagtct tttccttacc catggttgtt tatgttcgga tgtgatgtga gaactgtatc  11400
ctagcaagat tttaaaagga agtatatgaa agaagaacct cagtggcaaa tcctaacctt  11460
ttatatttct ctacaggggc gcggcgtggg gacaattcaa cgcgtctgtg aggggagcgt  11520
ttccctgctc gcaggtctgc agcgaggagc cgtaattttt gcttcgcgcc gtgcggccat  11580
caaaatgtat ggatgcaaat gattatacat ggggatgtat gggctaaatg tacgggcgac  11640
agtcacatca tgcccctgag ctgcgcacgt caagactgtc aaggagggta ttctgggcct  11700
ccatgtcgct ggccgggtga cccggcgggg acgaggcaag ctaaacagat ctggcgcgcc  11760
ttaattaacc ccgagctcga gatcccgagc ttgcaaatta aagccttcga gcgtcccaaa  11820
accttctcaa gcaaggtttt cagtataatg ttacatgcgt acacgcgtct gtacagaaaa  11880
aaaagaaaaa tttgaaatat aaataacgtt cttaatacta acataactat aaaaaaataa  11940
atagggacct agacttcagg ttgtctaact ccttcctttt cggttagagc ggatgtgggg  12000
ggagggcgtg aatgtaagcg tgacataact aattacatga tatccttttg ttgtttccgg  12060
gtgtacaata tggacttcct cttttctggc aaccaaaccc atacatcggg attcctataa  12120
taccttcgtt ggtctcccta acatgtaggt ggcggagggg agatatacaa tagaacagat  12180
accagacaag acataatggg ctaaacaaaa ctacaccaat tacactgcct cattgatggt  12240
ggtacataac gaactaatac tgtagcccta gacttgatag ccatcatcat atcgaagttt  12300
cactaccctt tttccatttg ccatctattg aagtaataat aggcgcatg             12349
```

<210> SEQ ID NO 2
<211> LENGTH: 12349
<212> TYPE: DNA
<213> ORGANISM: Artificial Sequence
<220> FEATURE:
<223> OTHER INFORMATION: Plasmid P2 comprising a nucleic acid encoding the Cas9*-Spo11 fusion protein
<220> FEATURE:
<221> NAME/KEY: promoter
<222> LOCATION: (1)..(397)
<223> OTHER INFORMATION: ADH1 promoter
<220> FEATURE:
<221> NAME/KEY: gene
<222> LOCATION: (431)..(5974)
<223> OTHER INFORMATION: Gene encoding the Ca9*-Spo11 fusion protein
<220> FEATURE:
<221> NAME/KEY: terminator
<222> LOCATION: (6010)..(6198)
<223> OTHER INFORMATION: ADH1 terminator
<220> FEATURE:
<221> NAME/KEY: rep_origin
<222> LOCATION: (6605)..(7287)
<223> OTHER INFORMATION: ColE1 bacterial origin of replication
<220> FEATURE:
<221> NAME/KEY: gene
<222> LOCATION: (7385)..(8045)
<223> OTHER INFORMATION: Ampicillin-resistance gene
<220> FEATURE:
<221> NAME/KEY: gene
<222> LOCATION: (8809)..(9631)

-continued

<223> OTHER INFORMATION: TRP1 gene
<220> FEATURE:
<221> NAME/KEY: rep_origin
<222> LOCATION: (9688)..(10126)
<223> OTHER INFORMATION: F1 origin of replication
<220> FEATURE:
<221> NAME/KEY: gene
<222> LOCATION: (10344)..(11363)
<223> OTHER INFORMATION: G418-resistance gene (KanMX)

<400> SEQUENCE: 2

```
caacttcttt tcttttttt tcttttctct ctcccccgtt gttgtctcac catatccgca     60
atgacaaaaa aatgatggaa gacactaaag gaaaaaatta acgacaaaga cagcaccaac    120
agatgtcgtt gttccagagc tgatgagggg tatctcgaag cacacgaaac tttttccttc    180
cttcattcac gcacactact ctctaatgag caacggtata cggccttcct tccagttact    240
tgaatttgaa ataaaaaaaa gtttgctgtc ttgctatcaa gtataaatag acctgcaatt    300
attaatcttt tgtttcctcg tcattgttct cgttcccttt cttccttgtt tctttttctg    360
cacaatattt caagctatac caagcataca atcaactcca agcttgaagc aagcctcctg    420
aaagactagt atgggaaaac ctattcctaa tcctctgctg ggcctggatt ctaccggagg    480
catggcccct aagaaaaagc ggaaggtgga cggcggaggt attcatggag ttcctgctgc    540
gatggacaag aagtattcta tcggactggc catcgggact aatagcgtcg ggtgggccgt    600
gatcactgac gagtacaagg tgccctctaa gaagttcaag gtgctcggga acaccgaccg    660
gcattccatc aagaaaaatc tgatcggagc tctcctcttt gattcagggg agaccgctga    720
agcaacccgc ctcaagcgga ctgctagacg gcggtacacc aggaggaaga accggatttg    780
ttaccttcaa gagatattct ccaacgaaat ggcaaaggtc gacgacagct tcttccatag    840
gctggaagaa tcattcctcg tggaagagga taagaagcat gaacggcatc ccatcttcgg    900
taatatcgtc gacgaggtgg cctatcacga gaaataccca accatctacc atcttcgcaa    960
aaagctggtg gactcaaccg acaaggcaga cctccggctt atctacctgg ccctggccca   1020
catgatcaag ttcagaggcc acttcctgat cgagggcgac ctcaatcctg acaatagcga   1080
tgtggataaa ctgttcatcc agctggtgca gacttacaac cagctctttg aagagaaccc   1140
catcaatgca agcggagtcg atgccaaggc cattctgtca gcccggctgt caaagagccg   1200
cagacttgag aatcttatcg ctcagctgcc gggtgaaaag aaaaatggac tgttcgggaa   1260
cctgattgct ctttcacttg ggctgactcc caatttcaag tctaatttcg acctggcaga   1320
ggatgccaag ctgcaactgt ccaaggacac ctatgatgac gatctcgaca acctcctggc   1380
ccagatcggt gaccaatacg ccgacctttt ccttgctgct aagaatcttt ctgacgccat   1440
cctgctgtct gacattctcc gcgtgaacac tgaaatcacc aaggcccctc tttcagcttc   1500
aatgattaag cggtatgatg agcaccacca ggacctgacc ctgcttaagg cactcgtccg   1560
gcagcagctt ccggagaagt acaaggaaat cttctttgac cagtcaaaga atggatacgc   1620
cggctacatc gacggaggtg cctcccaaga ggaattttat aagtttatca aacctatcct   1680
tgagaagatg gacggcaccg aagagctcct cgtgaaactg aatcgggagg atctgctgcg   1740
gaagcagcgc actttcgaca atgggagcat tccccaccag atccatcttg gggagcttca   1800
cgccatcctt cggcgccaag aggacttcta cccctttctt aaggacaaca gggagaagat   1860
tgagaaaatt ctcactttcc gcatccccta ctacgtggga cccctcgcca gaggaaatag   1920
ccggtttgct tggatgacca gaaagtcaga agaaactatc actccctgga acttcgaaga   1980
ggtggtggac aagggagcca gcgctcagtc attcatcgaa cggatgacta acttcgataa   2040
```

-continued gaacctcccc aatgagaagg tcctgccgaa acattccctg ctctacgagt actttaccgt 2100
gtacaacgag ctgaccaagg tgaaatatgt caccgaaggg atgaggaagc ccgcattcct 2160
gtcaggcgaa caaaagaagg caattgtgga ccttctgttc aagaccaata gaaaggtgac 2220
cgtgaagcag ctgaaggagg actatttcaa gaaaattgaa tgcttcgact ctgtggagat 2280
tagcggggtc gaagatcggt tcaacgcaag cctgggtacc taccatgatc tgcttaagat 2340
catcaaggac aaggattttc tggacaatga ggagaacgag gacatccttg aggacattgt 2400
cctgactctc actctgttcg aggaccggga aatgatcgag gagaggctta agacctacgc 2460
ccatctgttc gacgataaag tgatgaagca acttaaacgg agaagatata ccggatgggg 2520
acgccttagc cgcaaactca tcaacggaat ccgggacaaa cagagcggaa agaccattct 2580
tgatttcctt aagagcgacg gattcgctaa tcgcaacttc atgcaactta tccatgatga 2640
ttccctgacc tttaaggagg acatccagaa ggcccaagtg tctggacaag gtgactcact 2700
gcacgagcat atcgcaaatc tggctggttc acccgctatt aagaagggta ttctccagac 2760
cgtgaaagtc gtggacgagc tggtcaaggt gatgggtcgc cataaaccag agaacattgt 2820
catcgagatg gccagggaaa accagactac ccagaaggga cagaagaaca gcagggagcg 2880
gatgaaaaga attgaggaag ggattaagga gctcgggtca cagatcctta aagagcaccc 2940
ggtggaaaac acccagcttc agaatgagaa gctctatctg tactaccttc aaaatggacg 3000
cgatatgtat gtggaccaag agcttgatat caacaggctc tcagactacg acgtggacgc 3060
tatcgtccct cagagcttcc tcaaagacga ctcaattgac aataaggtgc tgactcgctc 3120
agacaagaac cggggaaagt cagataacgt gccctcagag gaagtcgtga aaaagatgaa 3180
gaactattgg cgccagcttc tgaacgcaaa gctgatcact cagcggaagt tcgacaatct 3240
cactaaggct gagaggggcg gactgagcga actggacaaa gcaggattca ttaaacggca 3300
acttgtggag actcggcaga ttactaaaca tgtcgcccaa atccttgact cacgcatgaa 3360
taccaagtac gacgaaaacg acaaacttat ccgcgaggtg aaggtgatta ccctgaagtc 3420
caagctggtc agcgatttca gaaaggactt tcaattctac aaagtgcggg agatcaataa 3480
ctatcatcat gctcatgacg catatctgaa tgccgtggtg ggaaccgccc tgatcaagaa 3540
gtacccaaag ctggaaagcg agttcgtgta cggagactac aaggtctacg acgtgcgcaa 3600
gatgattgcc aaatctgagc aggagatcgg aaaggccacc gcaaagtact tcttctacag 3660
caacatcatg aatttcttca agaccgaaat caccettgca aacggtgaga tccggaagag 3720
gccgctcatc gagactaatg gggagactgg cgaaatcgtg tgggacaagg gcagagattt 3780
cgctaccgtg cgcaaagtgc tttctatgcc tcaagtgaac atcgtgaaga aaaccgaggt 3840
gcaaaccgga ggcttttcta aggaatcaat cctccccaag cgcaactccg acaagctcat 3900
tgcaaggaag aaggattggg accctaagaa gtacggcgga ttcgattcac caactgtggc 3960
ttattctgtc ctggtcgtgg ctaaggtgga aaaaggaaag tctaagaagc tcaagagcgt 4020
gaaggaactg ctgggtatca ccattatgga gcgcagctcc ttcgagaaga acccaattga 4080
ctttctcgaa gccaaaggtt acaaggaagt caagaaggac cttatcatca agctcccaaa 4140
gtatagcctg ttcgaactgg agaatgggcg gaagcggatg ctcgcctccg ctggcgaact 4200
tcagaagggt aatgagctgg ctctcccctc caagtacgtg aatttcctct accttgcaag 4260
ccattacgag aagctgaagg ggagccccga ggacaacgag caaaagcaac tgtttgtgga 4320
gcagcataag cattatctgg acgagatcat tgagcagatt tccgagtttt ctaaacgcgt 4380

-continued

```
cattctcgct gatgccaacc tcgataaagt ccttagcgca tacaataagc acagagacaa   4440
accaattcgg gagcaggctg agaatatcat ccacctgttc accctcacca atcttggtgc   4500
ccctgccgca ttcaagtact tcgacaccac catcgaccgg aaacgctata cctccaccaa   4560
agaagtgctg gacgccaccc tcatccacca gagcatcacc ggactttacg aaactcggat   4620
tgacctctca cagctcggag gggatccgga atttatggcc atggaggccc cggggatccg   4680
tatggctttg gagggattgc ggaaaaaata taaaacaagg caggaattgg tcaaagcact   4740
cactcctaaa agacggtcca ttcacttgaa ctccaatggt cactccaacg gaactccctg   4800
ttcaaacgca gatgttttgg ctcatattaa gcatttcctg tcattggcgg ctaattcatt   4860
agagcaacat caacagccta tttcaatcgt ctttcaaaac aaaaaaaaaa aaggcgatac   4920
aagcagtcct gacattcaca caacattgga cttccctttg aatggcccgc atctatgcac   4980
tcatcagttc aagttgaaaa gatgcgcaat ccttttaaac ttattgaaag tcgttatgga   5040
aaaattaccg ctaggtaaaa acactacagt gagagatatc ttctactcca acgtggaatt   5100
gtttcaaaga caagcaaacg tagtccagtg gctggacgtt atacgcttta atttcaagct   5160
ctctccaaga aaatccttaa acattatacc agctcaaaag ggtttagttt attcgccttt   5220
ccccattgat atttatgaca atattctgac atgtgaaaat gaaccaaaga tgcaaaagca   5280
aacaattttc cctggtaagc cctgtctaat tccatttttc caagatgatg cggtcatcaa   5340
gttagggaca acaagtatgt gtaatattgt aatagtggaa aaagaagctg tcttcaccaa   5400
attagtaaat aattatcaca agttgagtac aaataccatg ctcattacag gtaagggatt   5460
tccagatttc ttgacaaggt tattcctaaa aaaactagaa caatattgct ccaaattgat   5520
atcggactgt tctatattta ccgatgcgga cccctatggg attagcatag ccctaaatta   5580
tactcactcg aatgaacgca acgcttatat ttgcacgatg gcaaactata aaggaattcg   5640
tattacgcaa gttttggcac aaaataatga agtgcataac aaatccattc aattattgag   5700
tttgaatcag cgcgactact ccttagccaa gaatttgata gcatctctga ctgccaacag   5760
ctgggatatt gcaacttcac cattaaagaa cgtcatcata gaatgtcagc gggaaatttt   5820
tttccaaaag aaagctgaaa tgaacgagat tgatgccaga atttttgaat acaaatccca   5880
ccaccatcat catcacggag actacaagga tgacgatgac aaggactaca aggatgacga   5940
tgacaaggac tacaaggatg acgatgacaa gtaatgagtc gacaacccct gcagccaagc   6000
taattccggg cgaatttctt atgatttatg atttttatta ttaaataagt tataaaaaaa   6060
ataagtgtat acaaatttta aagtgactct taggttttaa aacgaaaatt cttgttcttg   6120
agtaactctt tcctgtaggt caggttgctt tctcaggtat agcatgaggt cgctcttatt   6180
gaccacacct ctaccggcat gcaagcttgg cgtaatcatg gtcatagctg tttcctgtgt   6240
gaaattgtta tccgctcaca attccacaca acatacgagc cggaagcata aagtgtaaag   6300
cctggggtgc ctaatgagtg aggtaactca cattaattgc gttgcgctca ctgcccgctt   6360
tccagtcggg aaacctgtcg tgccagctgg attaatgaat cggccaacgc gcggggagag   6420
gcggtttgcg tattgggcgc tcttccgctt cctcgctcac tgactcgctg cgctcggtcg   6480
ttcggctgcg gcgagcggta tcagctcact caaaggcggt aatacggtta tccacagaat   6540
caggggataa cgcaggaaag aacatgtgag caaaaggcca gcaaaaggcc aggaaccgta   6600
aaaaggccgc gttgctggcg tttttccata ggctccgccc ccctgacgag catcacaaaa   6660
atcgacgctc aagtcagagg tggcgaaacc cgacaggact ataaagatac caggcgtttc   6720
cccctggaag ctccctcgtg cgctctcctg ttccgaccct gccgcttacc ggatacctgt   6780
```

-continued

```
ccgcctttct cccttcggga agcgtggcgc tttctcatag ctcacgctgt aggtatctca   6840
gttcggtgta ggtcgttcgc tccaagctgg gctgtgtgca cgaacccccc gttcagcccg   6900
accgctgcgc cttatccggt aactatcgtc ttgagtccaa cccggtaaga cacgacttat   6960
cgccactggc agcagccact ggtaacagga ttagcagagc gaggtatgta ggcggtgcta   7020
cagagttctt gaagtggtgg cctaactacg gctacactag aaggacagta tttggtatct   7080
gcgctctgct gaagccagtt accttcggaa aaagagttgg tagctcttga tccggcaaac   7140
aaaccaccgc tggtagcggt ggtttttttg tttgcaagca gcagattacg cgcagaaaaa   7200
aaggatctca agaagatcct ttgatctttt ctacggggtc tgacgctcag tggaacgaaa   7260
actcacgtta agggattttg gtcatgagat tatcaaaaag gatcttcacc tagatccttt   7320
taaattaaaa atgaagtttt aaatcaatct aaagtatata tgagtaaact tggtctgaca   7380
gttaccaatg cttaatcagt gaggcaccta tctcagcgat ctgtctattt cgttcatcca   7440
tagttgcctg actccccgtc gtgtagataa ctacgatacg ggagggctta ccatctggcc   7500
ccagtgctgc aatgataccg cgagacccac gctcaccggc tccagattt atcagcaata   7560
aaccagccag ccggaagggc cgagcgcaga agtggtcctg caactttatc cgcctccatc   7620
cagtctatta attgttgccg ggaagctaga gtaagtagtt cgccagttaa tagtttgcgc   7680
aacgttgttg ccattgctac aggcatcgtg gtgtcacgct cgtcgtttgg tatggcttca   7740
ttcagctccg gttcccaacg atcaaggcga gttacatgat cccccatgtt gtgcaaaaaa   7800
gcggttagct ccttcggtcc tccgatcgtt gtcagaagta agttggccgc agtgttatca   7860
ctcatggtta tggcagcact gcataattct cttactgtca tgccatccgt aagatgcttt   7920
tctgtgactg gtgagtactc aaccaagtca ttctgagaat agtgtatgcg gcgaccgagt   7980
tgctcttgcc cggcgtcaat acgggataat accgcgccac atagcagaac tttaaaagtg   8040
ctcatcattg gaaaacgttc ttcggggcga aaactctcaa ggatcttacc gctgttgaga   8100
tccagttcga tgtaacccac tcgtgcaccc aactgatctt cagcatcttt tactttcacc   8160
agcgtttctg ggtgagcaaa aacaggaagg caaaatgccg caaaaaaggg aataagggcg   8220
acacggaaat gttgaatact catactcttc ctttttcaat attattgaag catttatcag   8280
ggttattgtc tcatgagcgg atacatattt gaatgtattt agaaaaataa acaaataggg   8340
gttccgcgca catttccccg aaaagtgcca cctgacgtct aagaaaccat tattatcatg   8400
acattaacct ataaaaatag gcgtatcacg aggccctttc gtctcgcgcg tttcggtgat   8460
gacggtgaaa acctctgaca catgcagctc ccggagacgg tcacagcttg tctgtaagcg   8520
gatgccggga gcagacaagc ccgtcagggc gcgtcagcgg gtgttggcgg gtgtcggggc   8580
tggcttaact atgcggcatc agagcagatt gtactgagag tgcaccataa acgacattac   8640
tatatatata atataggaag catttaatag acagcatcgt aatatatgtg tactttgcag   8700
ttatgacgcc agatggcagt agtggaagat attctttatt gaaaaatagc ttgtcacctt   8760
acgtacaatc ttgatccgga gcttttcttt ttttgccgat taagaattaa ttcggtcgaa   8820
aaaagaaaag gagagggcca agagggaggg cattggtgac tattgagcac gtgagtatac   8880
gtgattaagc acacaaaggc agcttggagt atgtctgtta ttaatttcac aggtagttct   8940
ggtccattgg tgaaagtttg cggcttgcag agcacagagg ccgcagaatg tgctctagat   9000
tccgatgctg acttgctggg tattatatgt gtgcccaata gaaagagaac aattgacccg   9060
gttattgcaa ggaaaatttc aagtcttgta aaagcatata aaaatagttc aggcactccg   9120
```

-continued

```
aaatacttgg ttggcgtgtt tcgtaatcaa cctaaggagg atgttttggc tctggtcaat    9180
gattacggca ttgatatcgt ccaactgcat ggagatgagt cgtggcaaga ataccaagag    9240
ttcctcggtt tgccagttat taaaagactc gtatttccaa aagactgcaa catactactc    9300
agtgcagctt cacagaaacc tcattcgttt attcccttgt ttgattcaga agcaggtggg    9360
acaggtgaac ttttggattg gaactcgatt tctgactggg ttggaaggca agagagcccc    9420
gaaagcttac attttatgtt agctggtgga ctgacgccag aaaatgttgg tgatgcgctt    9480
agattaaatg gcgttattgg tgttgatgta agcggaggtg tggagacaaa tggtgtaaaa    9540
gactctaaca aaatagcaaa tttcgtcaaa aatgctaaga aataggttat tactgagtag    9600
tatttattta agtattgttt gtgcacttgc cgatctatgc ggtgtgaaat accgcacaga    9660
tgcgtaagga gaaaataccg catcaggaaa ttgtaaacgt taatattttg ttaaaattcg    9720
cgttaaattt ttgttaaatc agctcatttt ttaaccaata ggccgaaatc ggcaaaatcc    9780
cttataaatc aaaagaatag accgagatag ggttgagtgt tgttccagtt tggaacaaga    9840
gtccactatt aaagaacgtg gactccaacg tcaaagggcg aaaaaccgtc tatcagggcg    9900
atggcccact acgtgaacca tcaccctaat caagtttttt ggggtcgagg tgccgtaaag    9960
cactaaatcg gaaccctaaa gggagccccc gatttagagc ttgacgggga aagccggcga   10020
acgtggcgag aaaggaaggg aagaaagcga aaggagcggg cgctagggcg ctggcaagtg   10080
tagcggtcac gctgcgcgta accaccacac ccgccgcgct taatgcgccg ctacagggcg   10140
cgtcgcgcca ttcgccattc aggctgcgca actgttggga agggcgatcg gtgcgggcct   10200
cttcgctatt acgccagctg gcgaaagggg gatgtgctgc aaggcgatta agttgggtaa   10260
cgccagggtt ttcccagtca cgacgttgta aaacgacggc cagtcgtcca agctttcgat   10320
catcgatgaa ttcgagctcg ttttcgacag cagtatagcg accagcattc acatacgatt   10380
gacgcatgat attactttct gcgcacttaa cttcgcatct gggcagatga tgtcgaggcg   10440
aaaaaaaata taaatcacgc taacatttga ttaaaataga acaactacaa tataaaaaaa   10500
ctatacaaat gacaagttct tgaaaacaag aatcttttta ttgtcagtac tgattagaaa   10560
aactcatcga gcatcaaatg aaactgcaat ttattcatat caggattatc aataccatat   10620
ttttgaaaaa gccgtttctg taatgaagga gaaaactcac cgaggcagtt ccataggatg   10680
gcaagatcct ggtatcggtc tgcgattccg actcgtccaa catcaataca acctattaat   10740
ttcccctcgt caaaaataag gttatcaagt gagaaatcac catgagtgac gactgaatcc   10800
ggtgagaatg gcaaaagctt atgcatttct ttccagactt gttcaacagg ccagccatta   10860
cgctcgtcat caaaatcact cgcatcaacc aaaccgttat tcattcgtga ttgcgcctga   10920
gcgagacgaa atacgcgatc gctgttaaaa ggacaattac aaacaggaat cgaatgcaac   10980
cggcgcagga acactgccag cgcatcaaca atattttcac ctgaatcagg atattcttct   11040
aatacctgga atgctgtttt gccggggatc gcagtggtga gtaaccatgc atcatcagga   11100
gtacggataa aatgcttgat ggtcggaaga ggcataaatt ccgtcagcca gtttagtctg   11160
accatctcat ctgtaacatc attggcaacg ctacctttgc catgtttcag aaacaactct   11220
ggcgcatcgg gcttcccata caatcgatag attgtcgcac ctgattgccc gacattatcg   11280
cgagcccatt tatacccata taaatcagca tccatgttgg aatttaatcg cggcctcgaa   11340
acgtgagtct tttccttacc catggttgtt tatgttcgga tgtgatgtga gaactgtatc   11400
ctagcaagat tttaaaagga agtatatgaa agaagaacct cagtggcaaa tcctaacctt   11460
ttatatttct ctacaggggc gcggcgtggg gacaattcaa cgcgtctgtg aggggagcgt   11520
```

-continued

```
ttccctgctc gcaggtctgc agcgaggagc cgtaattttt gcttcgcgcc gtgcggccat  11580

caaaatgtat ggatgcaaat gattatacat ggggatgtat gggctaaatg tacgggcgac  11640

agtcacatca tgcccctgag ctgcgcacgt caagactgtc aaggagggta ttctgggcct  11700

ccatgtcgct ggccgggtga cccggcgggg acgaggcaag ctaaacagat ctggcgcgcc  11760

ttaattaacc ccgagctcga gatcccgagc ttgcaaatta aagccttcga gcgtcccaaa  11820

accttctcaa gcaaggtttt cagtataatg ttacatgcgt acacgcgtct gtacagaaaa  11880

aaaagaaaaa tttgaaatat aaataacgtt cttaatacta acataactat aaaaaaataa  11940

atagggacct agacttcagg ttgtctaact ccttcctttt cggttagagc ggatgtgggg  12000

ggagggcgtg aatgtaagcg tgacataact aattacatga tatccttttg ttgtttccgg  12060

gtgtacaata tggacttcct cttttctggc aaccaaaccc atacatcggg attcctataa  12120

taccttcgtt ggtctcccta acatgtaggt ggcggagggg agatatacaa tagaacagat  12180

accagacaag acataatggg ctaaacaaaa ctacaccaat tacactgcct cattgatggt  12240

ggtacataac gaactaatac tgtagcccta gacttgatag ccatcatcat atcgaagttt  12300

cactaccctt tttccatttg ccatctattg aagtaataat aggcgcatg             12349
```

<210> SEQ ID NO 3
<211> LENGTH: 7
<212> TYPE: PRT
<213> ORGANISM: Artificial Sequence
<220> FEATURE:
<223> OTHER INFORMATION: Nuclear localization signal sequence

<400> SEQUENCE: 3

```
Pro Lys Lys Lys Arg Lys Val
1               5
```

<210> SEQ ID NO 4
<211> LENGTH: 20
<212> TYPE: PRT
<213> ORGANISM: HIV-I

<400> SEQUENCE: 4

```
Gly Arg Lys Lys Arg Arg Gln Arg Arg Arg Pro Pro Gln Pro Lys Lys
1               5                   10                  15

Lys Arg Lys Val
            20
```

<210> SEQ ID NO 5
<211> LENGTH: 19
<212> TYPE: PRT
<213> ORGANISM: Human hepatitus B virus

<400> SEQUENCE: 5

```
Pro Leu Ser Ser Ile Phe Ser Arg Ile Gly Asp Pro Pro Lys Lys Lys
1               5                   10                  15

Arg Lys Val
```

<210> SEQ ID NO 6
<211> LENGTH: 1839
<212> TYPE: PRT
<213> ORGANISM: Artificial Sequence
<220> FEATURE:
<223> OTHER INFORMATION: Fusion protein comprising the wild-type Cas9-
      Spo11 construction

<400> SEQUENCE: 6

-continued

```
Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Gly Ile His
            20                  25                  30

Gly Val Pro Ala Ala Met Asp Lys Lys Tyr Ser Ile Gly Leu Asp Ile
        35                  40                  45

Gly Thr Asn Ser Val Gly Trp Ala Val Ile Thr Asp Glu Tyr Lys Val
    50                  55                  60

Pro Ser Lys Lys Phe Lys Val Leu Gly Asn Thr Asp Arg His Ser Ile
65                  70                  75                  80

Lys Lys Asn Leu Ile Gly Ala Leu Leu Phe Asp Ser Gly Glu Thr Ala
                85                  90                  95

Glu Ala Thr Arg Leu Lys Arg Thr Ala Arg Arg Arg Tyr Thr Arg Arg
            100                 105                 110

Lys Asn Arg Ile Cys Tyr Leu Gln Glu Ile Phe Ser Asn Glu Met Ala
        115                 120                 125

Lys Val Asp Asp Ser Phe Phe His Arg Leu Glu Glu Ser Phe Leu Val
    130                 135                 140

Glu Glu Asp Lys Lys His Glu Arg His Pro Ile Phe Gly Asn Ile Val
145                 150                 155                 160

Asp Glu Val Ala Tyr His Glu Lys Tyr Pro Thr Ile Tyr His Leu Arg
                165                 170                 175

Lys Lys Leu Val Asp Ser Thr Asp Lys Ala Asp Leu Arg Leu Ile Tyr
            180                 185                 190

Leu Ala Leu Ala His Met Ile Lys Phe Arg Gly His Phe Leu Ile Glu
        195                 200                 205

Gly Asp Leu Asn Pro Asp Asn Ser Asp Val Asp Lys Leu Phe Ile Gln
    210                 215                 220

Leu Val Gln Thr Tyr Asn Gln Leu Phe Glu Glu Asn Pro Ile Asn Ala
225                 230                 235                 240

Ser Gly Val Asp Ala Lys Ala Ile Leu Ser Ala Arg Leu Ser Lys Ser
                245                 250                 255

Arg Arg Leu Glu Asn Leu Ile Ala Gln Leu Pro Gly Glu Lys Lys Asn
            260                 265                 270

Gly Leu Phe Gly Asn Leu Ile Ala Leu Ser Leu Gly Leu Thr Pro Asn
        275                 280                 285

Phe Lys Ser Asn Phe Asp Leu Ala Glu Asp Ala Lys Leu Gln Leu Ser
    290                 295                 300

Lys Asp Thr Tyr Asp Asp Asp Leu Asp Asn Leu Leu Ala Gln Ile Gly
305                 310                 315                 320

Asp Gln Tyr Ala Asp Leu Phe Leu Ala Ala Lys Asn Leu Ser Asp Ala
                325                 330                 335

Ile Leu Leu Ser Asp Ile Leu Arg Val Asn Thr Glu Ile Thr Lys Ala
            340                 345                 350

Pro Leu Ser Ala Ser Met Ile Lys Arg Tyr Asp Glu His His Gln Asp
        355                 360                 365

Leu Thr Leu Leu Lys Ala Leu Val Arg Gln Gln Leu Pro Glu Lys Tyr
    370                 375                 380

Lys Glu Ile Phe Phe Asp Gln Ser Lys Asn Gly Tyr Ala Gly Tyr Ile
385                 390                 395                 400

Asp Gly Gly Ala Ser Gln Glu Glu Phe Tyr Lys Phe Ile Lys Pro Ile
                405                 410                 415
```

-continued

```
Leu Glu Lys Met Asp Gly Thr Glu Glu Leu Leu Val Lys Leu Asn Arg
            420                 425                 430

Glu Asp Leu Leu Arg Lys Gln Arg Thr Phe Asp Asn Gly Ser Ile Pro
        435                 440                 445

His Gln Ile His Leu Gly Glu Leu His Ala Ile Leu Arg Arg Gln Glu
    450                 455                 460

Asp Phe Tyr Pro Phe Leu Lys Asp Asn Arg Glu Lys Ile Glu Lys Ile
465                 470                 475                 480

Leu Thr Phe Arg Ile Pro Tyr Tyr Val Gly Pro Leu Ala Arg Gly Asn
                485                 490                 495

Ser Arg Phe Ala Trp Met Thr Arg Lys Ser Glu Glu Thr Ile Thr Pro
            500                 505                 510

Trp Asn Phe Glu Glu Val Val Asp Lys Gly Ala Ser Ala Gln Ser Phe
        515                 520                 525

Ile Glu Arg Met Thr Asn Phe Asp Lys Asn Leu Pro Asn Glu Lys Val
    530                 535                 540

Leu Pro Lys His Ser Leu Leu Tyr Glu Tyr Phe Thr Val Tyr Asn Glu
545                 550                 555                 560

Leu Thr Lys Val Lys Tyr Val Thr Glu Gly Met Arg Lys Pro Ala Phe
                565                 570                 575

Leu Ser Gly Glu Gln Lys Lys Ala Ile Val Asp Leu Leu Phe Lys Thr
            580                 585                 590

Asn Arg Lys Val Thr Val Lys Gln Leu Lys Glu Asp Tyr Phe Lys Lys
        595                 600                 605

Ile Glu Cys Phe Asp Ser Val Glu Ile Ser Gly Val Glu Asp Arg Phe
    610                 615                 620

Asn Ala Ser Leu Gly Thr Tyr His Asp Leu Leu Lys Ile Ile Lys Asp
625                 630                 635                 640

Lys Asp Phe Leu Asp Asn Glu Glu Asn Glu Asp Ile Leu Glu Asp Ile
                645                 650                 655

Val Leu Thr Leu Thr Leu Phe Glu Asp Arg Glu Met Ile Glu Glu Arg
            660                 665                 670

Leu Lys Thr Tyr Ala His Leu Phe Asp Asp Lys Val Met Lys Gln Leu
        675                 680                 685

Lys Arg Arg Arg Tyr Thr Gly Trp Gly Arg Leu Ser Arg Lys Leu Ile
    690                 695                 700

Asn Gly Ile Arg Asp Lys Gln Ser Gly Lys Thr Ile Leu Asp Phe Leu
705                 710                 715                 720

Lys Ser Asp Gly Phe Ala Asn Arg Asn Phe Met Gln Leu Ile His Asp
                725                 730                 735

Asp Ser Leu Thr Phe Lys Glu Asp Ile Gln Lys Ala Gln Val Ser Gly
            740                 745                 750

Gln Gly Asp Ser Leu His Glu His Ile Ala Asn Leu Ala Gly Ser Pro
        755                 760                 765

Ala Ile Lys Lys Gly Ile Leu Gln Thr Val Lys Val Val Asp Glu Leu
    770                 775                 780

Val Lys Val Met Gly Arg His Lys Pro Glu Asn Ile Val Ile Glu Met
785                 790                 795                 800

Ala Arg Glu Asn Gln Thr Thr Gln Lys Gly Gln Lys Asn Ser Arg Glu
                805                 810                 815

Arg Met Lys Arg Ile Glu Glu Gly Ile Lys Glu Leu Gly Ser Gln Ile
            820                 825                 830

Leu Lys Glu His Pro Val Glu Asn Thr Gln Leu Gln Asn Glu Lys Leu
```

-continued

```
        835                 840                 845

Tyr Leu Tyr Tyr Leu Gln Asn Gly Arg Asp Met Tyr Val Asp Gln Glu
    850                 855                 860

Leu Asp Ile Asn Arg Leu Ser Asp Tyr Asp Val Asp His Ile Val Pro
865                 870                 875                 880

Gln Ser Phe Leu Lys Asp Asp Ser Ile Asp Asn Lys Val Leu Thr Arg
                885                 890                 895

Ser Asp Lys Asn Arg Gly Lys Ser Asp Asn Val Pro Ser Glu Glu Val
            900                 905                 910

Val Lys Lys Met Lys Asn Tyr Trp Arg Gln Leu Leu Asn Ala Lys Leu
        915                 920                 925

Ile Thr Gln Arg Lys Phe Asp Asn Leu Thr Lys Ala Glu Arg Gly Gly
    930                 935                 940

Leu Ser Glu Leu Asp Lys Ala Gly Phe Ile Lys Arg Gln Leu Val Glu
945                 950                 955                 960

Thr Arg Gln Ile Thr Lys His Val Ala Gln Ile Leu Asp Ser Arg Met
                965                 970                 975

Asn Thr Lys Tyr Asp Glu Asn Asp Lys Leu Ile Arg Glu Val Lys Val
            980                 985                 990

Ile Thr Leu Lys Ser Lys Leu Val  Ser Asp Phe Arg Lys  Asp Phe Gln
        995                 1000                1005

Phe Tyr  Lys Val Arg Glu Ile  Asn Asn Tyr His His  Ala His Asp
    1010                1015                1020

Ala Tyr  Leu Asn Ala Val Val  Gly Thr Ala Leu Ile  Lys Lys Tyr
    1025                1030                1035

Pro Lys  Leu Glu Ser Glu Phe  Val Tyr Gly Asp Tyr  Lys Val Tyr
    1040                1045                1050

Asp Val  Arg Lys Met Ile Ala  Lys Ser Glu Gln Glu  Ile Gly Lys
    1055                1060                1065

Ala Thr  Ala Lys Tyr Phe Phe  Tyr Ser Asn Ile Met  Asn Phe Phe
    1070                1075                1080

Lys Thr  Glu Ile Thr Leu Ala  Asn Gly Glu Ile Arg  Lys Arg Pro
    1085                1090                1095

Leu Ile  Glu Thr Asn Gly Glu  Thr Gly Glu Ile Val  Trp Asp Lys
    1100                1105                1110

Gly Arg  Asp Phe Ala Thr Val  Arg Lys Val Leu Ser  Met Pro Gln
    1115                1120                1125

Val Asn  Ile Val Lys Lys Thr  Glu Val Gln Thr Gly  Gly Phe Ser
    1130                1135                1140

Lys Glu  Ser Ile Leu Pro Lys  Arg Asn Ser Asp Lys  Leu Ile Ala
    1145                1150                1155

Arg Lys  Lys Asp Trp Asp Pro  Lys Lys Tyr Gly Gly  Phe Asp Ser
    1160                1165                1170

Pro Thr  Val Ala Tyr Ser Val  Leu Val Val Ala Lys  Val Glu Lys
    1175                1180                1185

Gly Lys  Ser Lys Lys Leu Lys  Ser Val Lys Glu Leu  Leu Gly Ile
    1190                1195                1200

Thr Ile  Met Glu Arg Ser Ser  Phe Glu Lys Asn Pro  Ile Asp Phe
    1205                1210                1215

Leu Glu  Ala Lys Gly Tyr Lys  Glu Val Lys Lys Asp  Leu Ile Ile
    1220                1225                1230

Lys Leu  Pro Lys Tyr Ser Leu  Phe Glu Leu Glu Asn  Gly Arg Lys
    1235                1240                1245
```

-continued

```
Arg Met  Leu Ala Ser Ala Gly  Glu Leu Gln Lys Gly  Asn Glu Leu
    1250                 1255                 1260

Ala Leu  Pro Ser Lys Tyr Val  Asn Phe Leu Tyr Leu  Ala Ser His
    1265                 1270                 1275

Tyr Glu  Lys Leu Lys Gly Ser  Pro Glu Asp Asn Glu  Gln Lys Gln
    1280                 1285                 1290

Leu Phe  Val Glu Gln His Lys  His Tyr Leu Asp Glu  Ile Ile Glu
    1295                 1300                 1305

Gln Ile  Ser Glu Phe Ser Lys  Arg Val Ile Leu Ala  Asp Ala Asn
    1310                 1315                 1320

Leu Asp  Lys Val Leu Ser Ala  Tyr Asn Lys His Arg  Asp Lys Pro
    1325                 1330                 1335

Ile Arg  Glu Gln Ala Glu Asn  Ile Ile His Leu Phe  Thr Leu Thr
    1340                 1345                 1350

Asn Leu  Gly Ala Pro Ala Ala  Phe Lys Tyr Phe Asp  Thr Thr Ile
    1355                 1360                 1365

Asp Arg  Lys Arg Tyr Thr Ser  Thr Lys Glu Val Leu  Asp Ala Thr
    1370                 1375                 1380

Leu Ile  His Gln Ser Ile Thr  Gly Leu Tyr Glu Thr  Arg Ile Asp
    1385                 1390                 1395

Leu Ser  Gln Leu Gly Gly Asp  Pro Glu Phe Met Ala  Met Glu Ala
    1400                 1405                 1410

Pro Gly  Ile Arg Met Ala Leu  Glu Gly Leu Arg Lys  Lys Tyr Lys
    1415                 1420                 1425

Thr Arg  Gln Glu Leu Val Lys  Ala Leu Thr Pro Lys  Arg Arg Ser
    1430                 1435                 1440

Ile His  Leu Asn Ser Asn Gly  His Ser Asn Gly Thr  Pro Cys Ser
    1445                 1450                 1455

Asn Ala  Asp Val Leu Ala His  Ile Lys His Phe Leu  Ser Leu Ala
    1460                 1465                 1470

Ala Asn  Ser Leu Glu Gln His  Gln Gln Pro Ile Ser  Ile Val Phe
    1475                 1480                 1485

Gln Asn  Lys Lys Lys Lys Gly  Asp Thr Ser Ser Pro  Asp Ile His
    1490                 1495                 1500

Thr Thr  Leu Asp Phe Pro Leu  Asn Gly Pro His Leu  Cys Thr His
    1505                 1510                 1515

Gln Phe  Lys Leu Lys Arg Cys  Ala Ile Leu Leu Asn  Leu Leu Lys
    1520                 1525                 1530

Val Val  Met Glu Lys Leu Pro  Leu Gly Lys Asn Thr  Thr Val Arg
    1535                 1540                 1545

Asp Ile  Phe Tyr Ser Asn Val  Glu Leu Phe Gln Arg  Gln Ala Asn
    1550                 1555                 1560

Val Val  Gln Trp Leu Asp Val  Ile Arg Phe Asn Phe  Lys Leu Ser
    1565                 1570                 1575

Pro Arg  Lys Ser Leu Asn Ile  Ile Pro Ala Gln Lys  Gly Leu Val
    1580                 1585                 1590

Tyr Ser  Pro Phe Pro Ile Asp  Ile Tyr Asp Asn Ile  Leu Thr Cys
    1595                 1600                 1605

Glu Asn  Glu Pro Lys Met Gln  Lys Gln Thr Ile Phe  Pro Gly Lys
    1610                 1615                 1620

Pro Cys  Leu Ile Pro Phe Phe  Gln Asp Asp Ala Val  Ile Lys Leu
    1625                 1630                 1635
```

```
Gly Thr  Thr Ser Met Cys Asn  Ile Val Ile Val Glu  Lys Glu Ala
    1640                 1645                 1650

Val Phe  Thr Lys Leu Val Asn  Asn Tyr His Lys Leu  Ser Thr Asn
    1655                 1660                 1665

Thr Met  Leu Ile Thr Gly Lys  Gly Phe Pro Asp Phe  Leu Thr Arg
    1670                 1675                 1680

Leu Phe  Leu Lys Lys Leu Glu  Gln Tyr Cys Ser Lys  Leu Ile Ser
    1685                 1690                 1695

Asp Cys  Ser Ile Phe Thr Asp  Ala Asp Pro Tyr Gly  Ile Ser Ile
    1700                 1705                 1710

Ala Leu  Asn Tyr Thr His Ser  Asn Glu Arg Asn Ala  Tyr Ile Cys
    1715                 1720                 1725

Thr Met  Ala Asn Tyr Lys Gly  Ile Arg Ile Thr Gln  Val Leu Ala
    1730                 1735                 1740

Gln Asn  Asn Glu Val His Asn  Lys Ser Ile Gln Leu  Leu Ser Leu
    1745                 1750                 1755

Asn Gln  Arg Asp Tyr Ser Leu  Ala Lys Asn Leu Ile  Ala Ser Leu
    1760                 1765                 1770

Thr Ala  Asn Ser Trp Asp Ile  Ala Thr Ser Pro Leu  Lys Asn Val
    1775                 1780                 1785

Ile Ile  Glu Cys Gln Arg Glu  Ile Phe Phe Gln Lys  Lys Ala Glu
    1790                 1795                 1800

Met Asn  Glu Ile Asp Ala Arg  Ile Phe Glu Tyr Lys  Asp Tyr Lys
    1805                 1810                 1815

Asp Asp  Asp Asp Lys Asp Tyr  Lys Asp Asp Asp Asp  Lys Asp Tyr
    1820                 1825                 1830

Lys Asp  Asp Asp Asp Lys
    1835


<210> SEQ ID NO 7
<211> LENGTH: 1839
<212> TYPE: PRT
<213> ORGANISM: Artificial Sequence
<220> FEATURE:
<223> OTHER INFORMATION: Fusion protein comprising the Cas9*-Spo11
      construction

<400> SEQUENCE: 7

Met Gly Lys Pro Ile Pro Asn Pro Leu Leu Gly Leu Asp Ser Thr Gly
1               5                   10                  15

Gly Met Ala Pro Lys Lys Lys Arg Lys Val Asp Gly Gly Gly Ile His
            20                  25                  30

Gly Val Pro Ala Ala Met Asp Lys Lys Tyr Ser Ile Gly Leu Ala Ile
        35                  40                  45

Gly Thr Asn Ser Val Gly Trp Ala Val Ile Thr Asp Glu Tyr Lys Val
    50                  55                  60

Pro Ser Lys Lys Phe Lys Val Leu Gly Asn Thr Asp Arg His Ser Ile
65                  70                  75                  80

Lys Lys Asn Leu Ile Gly Ala Leu Leu Phe Asp Ser Gly Glu Thr Ala
                85                  90                  95

Glu Ala Thr Arg Leu Lys Arg Thr Ala Arg Arg Arg Tyr Thr Arg Arg
            100                 105                 110

Lys Asn Arg Ile Cys Tyr Leu Gln Glu Ile Phe Ser Asn Glu Met Ala
        115                 120                 125

Lys Val Asp Asp Ser Phe Phe His Arg Leu Glu Glu Ser Phe Leu Val
    130                 135                 140
```

```
Glu Glu Asp Lys Lys His Glu Arg His Pro Ile Phe Gly Asn Ile Val
145                 150                 155                 160

Asp Glu Val Ala Tyr His Glu Lys Tyr Pro Thr Ile Tyr His Leu Arg
                165                 170                 175

Lys Lys Leu Val Asp Ser Thr Asp Lys Ala Asp Leu Arg Leu Ile Tyr
            180                 185                 190

Leu Ala Leu Ala His Met Ile Lys Phe Arg Gly His Phe Leu Ile Glu
        195                 200                 205

Gly Asp Leu Asn Pro Asp Asn Ser Asp Val Asp Lys Leu Phe Ile Gln
    210                 215                 220

Leu Val Gln Thr Tyr Asn Gln Leu Phe Glu Glu Asn Pro Ile Asn Ala
225                 230                 235                 240

Ser Gly Val Asp Ala Lys Ala Ile Leu Ser Ala Arg Leu Ser Lys Ser
                245                 250                 255

Arg Arg Leu Glu Asn Leu Ile Ala Gln Leu Pro Gly Glu Lys Lys Asn
            260                 265                 270

Gly Leu Phe Gly Asn Leu Ile Ala Leu Ser Leu Gly Leu Thr Pro Asn
        275                 280                 285

Phe Lys Ser Asn Phe Asp Leu Ala Glu Asp Ala Lys Leu Gln Leu Ser
    290                 295                 300

Lys Asp Thr Tyr Asp Asp Asp Leu Asp Asn Leu Leu Ala Gln Ile Gly
305                 310                 315                 320

Asp Gln Tyr Ala Asp Leu Phe Leu Ala Ala Lys Asn Leu Ser Asp Ala
                325                 330                 335

Ile Leu Leu Ser Asp Ile Leu Arg Val Asn Thr Glu Ile Thr Lys Ala
            340                 345                 350

Pro Leu Ser Ala Ser Met Ile Lys Arg Tyr Asp Glu His His Gln Asp
        355                 360                 365

Leu Thr Leu Leu Lys Ala Leu Val Arg Gln Gln Leu Pro Glu Lys Tyr
    370                 375                 380

Lys Glu Ile Phe Phe Asp Gln Ser Lys Asn Gly Tyr Ala Gly Tyr Ile
385                 390                 395                 400

Asp Gly Gly Ala Ser Gln Glu Glu Phe Tyr Lys Phe Ile Lys Pro Ile
                405                 410                 415

Leu Glu Lys Met Asp Gly Thr Glu Glu Leu Leu Val Lys Leu Asn Arg
            420                 425                 430

Glu Asp Leu Leu Arg Lys Gln Arg Thr Phe Asp Asn Gly Ser Ile Pro
        435                 440                 445

His Gln Ile His Leu Gly Glu Leu His Ala Ile Leu Arg Arg Gln Glu
    450                 455                 460

Asp Phe Tyr Pro Phe Leu Lys Asp Asn Arg Glu Lys Ile Glu Lys Ile
465                 470                 475                 480

Leu Thr Phe Arg Ile Pro Tyr Tyr Val Gly Pro Leu Ala Arg Gly Asn
                485                 490                 495

Ser Arg Phe Ala Trp Met Thr Arg Lys Ser Glu Glu Thr Ile Thr Pro
            500                 505                 510

Trp Asn Phe Glu Glu Val Val Asp Lys Gly Ala Ser Ala Gln Ser Phe
        515                 520                 525

Ile Glu Arg Met Thr Asn Phe Asp Lys Asn Leu Pro Asn Glu Lys Val
    530                 535                 540

Leu Pro Lys His Ser Leu Leu Tyr Glu Tyr Phe Thr Val Tyr Asn Glu
545                 550                 555                 560
```

-continued

```
Leu Thr Lys Val Lys Tyr Val Thr Glu Gly Met Arg Lys Pro Ala Phe
                565                 570                 575

Leu Ser Gly Glu Gln Lys Lys Ala Ile Val Asp Leu Leu Phe Lys Thr
            580                 585                 590

Asn Arg Lys Val Thr Val Lys Gln Leu Lys Glu Asp Tyr Phe Lys Lys
        595                 600                 605

Ile Glu Cys Phe Asp Ser Val Glu Ile Ser Gly Val Glu Asp Arg Phe
    610                 615                 620

Asn Ala Ser Leu Gly Thr Tyr His Asp Leu Leu Lys Ile Ile Lys Asp
625                 630                 635                 640

Lys Asp Phe Leu Asp Asn Glu Glu Asn Glu Asp Ile Leu Glu Asp Ile
                645                 650                 655

Val Leu Thr Leu Thr Leu Phe Glu Asp Arg Glu Met Ile Glu Glu Arg
            660                 665                 670

Leu Lys Thr Tyr Ala His Leu Phe Asp Asp Lys Val Met Lys Gln Leu
        675                 680                 685

Lys Arg Arg Arg Tyr Thr Gly Trp Gly Arg Leu Ser Arg Lys Leu Ile
    690                 695                 700

Asn Gly Ile Arg Asp Lys Gln Ser Gly Lys Thr Ile Leu Asp Phe Leu
705                 710                 715                 720

Lys Ser Asp Gly Phe Ala Asn Arg Asn Phe Met Gln Leu Ile His Asp
                725                 730                 735

Asp Ser Leu Thr Phe Lys Glu Asp Ile Gln Lys Ala Gln Val Ser Gly
            740                 745                 750

Gln Gly Asp Ser Leu His Glu His Ile Ala Asn Leu Ala Gly Ser Pro
        755                 760                 765

Ala Ile Lys Lys Gly Ile Leu Gln Thr Val Lys Val Val Asp Glu Leu
    770                 775                 780

Val Lys Val Met Gly Arg His Lys Pro Glu Asn Ile Val Ile Glu Met
785                 790                 795                 800

Ala Arg Glu Asn Gln Thr Thr Gln Lys Gly Gln Lys Asn Ser Arg Glu
                805                 810                 815

Arg Met Lys Arg Ile Glu Glu Gly Ile Lys Glu Leu Gly Ser Gln Ile
            820                 825                 830

Leu Lys Glu His Pro Val Glu Asn Thr Gln Leu Gln Asn Glu Lys Leu
        835                 840                 845

Tyr Leu Tyr Tyr Leu Gln Asn Gly Arg Asp Met Tyr Val Asp Gln Glu
    850                 855                 860

Leu Asp Ile Asn Arg Leu Ser Asp Tyr Asp Val Asp Ala Ile Val Pro
865                 870                 875                 880

Gln Ser Phe Leu Lys Asp Asp Ser Ile Asp Asn Lys Val Leu Thr Arg
                885                 890                 895

Ser Asp Lys Asn Arg Gly Lys Ser Asp Asn Val Pro Ser Glu Glu Val
            900                 905                 910

Val Lys Lys Met Lys Asn Tyr Trp Arg Gln Leu Leu Asn Ala Lys Leu
        915                 920                 925

Ile Thr Gln Arg Lys Phe Asp Asn Leu Thr Lys Ala Glu Arg Gly Gly
    930                 935                 940

Leu Ser Glu Leu Asp Lys Ala Gly Phe Ile Lys Arg Gln Leu Val Glu
945                 950                 955                 960

Thr Arg Gln Ile Thr Lys His Val Ala Gln Ile Leu Asp Ser Arg Met
                965                 970                 975

Asn Thr Lys Tyr Asp Glu Asn Asp Lys Leu Ile Arg Glu Val Lys Val
```

-continued 980 985 990

Ile Thr Leu Lys Ser Lys Leu Val Ser Asp Phe Arg Lys Asp Phe Gln
995 1000 1005

Phe Tyr Lys Val Arg Glu Ile Asn Asn Tyr His His Ala His Asp
1010 1015 1020

Ala Tyr Leu Asn Ala Val Val Gly Thr Ala Leu Ile Lys Lys Tyr
1025 1030 1035

Pro Lys Leu Glu Ser Glu Phe Val Tyr Gly Asp Tyr Lys Val Tyr
1040 1045 1050

Asp Val Arg Lys Met Ile Ala Lys Ser Glu Gln Glu Ile Gly Lys
1055 1060 1065

Ala Thr Ala Lys Tyr Phe Phe Tyr Ser Asn Ile Met Asn Phe Phe
1070 1075 1080

Lys Thr Glu Ile Thr Leu Ala Asn Gly Glu Ile Arg Lys Arg Pro
1085 1090 1095

Leu Ile Glu Thr Asn Gly Glu Thr Gly Glu Ile Val Trp Asp Lys
1100 1105 1110

Gly Arg Asp Phe Ala Thr Val Arg Lys Val Leu Ser Met Pro Gln
1115 1120 1125

Val Asn Ile Val Lys Lys Thr Glu Val Gln Thr Gly Gly Phe Ser
1130 1135 1140

Lys Glu Ser Ile Leu Pro Lys Arg Asn Ser Asp Lys Leu Ile Ala
1145 1150 1155

Arg Lys Lys Asp Trp Asp Pro Lys Lys Tyr Gly Gly Phe Asp Ser
1160 1165 1170

Pro Thr Val Ala Tyr Ser Val Leu Val Val Ala Lys Val Glu Lys
1175 1180 1185

Gly Lys Ser Lys Lys Leu Lys Ser Val Lys Glu Leu Leu Gly Ile
1190 1195 1200

Thr Ile Met Glu Arg Ser Ser Phe Glu Lys Asn Pro Ile Asp Phe
1205 1210 1215

Leu Glu Ala Lys Gly Tyr Lys Glu Val Lys Lys Asp Leu Ile Ile
1220 1225 1230

Lys Leu Pro Lys Tyr Ser Leu Phe Glu Leu Glu Asn Gly Arg Lys
1235 1240 1245

Arg Met Leu Ala Ser Ala Gly Glu Leu Gln Lys Gly Asn Glu Leu
1250 1255 1260

Ala Leu Pro Ser Lys Tyr Val Asn Phe Leu Tyr Leu Ala Ser His
1265 1270 1275

Tyr Glu Lys Leu Lys Gly Ser Pro Glu Asp Asn Glu Gln Lys Gln
1280 1285 1290

Leu Phe Val Glu Gln His Lys His Tyr Leu Asp Glu Ile Ile Glu
1295 1300 1305

Gln Ile Ser Glu Phe Ser Lys Arg Val Ile Leu Ala Asp Ala Asn
1310 1315 1320

Leu Asp Lys Val Leu Ser Ala Tyr Asn Lys His Arg Asp Lys Pro
1325 1330 1335

Ile Arg Glu Gln Ala Glu Asn Ile Ile His Leu Phe Thr Leu Thr
1340 1345 1350

Asn Leu Gly Ala Pro Ala Ala Phe Lys Tyr Phe Asp Thr Thr Ile
1355 1360 1365

Asp Arg Lys Arg Tyr Thr Ser Thr Lys Glu Val Leu Asp Ala Thr
1370 1375 1380

-continued

```
Leu Ile  His Gln Ser Ile Thr  Gly Leu Tyr Glu Thr  Arg Ile Asp
    1385                 1390                 1395

Leu Ser  Gln Leu Gly Gly Asp  Pro Glu Phe Met Ala  Met Glu Ala
    1400                 1405                 1410

Pro Gly  Ile Arg Met Ala Leu  Glu Gly Leu Arg Lys  Lys Tyr Lys
    1415                 1420                 1425

Thr Arg  Gln Glu Leu Val Lys  Ala Leu Thr Pro Lys  Arg Arg Ser
    1430                 1435                 1440

Ile His  Leu Asn Ser Asn Gly  His Ser Asn Gly Thr  Pro Cys Ser
    1445                 1450                 1455

Asn Ala  Asp Val Leu Ala His  Ile Lys His Phe Leu  Ser Leu Ala
    1460                 1465                 1470

Ala Asn  Ser Leu Glu Gln His  Gln Gln Pro Ile Ser  Ile Val Phe
    1475                 1480                 1485

Gln Asn  Lys Lys Lys Lys Gly  Asp Thr Ser Ser Pro  Asp Ile His
    1490                 1495                 1500

Thr Thr  Leu Asp Phe Pro Leu  Asn Gly Pro His Leu  Cys Thr His
    1505                 1510                 1515

Gln Phe  Lys Leu Lys Arg Cys  Ala Ile Leu Leu Asn  Leu Leu Lys
    1520                 1525                 1530

Val Val  Met Glu Lys Leu Pro  Leu Gly Lys Asn Thr  Thr Val Arg
    1535                 1540                 1545

Asp Ile  Phe Tyr Ser Asn Val  Glu Leu Phe Gln Arg  Gln Ala Asn
    1550                 1555                 1560

Val Val  Gln Trp Leu Asp Val  Ile Arg Phe Asn Phe  Lys Leu Ser
    1565                 1570                 1575

Pro Arg  Lys Ser Leu Asn Ile  Ile Pro Ala Gln Lys  Gly Leu Val
    1580                 1585                 1590

Tyr Ser  Pro Phe Pro Ile Asp  Ile Tyr Asp Asn Ile  Leu Thr Cys
    1595                 1600                 1605

Glu Asn  Glu Pro Lys Met Gln  Lys Gln Thr Ile Phe  Pro Gly Lys
    1610                 1615                 1620

Pro Cys  Leu Ile Pro Phe Phe  Gln Asp Asp Ala Val  Ile Lys Leu
    1625                 1630                 1635

Gly Thr  Thr Ser Met Cys Asn  Ile Val Ile Val Glu  Lys Glu Ala
    1640                 1645                 1650

Val Phe  Thr Lys Leu Val Asn  Asn Tyr His Lys Leu  Ser Thr Asn
    1655                 1660                 1665

Thr Met  Leu Ile Thr Gly Lys  Gly Phe Pro Asp Phe  Leu Thr Arg
    1670                 1675                 1680

Leu Phe  Leu Lys Lys Leu Glu  Gln Tyr Cys Ser Lys  Leu Ile Ser
    1685                 1690                 1695

Asp Cys  Ser Ile Phe Thr Asp  Ala Asp Pro Tyr Gly  Ile Ser Ile
    1700                 1705                 1710

Ala Leu  Asn Tyr Thr His Ser  Asn Glu Arg Asn Ala  Tyr Ile Cys
    1715                 1720                 1725

Thr Met  Ala Asn Tyr Lys Gly  Ile Arg Ile Thr Gln  Val Leu Ala
    1730                 1735                 1740

Gln Asn  Asn Glu Val His Asn  Lys Ser Ile Gln Leu  Leu Ser Leu
    1745                 1750                 1755

Asn Gln  Arg Asp Tyr Ser Leu  Ala Lys Asn Leu Ile  Ala Ser Leu
    1760                 1765                 1770
```

-continued

Thr Ala Asn Ser Trp Asp Ile Ala Thr Ser Pro Leu Lys Asn Val
1775 1780 1785

Ile Ile Glu Cys Gln Arg Glu Ile Phe Phe Gln Lys Lys Ala Glu
1790 1795 1800

Met Asn Glu Ile Asp Ala Arg Ile Phe Glu Tyr Lys Asp Tyr Lys
1805 1810 1815

Asp Asp Asp Asp Lys Asp Tyr Lys Asp Asp Asp Asp Lys Asp Tyr
1820 1825 1830

Lys Asp Asp Asp Asp Lys
1835

<210> SEQ ID NO 8
<211> LENGTH: 1368
<212> TYPE: PRT
<213> ORGANISM: Streptococcus pyogenes

<400> SEQUENCE: 8

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

Asp Leu Ala Glu Asp Ala Lys Leu Gln Leu Ser Lys Asp Thr Tyr Asp
260 265 270

Asp Asp Leu Asp Asn Leu Leu Ala Gln Ile Gly Asp Gln Tyr Ala Asp
275 280 285

Leu Phe Leu Ala Ala Lys Asn Leu Ser Asp Ala Ile Leu Leu Ser Asp
290 295 300

-continued

```
Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720
```

-continued

```
His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
```

```
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365


<210> SEQ ID NO 9
<211> LENGTH: 398
<212> TYPE: PRT
<213> ORGANISM: Saccharomyces cerevisiae

<400> SEQUENCE: 9

Met Ala Leu Glu Gly Leu Arg Lys Lys Tyr Lys Thr Arg Gln Glu Leu
1               5                   10                  15

Val Lys Ala Leu Thr Pro Lys Arg Arg Ser Ile His Leu Asn Ser Asn
            20                  25                  30

Gly His Ser Asn Gly Thr Pro Cys Ser Asn Ala Asp Val Leu Ala His
        35                  40                  45

Ile Lys His Phe Leu Ser Leu Ala Ala Asn Ser Leu Glu Gln His Gln
    50                  55                  60

Gln Pro Ile Ser Ile Val Phe Gln Asn Lys Lys Lys Lys Gly Asp Thr
65                  70                  75                  80

Ser Ser Pro Asp Ile His Thr Thr Leu Asp Phe Pro Leu Asn Gly Pro
                85                  90                  95

His Leu Cys Thr His Gln Phe Lys Leu Lys Arg Cys Ala Ile Leu Leu
            100                 105                 110

Asn Leu Leu Lys Val Val Met Glu Lys Leu Pro Leu Gly Lys Asn Thr
        115                 120                 125
```

-continued

```
Thr Val Arg Asp Ile Phe Tyr Ser Asn Val Glu Leu Phe Gln Arg Gln
    130                 135                 140

Ala Asn Val Val Gln Trp Leu Asp Val Ile Arg Phe Asn Phe Lys Leu
145                 150                 155                 160

Ser Pro Arg Lys Ser Leu Asn Ile Ile Pro Ala Gln Lys Gly Leu Val
                165                 170                 175

Tyr Ser Pro Phe Pro Ile Asp Ile Tyr Asp Asn Ile Leu Thr Cys Glu
            180                 185                 190

Asn Glu Pro Lys Met Gln Lys Gln Thr Ile Phe Pro Gly Lys Pro Cys
        195                 200                 205

Leu Ile Pro Phe Phe Gln Asp Asp Ala Val Ile Lys Leu Gly Thr Thr
    210                 215                 220

Ser Met Cys Asn Ile Val Ile Val Glu Lys Glu Ala Val Phe Thr Lys
225                 230                 235                 240

Leu Val Asn Asn Tyr His Lys Leu Ser Thr Asn Thr Met Leu Ile Thr
                245                 250                 255

Gly Lys Gly Phe Pro Asp Phe Leu Thr Arg Leu Phe Leu Lys Lys Leu
            260                 265                 270

Glu Gln Tyr Cys Ser Lys Leu Ile Ser Asp Cys Ser Ile Phe Thr Asp
        275                 280                 285

Ala Asp Pro Tyr Gly Ile Ser Ile Ala Leu Asn Tyr Thr His Ser Asn
    290                 295                 300

Glu Arg Asn Ala Tyr Ile Cys Thr Met Ala Asn Tyr Lys Gly Ile Arg
305                 310                 315                 320

Ile Thr Gln Val Leu Ala Gln Asn Asn Glu Val His Asn Lys Ser Ile
                325                 330                 335

Gln Leu Leu Ser Leu Asn Gln Arg Asp Tyr Ser Leu Ala Lys Asn Leu
            340                 345                 350

Ile Ala Ser Leu Thr Ala Asn Ser Trp Asp Ile Ala Thr Ser Pro Leu
        355                 360                 365

Lys Asn Val Ile Ile Glu Cys Gln Arg Glu Ile Phe Phe Gln Lys Lys
    370                 375                 380

Ala Glu Met Asn Glu Ile Asp Ala Arg Ile Phe Glu Tyr Lys
385                 390                 395
```

<210> SEQ ID NO 10
<211> LENGTH: 102
<212> TYPE: DNA
<213> ORGANISM: Artificial Sequence
<220> FEATURE:
<223> OTHER INFORMATION: UAS1 guide RNA targeting the 5' coding region of the YCR048W gene

<400> SEQUENCE: 10

```
cacacctgaa gagcaagtct gttttagagc tagaaatagc aagttaaaat aaggctagtc     60

cgttatcaac ttgaaaaagt ggcaccgagt cggtgctttt tt                       102
```

<210> SEQ ID NO 11
<211> LENGTH: 102
<212> TYPE: DNA
<213> ORGANISM: Artificial Sequence
<220> FEATURE:
<223> OTHER INFORMATION: UAS2 guide RNA targeting the 3' coding region of the YCR048W gene

<400> SEQUENCE: 11

```
ttccacaaca cgcccacctt gttttagagc tagaaatagc aagttaaaat aaggctagtc     60
```

cgttatcaac ttgaaaaagt ggcaccgagt cggtgctttt tt 102

<210> SEQ ID NO 12
<211> LENGTH: 102
<212> TYPE: DNA
<213> ORGANISM: Artificial Sequence
<220> FEATURE:
<223> OTHER INFORMATION: UAS D/E guide RNA targeting the GAL2 gene promoter site

<400> SEQUENCE: 12
gatcactccg aaccgagatt gttttagagc tagaaatagc aagttaaaat aaggctagtc 60
cgttatcaac ttgaaaaagt ggcaccgagt cggtgctttt tt 102

<210> SEQ ID NO 13
<211> LENGTH: 102
<212> TYPE: DNA
<213> ORGANISM: Artificial Sequence
<220> FEATURE:
<223> OTHER INFORMATION: SWC3 guide RNA targeting the SWC3 gene coding region

<400> SEQUENCE: 13
tgcgattgtg taatgagtgg gttttagagc tagaaatagc aagttaaaat aaggctagtc 60
cgttatcaac ttgaaaaagt ggcaccgagt cggtgctttt tt 102

<210> SEQ ID NO 14
<211> LENGTH: 102
<212> TYPE: DNA
<213> ORGANISM: Artificial Sequence
<220> FEATURE:
<223> OTHER INFORMATION: UAS A guide RNA targeting the GAL2 promoter site

<400> SEQUENCE: 14
caattcggaa agcttccttc gttttagagc tagaaatagc aagttaaaat aaggctagtc 60
cgttatcaac ttgaaaaagt ggcaccgagt cggtgctttt tt 102

<210> SEQ ID NO 15
<211> LENGTH: 102
<212> TYPE: DNA
<213> ORGANISM: Artificial Sequence
<220> FEATURE:
<223> OTHER INFORMATION: UAS B guide RNA targeting the GAL2 gene promoter site

<400> SEQUENCE: 15
ttgcctcagg aaggcaccgg gttttagagc tagaaatagc aagttaaaat aaggctagtc 60
cgttatcaac ttgaaaaagt ggcaccgagt cggtgctttt tt 102

<210> SEQ ID NO 16
<211> LENGTH: 102
<212> TYPE: DNA
<213> ORGANISM: Artificial Sequence
<220> FEATURE:
<223> OTHER INFORMATION: PUT4 guide RNA targeting the PUT4 gene coding region

<400> SEQUENCE: 16
gttttgaatt ccgatcacaa gttttagagc tagaaatagc aagttaaaat aaggctagtc 60
cgttatcaac ttgaaaaagt ggcaccgagt cggtgctttt tt 102

<210> SEQ ID NO 17

-continued

```
<211> LENGTH: 36
<212> TYPE: DNA
<213> ORGANISM: Artificial Sequence
<220> FEATURE:
<223> OTHER INFORMATION: linker of the dCas9-SPO11 construction for
      transforming rice cells

<400> SEQUENCE: 17

ccggaattta tggccatgga ggccccgggg atccgt                          36


<210> SEQ ID NO 18
<211> LENGTH: 24
<212> TYPE: DNA
<213> ORGANISM: Artificial Sequence
<220> FEATURE:
<223> OTHER INFORMATION: Linker of the dCas9-SPO11 construction for
      transforming rice cells

<400> SEQUENCE: 18

ggtattcatg gagttcctgc tgcg                                       24
```